US008825151B2

(12) United States Patent
Gopinathan et al.

(10) Patent No.: US 8,825,151 B2
(45) Date of Patent: Sep. 2, 2014

(54) METHODS AND SYSTEMS FOR DETERMINING VASCULAR BODILY LUMEN INFORMATION AND GUIDING MEDICAL DEVICES

(71) Applicant: Angiometrix Corporation, Bethesda, MD (US)

(72) Inventors: Venugopal Gopinathan, Bangalore (IN); Raghavan Subramaniyan, Bangalore (IN); Goutam Dutta, Bangalore (IN); Nitin Patil, Albany, CA (US); Abhijit Patki, Bangalore (IN)

(73) Assignee: Angiometrix Corporation, Bethesda, MD (US)

( * ) Notice: Subject to any disclaimer, the term of this patent is extended or adjusted under 35 U.S.C. 154(b) by 0 days.

(21) Appl. No.: 13/764,462

(22) Filed: Feb. 11, 2013

(65) Prior Publication Data

US 2013/0226024 A1  Aug. 29, 2013

Related U.S. Application Data

(63) Continuation of application No. 13/305,610, filed on Nov. 28, 2011, now Pat. No. 8,374,689, which is a continuation of application No. 13/159,298, filed on Jun. 13, 2011.

(60) Provisional application No. 61/383,744, filed on Sep. 17, 2010.

(30) Foreign Application Priority Data

Jun. 13, 2010 (IN) ........................... 1636/CHE/2010

(51) Int. Cl.
   *A61B 5/00* (2006.01)
(52) U.S. Cl.
   USPC .......................................... 600/547; 600/505

(58) Field of Classification Search
   USPC .......................... 600/505, 506, 526, 547, 587
   See application file for complete search history.

(56) References Cited

U.S. PATENT DOCUMENTS

| 2,630,474 A | 3/1953 | Brown |
| 5,397,308 A | 3/1995 | Ellis et al. |
| 6,010,500 A | 1/2000 | Sherman et al. |
| 6,010,511 A | 1/2000 | Murphy |
| 6,370,421 B1 | 4/2002 | Williams et al. |

(Continued)

FOREIGN PATENT DOCUMENTS

| CN | 201223393 | 4/2009 |
| WO | WO 01/37897 | 5/2001 |

(Continued)

*Primary Examiner* — Max Hindenburg
(74) *Attorney, Agent, or Firm* — Levine Bagade Han LLP

(57) ABSTRACT

Methods and systems for determining information about a vascular bodily lumen are described. An exemplary method includes generating an electrical signal, delivering the electrical signal to a plurality of excitation elements in the vicinity of the vascular bodily lumen, measuring a responsive electrical signal from a plurality of sensing elements in response to the delivered electrical signal, and determining a lumen dimension. Specific embodiments include generating a multiple frequency electrical signal. Another embodiment includes measuring a plurality of responsive signals at a plurality of frequencies. Still other embodiments include using spatial diversity of the excitation elements. Yet other embodiments use method for calibration and de-embedding of such measurements to determine the lumen dimensions. Diagnostic devices incorporating the method are also disclosed, including guide wires, catheters and implants. The methods and systems described herein are advantageous as they do not include injecting a second fluid for the measurements.

18 Claims, 64 Drawing Sheets

(56) References Cited

U.S. PATENT DOCUMENTS

| | | |
|---|---|---|
| 7,406,346 B2 | 7/2008 | Kleen et al. |
| 7,454,244 B2 | 11/2008 | Kassab et al. |
| 7,778,688 B2 | 8/2010 | Strommer |
| 7,899,516 B2 | 3/2011 | Chen et al. |
| 7,930,014 B2 | 4/2011 | Huennekens et al. |
| 8,114,143 B2 | 2/2012 | Kassab et al. |
| 8,165,371 B2 | 4/2012 | Bi et al. |
| 8,332,013 B2 | 12/2012 | Strommer |
| 8,374,689 B2 | 2/2013 | Gopinathan et al. |
| 8,442,618 B2 | 5/2013 | Strommer et al. |
| 2001/0044578 A1 | 11/2001 | Ben-Haim et al. |
| 2003/0182991 A1 | 10/2003 | Spaid et al. |
| 2005/0107688 A1 | 5/2005 | Strommer |
| 2005/0203369 A1 | 9/2005 | Sathyanarayana |
| 2006/0004300 A1 | 1/2006 | Kennedy |
| 2006/0058647 A1 | 3/2006 | Strommer et al. |
| 2006/0064006 A1 | 3/2006 | Strommer et al. |
| 2006/0241465 A1 | 10/2006 | Huennekens et al. |
| 2006/0291704 A1 | 12/2006 | Mcclurg |
| 2007/0083099 A1 | 4/2007 | Henderson et al. |
| 2008/0033316 A1 | 2/2008 | Kassab et al. |
| 2008/0161678 A1 | 7/2008 | Miyazaki et al. |
| 2008/0175463 A1 | 7/2008 | Strommer et al. |
| 2009/0052754 A1 | 2/2009 | Goto et al. |
| 2009/0062684 A1 | 3/2009 | Gregersen et al. |
| 2009/0118637 A1 | 5/2009 | Kassab et al. |
| 2009/0124915 A1 | 5/2009 | Macadam |
| 2009/0178289 A1 | 7/2009 | Sakai et al. |
| 2009/0192405 A1 | 7/2009 | Carney |
| 2009/0204134 A1 | 8/2009 | Kassab |
| 2009/0270738 A1 | 10/2009 | Izatt et al. |
| 2009/0281418 A1 | 11/2009 | Ruijters et al. |
| 2009/0310842 A1 | 12/2009 | Groth et al. |
| 2010/0014735 A1 | 1/2010 | Bi et al. |
| 2010/0016658 A1 | 1/2010 | Zou et al. |
| 2010/0016707 A1 | 1/2010 | Amara et al. |
| 2010/0022899 A1 | 1/2010 | Kolberg et al. |
| 2010/0053209 A1 | 3/2010 | Rauch et al. |
| 2010/0094124 A1 | 4/2010 | Schoonenberg et al. |
| 2010/0113939 A1 | 5/2010 | Mashimo et al. |
| 2010/0191102 A1 | 7/2010 | Steinberg et al. |
| 2010/0210938 A1 | 8/2010 | Verard et al. |
| 2010/0222671 A1 | 9/2010 | Cohen et al. |
| 2010/0298719 A1 | 11/2010 | Kock et al. |
| 2010/0331950 A1 | 12/2010 | Strommer |
| 2011/0019892 A1 | 1/2011 | Rahn et al. |
| 2011/0157177 A1 | 6/2011 | Chen et al. |
| 2011/0196255 A1 | 8/2011 | Kassab |
| 2011/0235885 A1 | 9/2011 | Rauch et al. |
| 2011/0306867 A1 | 12/2011 | Gopinathan et al. |
| 2011/0319791 A1 | 12/2011 | Harry et al. |
| 2012/0041291 A1 | 2/2012 | Ferren et al. |
| 2012/0071782 A1 | 3/2012 | Patil et al. |
| 2012/0101355 A1 | 4/2012 | Gopinathan et al. |
| 2012/0101369 A1 | 4/2012 | Patil et al. |
| 2013/0123694 A1 | 5/2013 | Subramaniyan et al. |
| 2013/0166011 A1 | 6/2013 | Strommer |

FOREIGN PATENT DOCUMENTS

| | | |
|---|---|---|
| WO | WO 2005/070061 | 8/2005 |
| WO | WO 2008/042347 | 4/2008 |
| WO | WO 2008/062358 | 5/2008 |
| WO | WO 2010/042653 | 4/2010 |

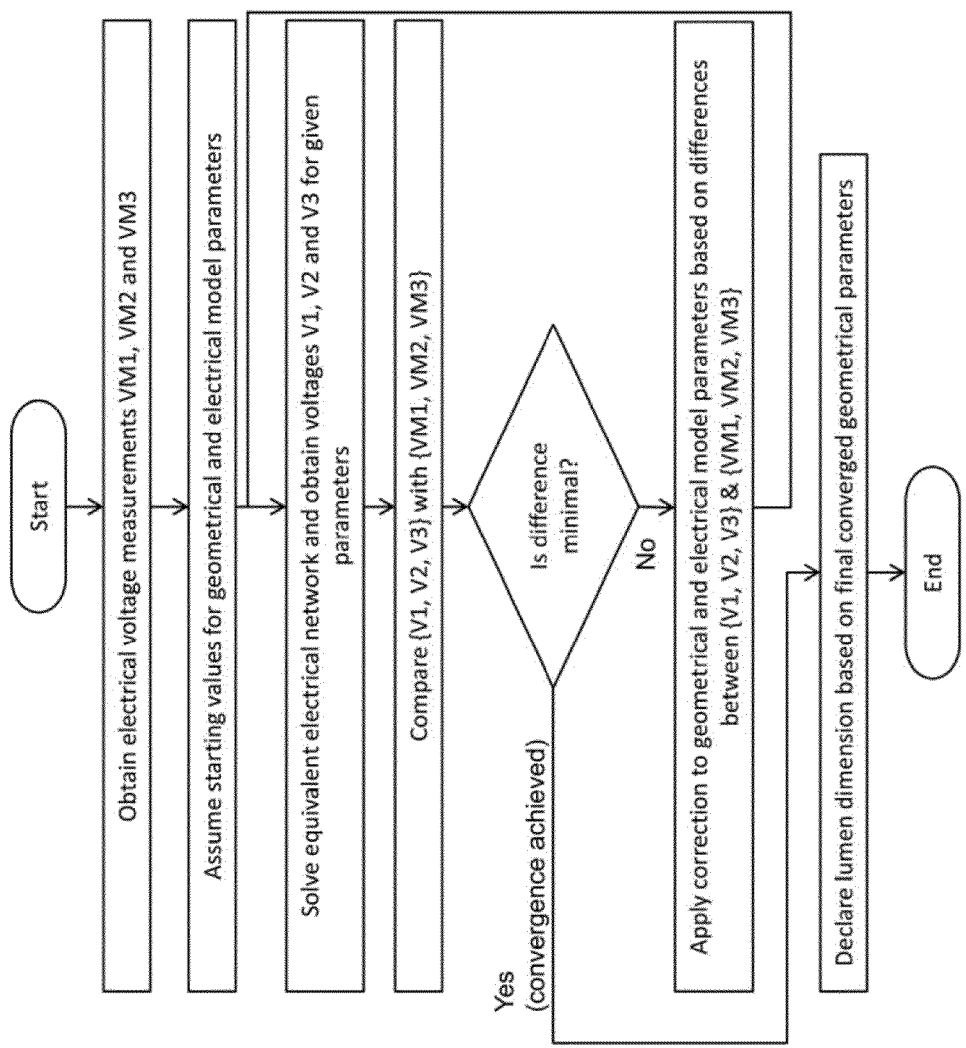
FIG 7A : Lumen Dimension Algorithm using equivalent electrical network

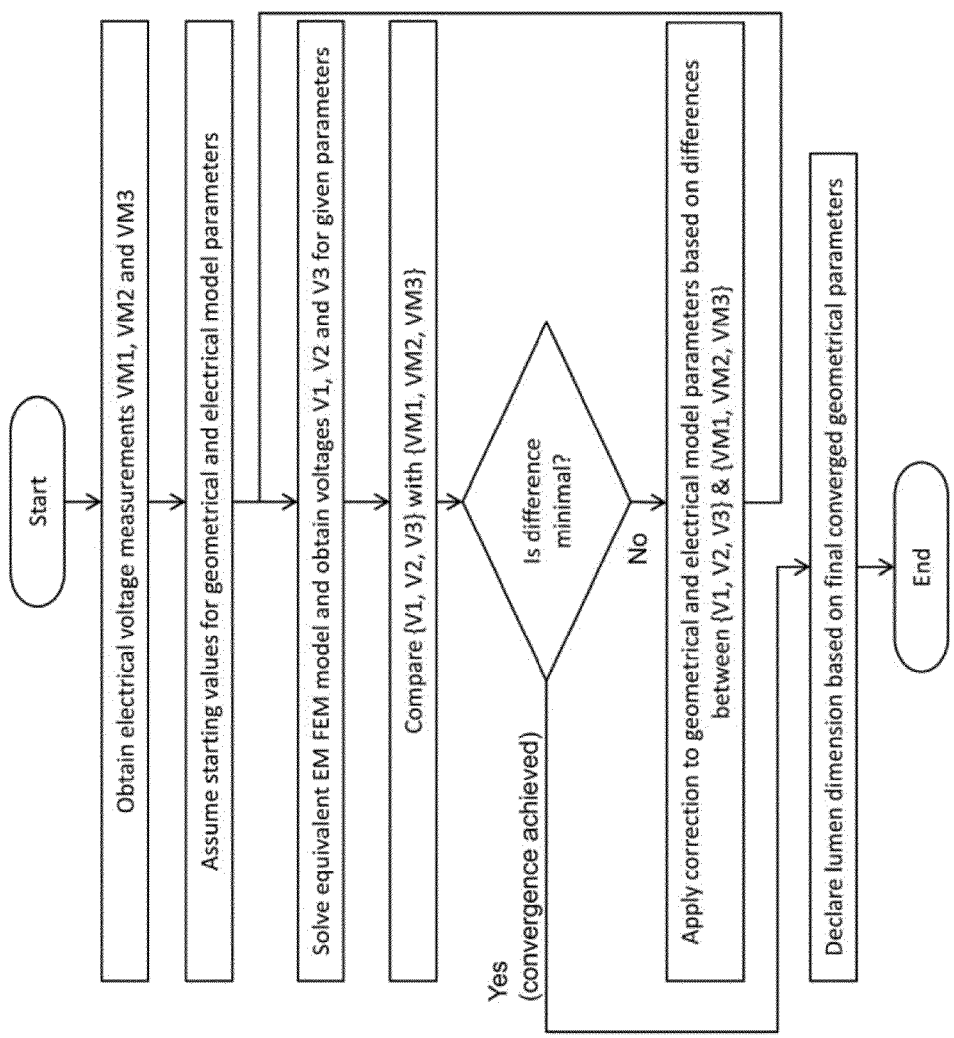
FIG 8A : Lumen Dimension Algorithm using EM solver

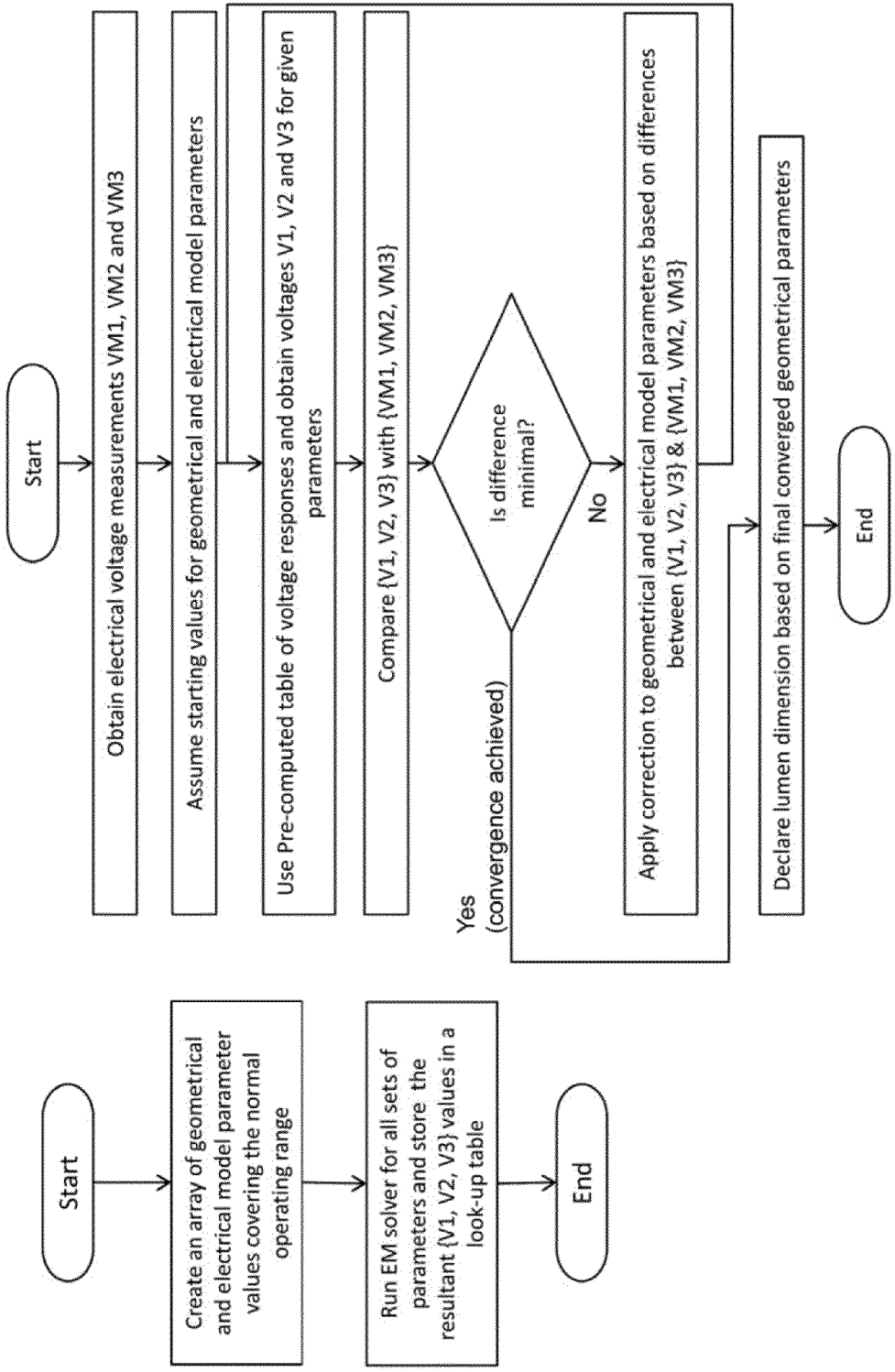
FIG 8B: Lumen Dimension Algorithm using pre-computed Voltage Response Table Time Domain Waveform of a 9-tap Pseudo Random sequence of amplitude 391.4 uA Time Domain Waveform of a 9-tap Pseudo Random sequence of amplitude 391.4 uA

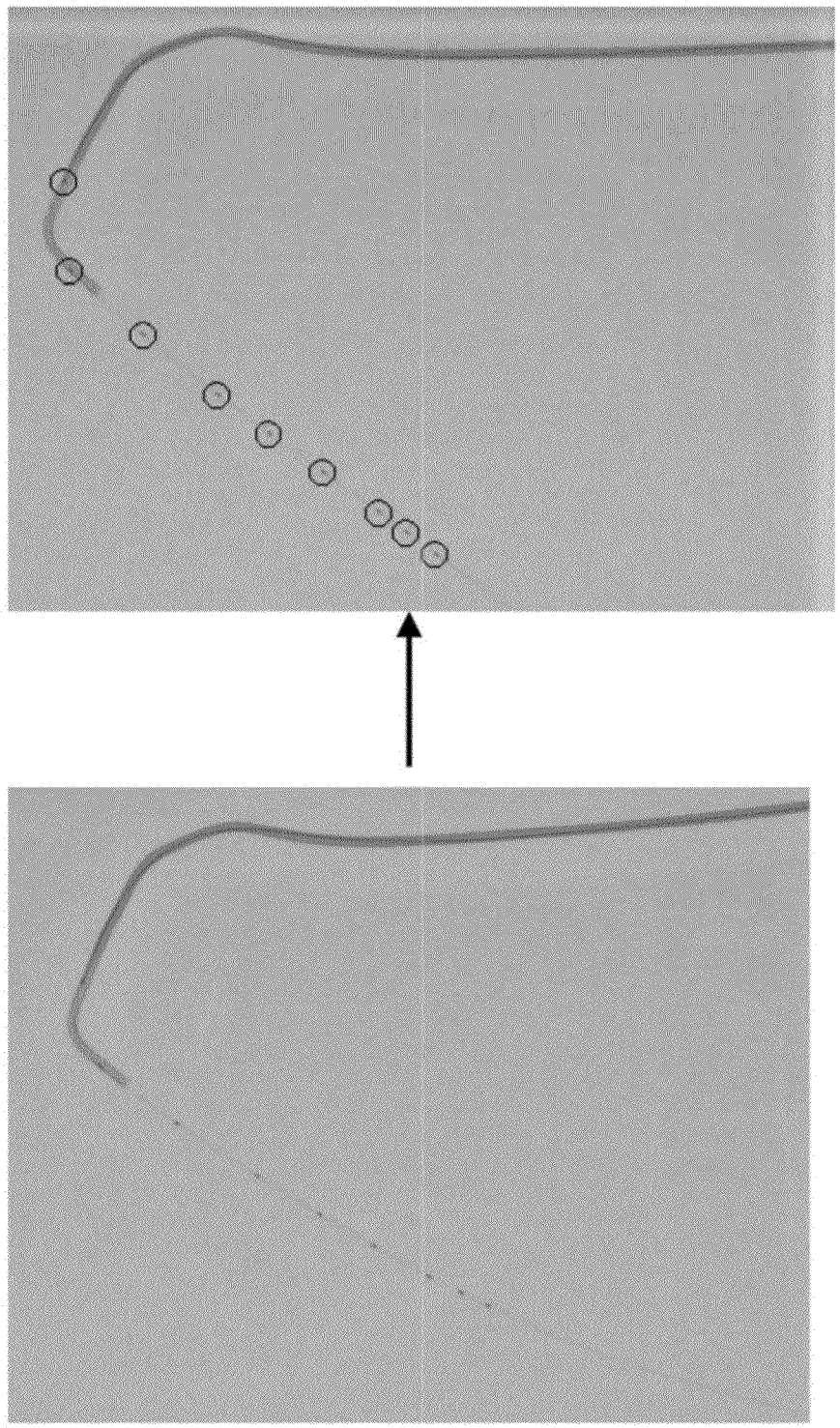
FIG 38A: Identification of markers on a guidewire

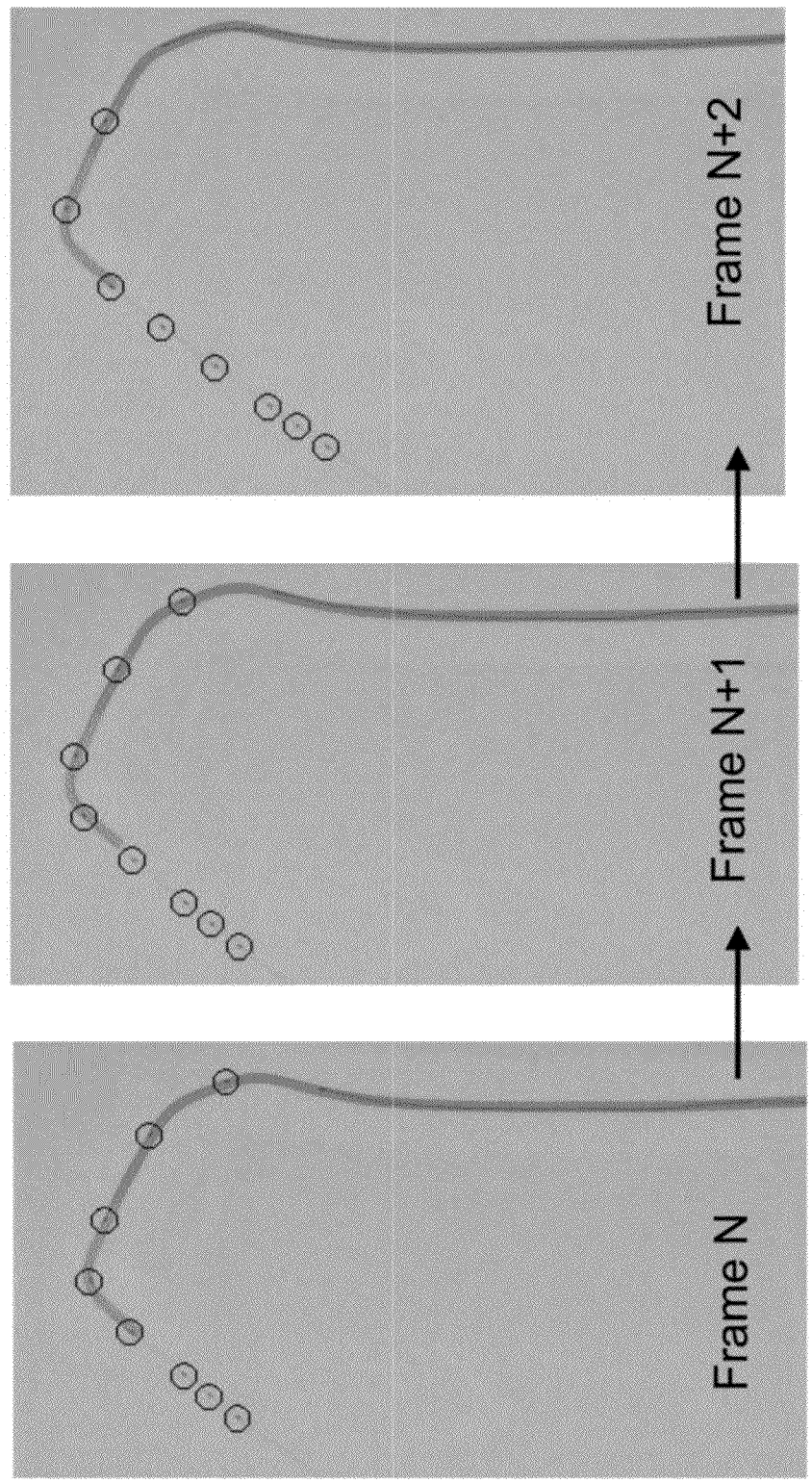
FIG 38B : Tracking of markers across frames

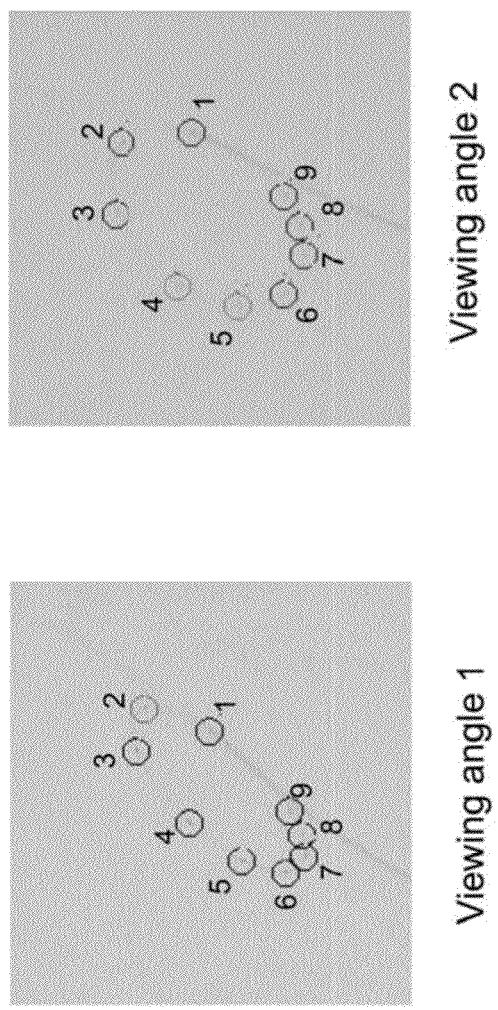
FIG 38C: Change in relative spacing of electrodes due to viewing angle

METHODS AND SYSTEMS FOR DETERMINING VASCULAR BODILY LUMEN INFORMATION AND GUIDING MEDICAL DEVICES

CROSS-REFERENCE TO RELATED APPLICATIONS

This application is a continuation of U.S. patent application Ser. No. 13/305,610 filed Nov. 28, 2011, now U.S. Pat. No. 8,374,689 issued Feb. 12, 2013, which is a continuation of U.S. patent application Ser. No. 13/159,298 filed Jun. 13, 2011, which claims the benefit of U.S. Provisional Patent Application No. 61/383,744, filed Sep. 17, 2010 to Gopinathan, and also claims the benefit of foreign priority of Indian Provisional Patent Application No. 1636/CHE/2010, filed Jun. 13, 2010 to Gopinathan et al., both entitled "Systems and Methods for Measurements of Lumen Parameters", the disclosures of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The invention generally relates to methods and systems useful for medical procedures, and more specifically for determining vascular bodily lumen information and guiding medical devices.

BACKGROUND

To investigate the health of vessels or organs in the human body (e.g. cardiac vessels), it can be important to be able to measure certain internal characteristics or parameters of those vessels or organs, which can provide details related to cardiac diseases and ailments so that appropriate treatment can be performed. Traditional methods for measuring dimensions of vessels or organs include intravascular ultrasound ("IVUS") or optical coherence tomography ("OCT"). In both cases, a source of energy (ultrasound or coherent light) and a scattering sensor (for ultrasound waves or light) are mounted on a catheter and rotated along the axis of the body lumen in order to scan the inside of the lumen and map out its profile, revealing its cross-sectional area. These methods, however, are either very expensive and % or are cumbersome. For example, the use of IVUS requires advancing the ultrasound catheter to a target area, such as a lumen, obtaining the information, removing the catheter, combining the information obtained using the catheter with an angiogram to provide parameters about the vessel, then proceeding with a medical procedure such as, for example without limitation, a stent delivery procedure. In addition to the costs and time disadvantages, these procedures are also inconvenient to the patient.

Electrode-based interventional instruments have been explored as alternatives to IVUS and OCT techniques. Some approaches have used catheters with two electrodes disposed thereon for determining the cross-sectional area of a blood vessel. In use, the catheter is advanced through the blood vessel to a measurement site, and an AC voltage is applied to the electrodes, producing a current through the blood within the vessel. The impedance is measured. A fluid is then injected into the lumen to replace the blood with the fluid, and a second impedance measurement is taken. The multiple impedance measurements are then used to determine the cross-sectional area of the blood vessel between the electrodes. In order to use these catheters in conjunction with an angioplasty procedure, the catheter is first advanced to the treatment site to perform a measurement of the vessel cross-section. The measurement device is then withdrawn and a balloon catheter is advanced to the obstructed site in order to perform the dilatation. Since both the measurement device and the dilatation catheter can be difficult to advance to the obstructed site, multiple device exchanges have to be made adding more time and complexity to the procedure.

A dimension-sensitive angioplasty catheter having an inflatable balloon and a plurality of vessel-measuring electrodes has also been described. The electrodes are mounted on the surface of the catheter tube and are individually connected to the proximal end of the catheter. The catheter also includes an inelastic balloon. The balloon is adapted to be inflated through the introduction of a suitable fluid into the lumen of the tubular member to press the stenotic lesion against the vessel wall. One pair of electrodes is selected for connection to the output of an oscillator, and a second pair of electrodes is selected for sensing a signal that results from conduction through the blood in the vessel. The technique requires injection of fluid into the expander with known concentration at the time of making the measurements using the electrodes, thus adding to the complexity of the procedure. The measurement may also need to be timed with the fluid injection creating room for inaccuracies and procedural complexity. The repeatability of measurements may be affected if the injected fluid does not clear out the blood completely in the vessel at the time of the measurements.

A need therefore exists for improved systems and methods for accurately measuring lumen parameters, such as in the cardiac vasculature.

Additionally, typical imaging techniques provide very limited information, especially about blood vessels and the heart. For example, an angiogram, which uses X-Ray imaging modality and a contrast agent injected into the blood vessel, provides a simple two-dimensional snapshot of the blood vessels. These snapshots or images are used to guide a physician during invasive procedures that are needed for a variety of treatments related to coronary conditions. For example, stent deployment to unblock an artery involves introducing a guide wire and a stent delivery catheter along the aorta to the point of the expected block, and the stent is subsequently deployed. This procedure relies heavily on the skill of the physician operating the devices. Typically, the blood vessel can be tortuous and have turns that may not be evident in a 2-D snapshot. The operators rely on their experience and make educated estimations based on the 2-D images to position the stent before deploying it. This can lead to inaccurate placements and hence less than ideal treatment. To get more accurate positional information it may be useful to obtain a three-dimensional rendering of the lumen trajectory.

Some approaches have attempted to generate three-dimensional ("3D") images of flow structures and their flow lumen using ultrasound technology. For example, some approaches have used multiple 2D slices to generate a 3D image. These techniques are specific to ultrasound imaging techniques, and hence require additional equipment to achieve the outcome.

Some approaches use a method of obtaining at least two complementary images to differentiate the structures and the functions in the region such that image segmentation algorithms and user interactive editing tools can be applied to obtain 3D spatial relations of the components in the region. At least two complementary methods of imaging can be used (e.g., CT and MRI) from which two images are obtained based on identifying existing known anatomical features. The two images then are used together to form a high resolution 3D image.

Some approaches use a method for reconstructing 3D data records from endo-lumen 2D section images of a hollow channel, especially a blood vessel, using an image providing an endo-lumen instrument such as a catheter. 2D images of the hollow channel are prepared and by considering a known relative displacement position of the instrument in the hollow channel for each 2D sectional image a 3D image data record is reconstructed by computer from the image data of the 2D sectional images. The described technique requires multiple 2-D images for a single section of the hollow channel.

Some approaches use an instrument that is moved in a lumen at a defined speed over a defined distance. The approaches intraluminally record 2D images and create a 3D image.

Known techniques require multiple images be made available to obtain a 3D lumen assessment and visualization. Further, in some instances, to obtain lumen trajectory in a 3D volume, complete procedural changes may be necessary, which may not be conducive for adaptation with existing techniques. Also, the imaging procedures described may be cumbersome and complex, and consequently, the medical procedure requires modification to accommodate the imaging procedure, which sometimes is impractical. There are still needs for methods and devices that can provide 3D trajectory of the blood vessel accurately and in a reasonable amount of time to enable a skilled operator to perform intricate invasive procedures with greater confidence.

Imaging vascular lumens is, in general, performed using several types of endo-lumen instruments, such as intra Vascular Ultrasound ("IVUS"), Optical Coherance Tomography ("OCT"), Near Infrared spectroscopes (NIR), and other lumen measurement instruments. Typically these endo-lumen measuring techniques provide important parametric information that aids a practitioner in clinical decision making. For example, an IVUS catheter is used to image the lumen and determine the parameters such as Cross Sectional Area ("CSA") of lumen. The practitioner uses this information to make clinical decisions when, for example, determining an appropriate size of a stent to be delivered in the subject.

This parametric information is not, however, co-registered with the imaging modality used, for example, an X-Ray modality. The corresponding positions where the parameters were measured are not preserved for further use. The physician has to estimate and guide the therapy endo-luminal devices to the points of interest (such as areas of minimum cross-sectional area where a stent is to be deployed).

There have been efforts to fuse images obtained from two or more imaging modalities to locate the position of the endo-lumen instruments vis-à-vis the image of the heart or the artery. In this respect, the focus so far has been to be able to reconstruct a 3D image of the lumen or create a guidance system by using two or more imaging modalities. However, none of these applications address the co-registering of parametric information with the positional information of the endo-lumen instruments.

US 2011/0019892 provides a method for visually supporting an electrophysiological catheter application. An electroanatomical 3D mapping data of a region of interest in the heart is visualized. A 3D image data of the region of interest is captured before the catheter application. A 3D surface profile of objects in the region of interest is extracted from the 3D image data by segmentation. The electroanatomical 3D mapping data and 3D image data forming at least the 3D surface profile is assigned by registration and visualized by superimposing on one another. Characteristic parameters are measured for catheter guidance during the catheter application. The characteristic parameters are compared with at least one predefined threshold value and regulation data for catheter guidance is generated as a function of the comparison result. The regulation data is integrally displayed and represented in the superimposed visualization. The technique described herein presents complexity in terms of first having a 3D map of a region of interest, then obtaining 3D image of region of interest, then segmenting the 3D image to obtain a 3D profile of region of interest and then superimposing on the 3D map. The characteristic parameters are obtained separately by use of a catheter. A threshold value is used to compare with the characteristic parameter and then regulation data for catheter guidance is obtained and displayed. The technique is complex and uses threshold value to provide some regulation data for catheter guidance. The technique, however, fails to co-register the parametric information with the positional information for accurate guidance for medical procedures.

US 2009/0124915 describes a method for guidance to an operator to position electrodes upon a segmented heart model ("SGM"). The SGM is included in a map panel on a display screen. A catheter advanced into a beating heart supports one or more electrodes. During a single beat of the heart, an image is obtained with darkened portions corresponding to locations of the electrodes. The image is presented in the same map panel as the SGM. The current location of the electrodes is confirmed relative to the SGM, either manually or through automated software algorithms. Electrophysical (EP) data is captured that represents electrophysiological signals of the beating heart at the current location for each of the electrodes. A signal processing algorithm is applied to the captured EP data in view of the confirmed current location of the electrodes to result in a calculation that is mapped at the confirmed location of the electrodes. This technique uses a modeling approach where the catheter is tracked through fluoroscopy guidance and imaged, and the tracked image is used to determine the position of catheter electrodes on the previously selected model for the heart. The corresponding EP data is then mapped across the locations on the model. The technique provides both computational complexity and again uses a pre-selected model for registering the EP data. Mapping on a pre-selected model can lead to errors as the heart is in dynamic motion at any given time and the model may not represent the current state for the images heart.

As mentioned herein above, the diagnostic devices (IVUS, OCT, NIR, other lumen assessment devices) used in the vascular spaces (coronary, peripheral, renal, abdominal aorta, neurovascular, etc.) provide diagnostic parameters but do not integrate this information with the position of the devices with respect to a reference so that other diagnostic or therapeutic devices can be guided to the region of interest. Therefore there is continued need in the art to assist the medical practitioner in providing relevant information leading to a more effective therapy.

SUMMARY

One aspect of the disclosure is a method of determining information about a vascular bodily lumen, comprising: generating a multiple-frequency electrical signal at a plurality of frequencies; delivering the multiple frequency electrical signal to a plurality of excitation elements in the vicinity of the vascular bodily lumen; measuring an electrical signal from a plurality of sensing elements at least two of the plurality of frequencies in response to the delivered signal; and determining a lumen dimension using the measured electrical signal at the at least two frequencies.

In some embodiments the measuring step comprises measuring voltages across the plurality of sensing elements at the at least two of the plurality of frequencies. The measuring step can include measuring voltages across the plurality of sensing elements at each of the plurality of frequencies. Determining the lumen dimension can comprise converting the voltages to one or more lumen dimensions.

In some embodiments determining a lumen dimension comprises determining a lumen cross sectional area using the electrical signal at least two of the plurality of frequencies. Determining a lumen cross sectional area can comprise determining a plurality of cross sectional areas. The method can further comprise moving the plurality of excitation elements within the vascular bodily lumen while determining the plurality of cross sectional areas. Determining a cross sectional area can comprise determining a cross sectional profile that comprises a plurality of cross sectional areas at various locations along the length of the vascular bodily lumen. The measuring step can consist of making a single set of measurements simultaneously. The method can further comprise determining a minimum lumen cross sectional area and a reference lumen cross sectional area, and can further comprise identifying the region of blockage.

In some embodiments the method does not include injecting a fluid into the vascular bodily lumen.

In some embodiments the measuring step comprises measuring the electrical signals at the at least two frequencies simultaneously.

In some embodiments the excitation elements also perform the function of the sensing elements.

In some embodiments determining the lumen dimension comprises iteratively comparing the measured electrical signal with a modeled electrical signal to determine the lumen dimension. The comparing step can include comparing a measured voltage with a modeled voltage. The modeled voltage can be based on a modeled lumen dimension. The modeled lumen dimension can be a lumen cross sectional area.

In some embodiments the comparing step comprises comparing the measured electrical signal with an electrical signal from a look-up table. The electrical signal from the look-up table can be a voltage.

In some embodiments generating a multiple frequency sequence pulse comprises generating a multiple-frequency sequence pulse having a predetermined peak to root-to-mean-square (rms) ratio. The ratio can be about 1 and about 2, such as about 1.4, or about 1.

One aspect of the disclosure is a method of determining information about a vascular bodily lumen, comprising: generating an electrical signal; delivering the electrical signal to a plurality of excitation elements in the vicinity of the vascular bodily lumen; measuring a responsive electrical signal from a plurality of sensing elements in response to the delivered electrical signal; and determining a lumen dimension, wherein determining the lumen dimension does not include measuring a second responsive electrical signal.

In some embodiments measuring the responsive electrical signal comprises measuring a plurality of responsive signals, such as voltages at a plurality of frequencies. Determining the lumen dimension can comprise converting the voltages to one or more lumen dimensions. Measuring the responsive signals at the plurality of frequencies can occur simultaneously.

In some embodiments determining a lumen dimension comprises determining a lumen cross sectional area. Determining a lumen cross sectional area can comprise determining a plurality of cross sectional areas. The method can further comprise moving the plurality of excitation elements within the vascular bodily lumen while determining the plurality of cross sectional areas. Determining a cross sectional area can comprise determining a cross sectional profile that comprises a plurality of cross sectional areas at various locations along the length of the vascular bodily lumen.

In some embodiments the measuring step consists of making a single set of measurements simultaneously.

In some embodiments the method further comprises determining a minimum lumen cross sectional area and a reference lumen cross sectional area. The method can further comprise identifying the region of blockage.

In some embodiments measuring the responsive signal does not include replacing a volume of blood with a fluid.

In some embodiments determining the lumen dimension comprises iteratively comparing the measured electrical signal with a modeled electrical signal to determine the lumen dimension. The comparing step can comprise comparing a measured voltage with a modeled voltage. The modeled voltage can be based on a modeled lumen dimension. The modeled lumen dimension can be a lumen cross sectional area. The comparing step can comprise comparing the measured electrical signal with an electrical signal from a look-up table. The electrical signal from the look-up table can be a voltage.

One aspect of the disclosure is a method of determining information about a vascular bodily lumen, comprising: generating an electrical signal; delivering the electrical signal to a plurality of excitation elements in the vicinity of the vascular bodily lumen; measuring a plurality of responsive electrical signals from a plurality of sensing elements in response to the delivered electrical signal, wherein a first of the plurality of sensing elements is not equally spaced from second and third sensing elements; and determining a lumen dimension based on the measured electrical signals.

In some embodiments the first sensing element is disposed axially between the second and third sensing elements. In some embodiments the delivering step comprises delivering the electrical signal to the second and third sensing elements. In some embodiments the delivering step comprises delivering a multiple frequency electrical signal to the plurality of excitation elements. The measuring step comprises measuring voltages across the plurality of sensing elements at the at least two of the plurality of frequencies. Determining a lumen dimension can comprise converting the voltages to one or more lumen dimensions. Determining a lumen dimension can comprise determining a lumen cross sectional area using the measured plurality of electrical signals. Determining a lumen cross sectional area can comprise determining a plurality of cross sectional areas. The method can comprise determining a minimum lumen cross sectional area and a reference lumen cross sectional area, and may include identifying a region of blockage.

One aspect of the disclosure is a medical device adapted to determine information about a vascular bodily lumen, comprising: an elongate device; and a plurality of excitation elements and a plurality of sensing elements disposed on the elongate device, wherein a first of the plurality of sensing elements is not equally spaced from second and third sensing elements.

In some embodiments the first sensing element is disposed axially between the second and third sensing elements on the elongate device. In some embodiments the second and third sensing elements are also first and second excitation elements. In some embodiments the elongate device is a guidewire, and wherein the excitation elements and sensing elements are electrodes. In some embodiments the elongate device is an angioplasty balloon catheter and wherein the excitation elements and the sensing elements are electrodes. In some embodiments wherein the elongate device is a stent delivery catheter, and wherein the excitation elements and the sensing elements are electrodes.

One aspect of the disclosure is a method of providing an elongate medical device adapted to determine information about a vascular bodily lumen, comprising: selecting an elongate device comprising first and second electrical excitation elements thereon, wherein the first and second excitation elements are spaced at a distance that is within an estimated range of the vascular bodily lumen diameter; and positioning the elongate device in the vascular bodily lumen.

In some embodiments the method further comprises exciting the first and second electrical elements with an excitation source. The elongate medical device can have a plurality of sensing elements thereon, the method further comprising measuring a responsive electrical signal from the plurality of sensing elements in response to the excitation.

One aspect of the disclosure is a method for determining a lumen trajectory of a subject in a 3D volume comprising: positioning a plurality of markers in vivo in a lumen, wherein each marker is characterized by an original identity; obtaining an image of the plurality of markers; processing the image to determine an observed identity of at least a subset of the plurality of markers and an observed spacing between at least two of the plurality of markers: determining a position of at least a subset of markers in a 3D volume based on the observed identity, the observed spacing, and the original identity of the subset of the plurality of markers; and determining the lumen trajectory in a 3D volume based on the position of each marker.

In some embodiments the method further comprises traversing the plurality of markers through the lumen; tracking the observed identity, and the observed spacing at different positions; determining a plurality of positions of each marker in a 3D space based on the observed identity, the observed spacing and the original identity of each of the plurality of markers; and determining the lumen trajectory in a 3D volume in a 3D volume based on the plurality of positions of each marker. The method can further comprise mapping the observed identity at different phases of heart; and determining a phase-dependent lumen trajectory in a 3D volume. The method can further comprise determining a current position of each marker in the 3D space by determining a current observed identity for each marker, and superimposing the current observed identity on the phase dependent lumen trajectory in a 3D volume. The method can further comprise placing a reference patch on the subject, such as using the patch to determine a change in the subject's position, or to determine the position of each marker. The method can further comprise using the reference patch to determine the viewing angle of the imaging system. The method can further comprise using the reference patch to determine the calibration factor. The plurality of markers can comprise at least two spaced apart electrodes.

One aspect of the disclosure is a lumen trajectory system comprising: a plurality of markers disposed at predefined locations on an endo-lumen instrument, the instrument configured to be placed in vivo in a vascular bodily lumen; an imaging component adapted to image the endo-lumen instrument in the lumen; and a processing component adapted to process the image to determine at least an observed identity for at least a subset of the plurality of markers and an observed spacing between at least a subset of the markers from the plurality of markers, and to determine a position of at least a subset of the markers in a 3D space that defines the lumen based on the observed identity, the observed spacing, and an original identity of the subset of the plurality of markers, to determine the lumen trajectory in a 3D volume in a 3D volume based on the position of each marker.

In some embodiments the system further comprises a tracking module to track a traverse movement of the endo-lumen instrument in the lumen.

In some embodiments the system further comprises a synchronous phase imaging device to map the observed identity at different phases of heart, and to determine a phase dependent lumen trajectory in a 3D volume in a 3D volume. The processing means can be is configured to determine a current position of at least a subset of markers in the 3D space by determining a current observed identify for at least a subset of markers, and superimposing the current observed identity on the phase dependent lumen trajectory in a 3D volume.

In some embodiments the system further comprises a reference patch configured to be placed on a subject having the lumen. The reference patch can be used to determine a change in subject position. The reference patch can be used to determine the position of each marker. The reference patch can comprise a plurality of calibration electrodes arranged in a predetermined pattern, such as a grid. The reference patch can be placed at a pre-determined orientation with respect to a plane of imaging of the imaging means. A plurality of markers can comprise at least two spaced apart electrodes.

One aspect of the disclosure is a lumen translation measurement system comprising: a plurality of markers disposed at a plurality of predefined locations on an endo-lumen instrument, the instrument configured to be positioned in-vivo in a vascular bodily lumen: an imaging component adapted to image the positions of the plurality of markers on the endo-lumen instrument as it translates through the lumen and adapted to create a plurality of image frames corresponding to the positions of the plurality of markers on the endo-lumen instrument; and a processing component adapted to process the plurality of image frames to determine the amount of translation of the endolumen instrument between the image frames.

One aspect of the disclosure is a method of determining axial translation of a medical device within a vascular bodily lumen, comprising: imaging first and second markers on an elongate medical device within a vascular bodily lumen; imaging the axial translation of the first and second markers within a vascular bodily lumen in a plurality of image frames: and processing the plurality of images frame to determine the axial translation of the medical device.

One aspect of the disclosure is a method for obtaining a phase dependent 3D lumen trajectory: traversing a plurality of markers placed in vivo in a lumen, wherein each marker is characterized by an original identity; obtaining an image of the plurality of markers; processing the image to determine at least an observed identity for each of the plurality of markers and an observed spacing between at least two markers from the plurality of markers; tracking the observed identity, and the observed spacing at different positions: mapping the observed identity at different phases of heart; and determining a phase dependent lumen trajectory in a 3D volume based on the phases of heart and the observed identity and observed spacings.

One aspect of the disclosure is a method for obtaining reference information for diagnostic guidance for an in vivo medical procedure, wherein the method comprises: providing lumen trajectory information corresponding to a lumen and parametric information corresponding to the lumen; and combining the lumen trajectory information with the parametric information to obtain the reference information for diagnostic guidance.

In some embodiments the lumen trajectory information is selected from the group consisting of a 2D image and a 3D image. In some embodiments the parametric information is at least one pressure, blood flow rate, cross sectional area, and combinations thereof. The lumen trajectory information and parametric information can be phase synchronized. The phase synchronization can be achieved using ECG gating. The trajectory information and parametric information can be synchronized in time. The synchronization in time can be achieved using a common clock.

In some embodiments the reference information is represented as at least one of a reference image or a reference table or a graphical representation.

In some embodiments the reference information further comprises areas of diagnostic interest marked.

In some embodiments the method further comprises displaying the reference information on a graphical user interface.

In some embodiments the lumen trajectory information is obtained from at least one of an MRI, X ray, ECG, fluoroscopy, microscopy, ultrasound imaging and combinations thereof.

In some embodiments the parametric information is obtained from at least one of an microscopy, ultrasound, Intra Vascular Ultrasound (IVUS), Near Infrared spectroscopy (NIR), Optical Coherence Tomography (OCT), vascular optical camera devices, and combinations thereof.

In some embodiments the parametric information includes a cross sectional area obtained using a multiple frequency excitation signal and simultaneously measuring a responsive signal at each of the plurality of frequencies.

In some embodiments the method further comprises guiding an endo-lumen instrument in a lumen using the reference information.

One aspect of the disclosure is a method for guiding an endo-lumen instrument in a lumen to a region of interest, the method comprising: placing the endo-lumen instrument in a lumen; providing lumen trajectory information for the lumen; providing parametric information for the lumen; combining the lumen trajectory information and the parametric information to generate reference information for the lumen; imaging the endo-lumen instrument in the lumen to provide a endo-lumen instrument image; correlating the endo-lumen instrument image onto the reference information; and guiding the endo-lumen instrument to the region of interest.

In some embodiments a fixed reference for a field of view is used. The fixed reference for the field of view can be obtained by attaching a radio opaque marker patch on a subject. The fixed reference for the field of view can be obtained by attaching a radio opaque marker patch on an object. The fixed reference for the field of view can be obtained by an initial marking of at least one anatomic location in the lumen trajectory information. The fixed reference for the field of view can be obtained by using a set of co-ordinates of an imaging system.

In some embodiments the lumen trajectory information is a 2D image or a 3D image.

In some embodiments the parametric information can be at least one pressure, blood flow rate, cross sectional area, and combinations thereof.

In some embodiments the lumen trajectory information and parametric information are phase synchronized. The phase synchronization is achieved using ECG gating. The trajectory information and parametric information can be synchronized in time. The synchronization in time can be achieved using a common clock.

In some embodiments the reference information is represented as at least one of a reference image or a reference table or a graphical representation.

In some embodiments the parametric information is obtained using the endo-lumen instrument.

In some embodiments the lumen trajectory information is obtained from at least one of an MRI, X ray, ECG, fluoroscopy, microscopy, ultrasound and combinations thereof. The parametric information can be obtained from at least one of microscopy, ultrasound, Intra Vascular Ultrasound (IVUS), Near Infrared spectroscopy (NIR), Optical Coherence Tomography (OCT), vascular optical camera devices, and combinations thereof.

The parametric information can includes a cross sectional area obtained using a multiple frequency excitation signal and simultaneously measuring a responsive signal at each of the plurality of frequencies.

One aspect of the disclosure is a diagnostic element comprising: at least two spaced apart sets of electrodes configured to be placed in vivo proximal to a volume of interest in a cardiac vasculature, wherein at least a first set of electrodes from the at least two spaced apart sets of electrodes is configured to receive an input excitation from an excitation source, and at least a second set of electrodes from the at least two spaced apart sets of electrodes is configured to receive an response voltage signal from the volume of interest and transmit the response voltage signal to a measurement device.

In some embodiments the diagnostic element further comprises a support wire comprising a distal end and a proximal end, wherein the at least two spaced apart sets of electrodes are positioned at a distal end of the support wire, and the excitation source and the measurement device are positioned at a proximal end of the support wire. The distal end can be a helically wound coil. The at least two spaced apart sets of electrodes can be placed along a length of the support wire at predetermined positions. The support wire can be a single wire. The support wire can comprise a plurality of wire strands spaced apart by an insulating material. The plurality of wire strands can be provided in a configuration selected from the group consisting of a multi-filar winding, one or more braided wires, one or more twisted pairs of wires, and one or more winding twisted pairs of wire. The insulating material can be a polymer.

In some embodiments the measurement device calculates a voltage difference between the at least second set of electrodes, based on output signals received by the measurement device, wherein the output signals are a function of the response voltage signal and wherein the voltage difference is a function of a lumen dimension of the volume of interest. In some embodiments the voltage difference is based on spatial diversity of the at least two electrodes. The voltage difference can be based on frequency diversity of the input excitation and the response signal. The voltage difference can be based on tissue diversity of the vasculature. The measurement device can be coupled to a display device to display the lumen dimension.

In some embodiments at least one of the at least two electrodes is a distributed electrode. In some embodiments at least one of the at least two spaced apart electrodes comprises one or more electrodes. The one or more electrodes can be arranged in at least one of a straight line configuration, a staggered configuration, or a spatial configuration.

In some embodiments a catheter comprises the diagnostic element, wherein the catheter is further configured to determine a cross sectional area of an aortic valve and further determine a prosthetic size for a bioprosthetic valve. In some embodiments the diagnostic element is a balloon catheter. The balloon catheter can be further configured to determine a cross sectional area of an aortic valve and further determine a prosthetic size for a bioprosthetic valve. The measurement device can calculates a voltage difference between the second set of electrodes, based on output signals received by the measuring device, wherein the output signals are a function of the response voltage signal and wherein the voltage difference is a function of a balloon dimension of the balloon catheter.

One aspect of the disclosure is an active guide wire comprising: a distal end comprising at least two spaced apart sets of electrodes, wherein the distal end is configured to be placed in vivo proximal to a volume of interest in a vasculature; and a proximal end configured to be coupled to a measurement device and to an excitation source. In some embodiments the distal end is a helically wound coil.

In some embodiments a first set of electrodes from the at least two spaced apart sets of electrodes is used to send an input signal into the volume of interest, and a second set of electrodes from the at least two spaced apart sets of electrodes is used to receive an response voltage signal from the volume of interest. The measurement device can calculate a voltage difference between the second set of electrodes, based on output signals received at the proximal end, wherein the output signals are a function of the response voltage signal, and wherein the voltage difference is a function of a lumen dimension of the volume of interest. The voltage difference can be based on spatial diversity of the at least two electrodes, frequency diversity of the input excitation and the response voltage signal, and/or on tissue diversity of the blood vessel.

In some embodiments the active guide wire is a single wire. The active guide wire can comprise a plurality of wire strands spaced apart by an insulating material. The plurality of wire strands can be provided in a configuration selected from the group consisting of a multi-filar winding, one or more braided wires, one or more twisted pairs of wires, and one or more winding twisted pairs of wire.

One aspect of the disclosure is a diagnostic device for measuring lumen dimensions comprising: a diagnostic element comprising at least two spaced apart sets of electrodes configured to be placed in vive proximal to a volume of interest in a vasculature; an excitation source coupled to a first set of electrodes of the at least two spaced apart sets of electrodes; a measurement device coupled to a second set of electrodes of the at least two spaced apart sets of electrodes; wherein the first set of electrodes from the at least two spaced apart set of electrodes is configured to receive an input excitation from an excitation source, and the second set of electrodes from the at least two spaced apart set of electrodes is configured to receive an response voltage signal from the volume of interest and transmit the response voltage signal to a measurement device.

In some embodiments the device further comprises a processor coupled to the measurement device to calculate a voltage difference between the second set of electrodes, based on output signal received at the proximal end, wherein the output signal is a function of the response voltage signal, and wherein the voltage difference is used to calculate a lumen dimension of the volume of interest. The processor can be an integral component of the measurement device. The processor can be split into two or more levels, wherein at least one of two or more levels resides in a host computer. The device can further comprise a display device coupled to the processor to display the lumen dimension. The display device is configured to display a visual 2D representation of the lumen dimension.

One aspect is a method for calibration for use in measurements from a remotely located multi port network, the method comprising: providing an excitation and measurement entity for exciting the remotely located multi port network and for measuring proximal voltages corresponding to a plurality of distal voltages at the remotely located multi port network; providing a connecting network for connecting the excitation and measurement entity and the remotely located multi port network; providing a plurality of known load networks coupled to the connecting network; measuring a plurality of voltages corresponding to each load of the known load networks; and estimating electrical parameters based on the measured voltages corresponding to the measurement entity and the connecting network, wherein the electrical parameters are used for calibration.

In some embodiments the electrical parameters are at least one of Z parameters, Y parameters, S parameters, H parameters, and G parameters.

In some embodiments each load network from the plurality of network yields at least three voltage measurements. The plurality of load network can provide at least eight load networks.

In some embodiments the remotely located multi port network is a floating network. In some embodiments the method further comprises using the electrical parameters to de-embed the measurements from the remotely located multi port network.

One aspect is a method for measuring a plurality of actual voltages from a remotely located multi port network, the method comprising: providing an excitation and measurement entity for exciting the remotely located multi port network and for measuring a proximal voltages corresponding to a plurality of distal voltages at the remotely located multi port network; providing a connecting network for connecting the excitation and measurement entity and the remotely located multi port network; providing a plurality of electrical parameters as calibration parameters corresponding to the measurement entity and the connecting network; exciting the remotely located multi port network with a known excitation; measuring proximal voltages across at least two pair of ports for the remotely located multiport network; and estimating actual voltages across the at least two pair of ports using the electrical parameters to de-embed the proximal voltages.

In some embodiments the electrical parameters are selected from a group consisting of Z parameters, Y parameters, S parameters, H parameters, and G parameters. In some embodiments the remotely located load network is a floating network. In some embodiments the connecting network comprises a plurality of conductor wires. In some embodiments the remotely located load network comprises at least three distal electrodes placed in vivo in a body lumen. The three distal electrodes can be placed at the distal end of at least an active guide wire or a catheter. The actual voltages can be used to determine one or more lumen dimensions for the body lumen.

One aspect is a method for de-embedding measured distal voltages across at least three electrodes placed in vivo in a body lumen, the method comprising: providing an excitation and measurement entity for exciting the at least three electrodes and for measuring proximal voltages corresponding to a plurality of distal voltages at the at least three electrodes; providing two or more conductors as a connecting network for connecting the excitation and measurement entity and the at least three electrodes, wherein the at least three electrodes are at a distal end of the two or more conductors; providing a plurality of electrical parameters as calibration parameters corresponding to the excitation and measurement entity and the connecting network; exciting the at least three electrodes with a known voltage excitation; measuring proximal voltages across at least two pair of the at least three electrodes; and estimating actual voltages across the at least two pair of the at least three electrodes using the electrical parameters to de-embed the proximal voltages.

In some embodiments the electrical parameters are selected from a group consisting of Z parameters, Y parameters, S parameters, H parameters, and G parameters. The at least three electrodes can be placed at the distal end of at least an active guide wire or a catheter. The actual voltages can be used to determine one or more lumen dimensions for the body lumen.

One aspect is a system for de-embedding measured proximal voltages across at least three electrodes placed in vivo in a body lumen, the system comprising: an excitation and measurement entity for exciting the at least three electrodes and for measuring proximal voltages corresponding to a plurality of distal voltages at the at least three electrodes: two or more conductors configured as a connecting network for connecting the excitation and measurement entity and the at least three electrodes, wherein the at least three electrodes are at a distal end of the two or more conductors; and a processor for estimating a plurality of electrical parameters as calibration parameters corresponding to the excitation and measurement entity and the connecting network, and for estimating actual voltages across the at least two pair of the at least three electrodes using the electrical parameters to de-embed the plurality of proximal voltages. In some embodiments the electrical parameters are selected from a group consisting of Z parameters, Y parameters, S parameters, H parameters, and G parameters. In some embodiments the at least three electrodes are placed at the distal end of at least an active guide wire or a catheter. In some embodiments the actual voltages are used to determine one or more lumen dimensions for the body lumen.

BRIEF DESCRIPTION OF FIGURES

The features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 7A illustrates an exemplary method of determining a lumen dimension.

FIG. 8A illustrates an exemplary method of determining a lumen dimension.

FIG. 8B illustrates an exemplary method of determining a lumen dimension.

FIG. 38a illustrates identification of markers on an elongate medical device such as a guidewire.

FIG. 38b illustrates tracking the markers across a plurality of frames.

FIG. 38c illustrates changing in relative spacing of electrodes due to viewing angles.

DETAILED DESCRIPTION

Figure 1:
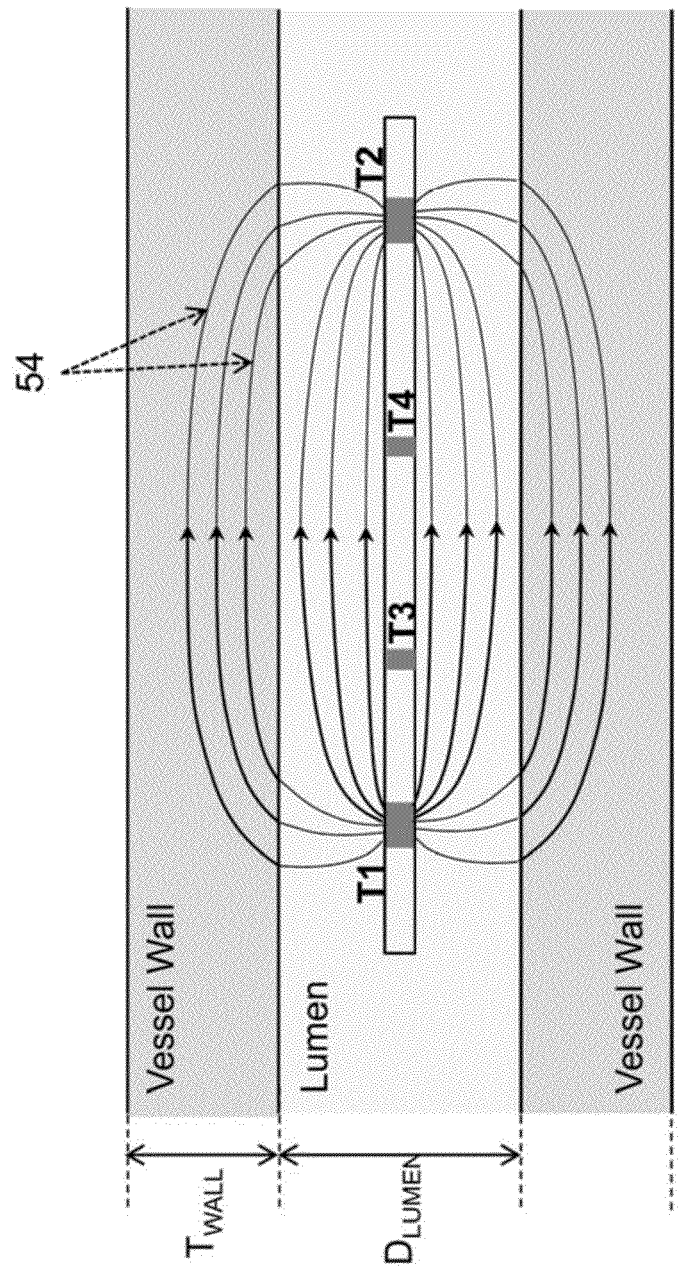
FIG. 1 is a diagrammatic representation of current paths between excitation elements positioned within lumen.

The devices, systems, and methods described herein combine imaging, precise physical measurement and tissue characterization at a smaller footprint and at lower cost compared to other standard diagnostic techniques such as, without limitation, Angiography, IVUS, Optical Coherance Tomography (OCT), Near Infrared Spectroscopy (NIR) and FFR ("fractional-flow reserve"). The techniques described herein can further uncover more anatomical details than some other diagnostic approaches and provide several advantages in a variety of uses.

The disclosure herein provides devices, systems, and methods for determining vascular bodily lumen or vessel dimensions, such as a cross-sectional area. Vascular bodily lumen as described herein implies a bodily lumen of the circulatory system like an artery or vein having blood as a fluid flowing in the lumen and generally refers to blood vessels. "Dimension" as used herein includes, without limitation, cross sectional area, diameter, radius, major/minor axis, and any derivatives thereof. Aspects of the disclosure can be applied as standalone systems or methods, or as part of a greater diagnostic or therapeutic device or procedure. It shall be understood that aspects of the disclosure can be appreciated individually, collectively, or in combination with each other. Features described in one or more embodiments can be incorporated into other embodiments unless the disclosure specifically says otherwise.

In some embodiments the systems and methods can determine cross sectional area to determine where the cross sectional area is at a minimum in the lumen, and hence identify where a blockage exists. In some embodiments the disclosure provides for accurate placement and dilation of a stent within the blocked region of the vasculature, with minimal or no need to use additional diagnostic tools to determine and confirm stent dimensional choices, placement, coverage, and proper apposition to the vessel wall. The embodiments herein can address geographic misplacement of stents in arteries, other blood vessels, or other lumens, since angiograms can result in inaccurate and subjective visual estimates. Geographic misplacement can include longitudinal misses and/or axial misses. In a longitudinal misplacement, the stent is placed too far distally or too far proximally, leaving uncovered plaque in some instances. In other instances the stent length may be insufficient to cover the lesion length, also leaving uncovered plaque. Additionally, post dilation with a balloon can cause injury to the vessel at the edge of a stent if the balloon is inflated too far proximally or too far distally. In an axial miss, the stent to artery ratio may be less than 0.9. That is, the stent is not inflated to at least 90% of the desired artery diameter. In another form of axial miss, the stent to artery ratio may be greater than 1.3, meaning that the stent is inflated to over 130% of the desired artery diameter.

In some embodiments, determining lumen parameters such as cross sectional area provides accurate, real-time determination of the location the blockage in the vasculature and also to indicate the dimensions of the inflated balloon or stent. The systems and methods herein can, however, be used for any other suitable procedure in any other suitable portion of the body, such as a TAVI procedure as is described below.

In some embodiments the location of the blockage, or other anatomical regions of interest, can be identified and the movement of other diagnostic devices can be tracked relative to the anatomical region of interest. For example, in some embodiments a blockage is identified and registered with respect to a reference point, such that the movement of a stent catheter can be tracked relative to the location of the blockage. Other known methods can be used to identify the anatomical region of interest.

A first aspect of the disclosure determines vascular bodily lumen information. These embodiments involve passing electric current between excitation elements positioned within a vascular bodily lumen or organ ("lumen or organ" is generally referred to herein simply as "lumen") and measure one or more response electrical signals, also referred as response signals, using a plurality of sensors, or sensing elements, within the vascular bodily lumen to determine one or more lumen parameters, such as one or more cross-sectional areas of the lumen. In exemplary methods, the excitation signals are multiple frequency signals, and the response signals are response voltages simultaneously measured at multiple frequencies (this is generally referred to herein as "frequency diversity"). The measured response signals across the multiple frequencies are then used to determine one or more lumen parameters, such as one or more cross-sectional areas. In some embodiments the excitation elements, disposed on an elongate medical device, are not equidistantly spaced from one another along the device, and this concept is generally referred to herein as "spatial diversity."

As used herein, the following terms, without limitation, may be used interchangeably to refer to the same or similar devices: "elongate medical device," "diagnostic device," "delivery device," "guidewire." "catheter."

Figure 2:
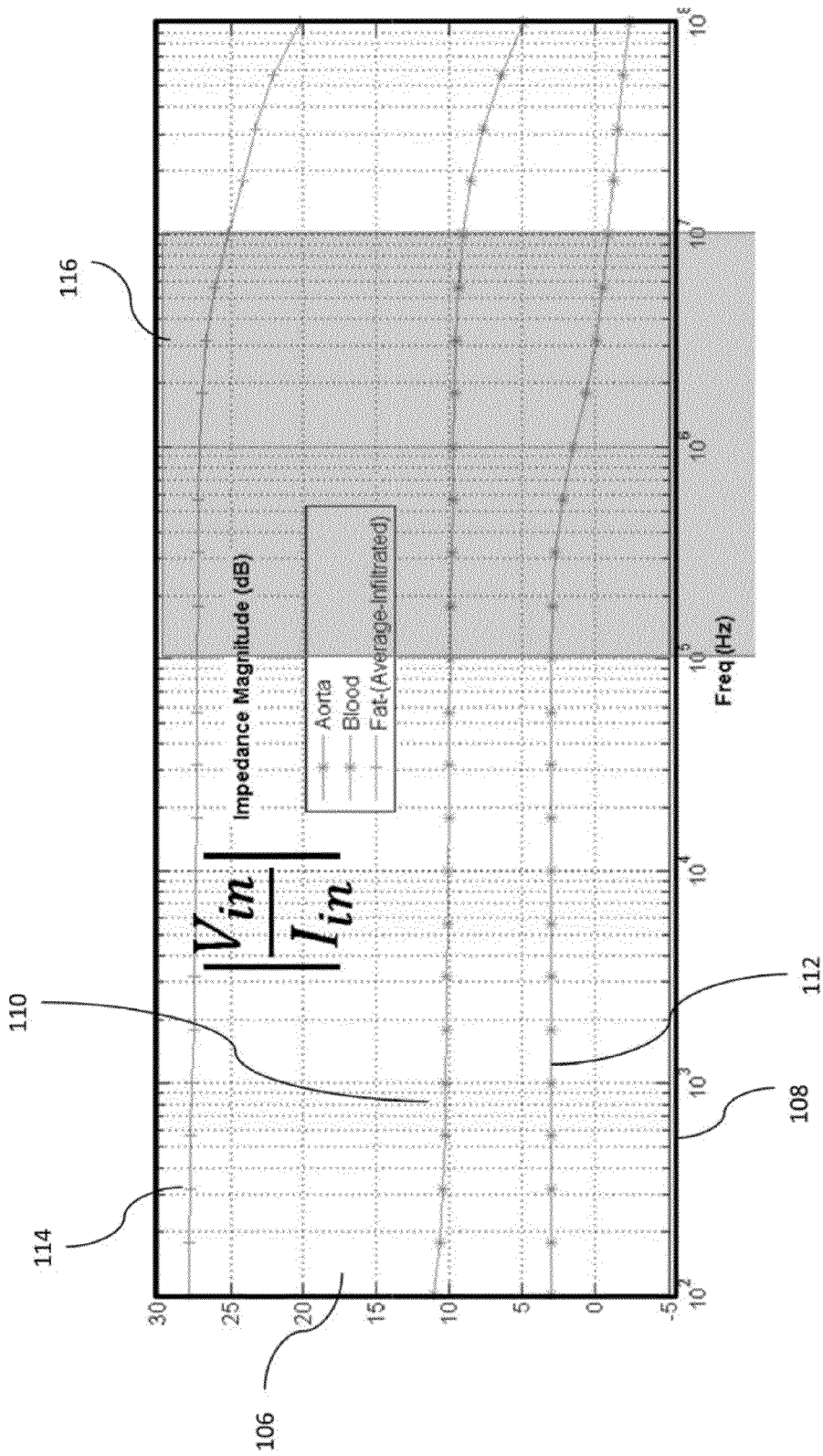
FIG. 2 is a graphical representation showing the magnitude of specific impedance for various tissue types over a range of frequencies.

The methods herein exploit distinctive frequency-dependent electrical properties of various bodily elements such as blood, vessel wall, fatty tissue, calcified tissue, etc. to determine lumen parameters. FIG. 2 is a graphical representation of impedance magnitude 106 for various tissue types over a range of frequencies 108. Impedance magnitude (absolute value of Vin/Iin measured in dB) versus frequency (Hz) is provided for aorta 110, blood 112, and fat (average infiltrated) 114. Vin represents voltage and Iin represents current. The plots of impedance magnitude (absolute value of Vin/Iin measured in dB) for blood, tissue (aortic vessel) and fat shown indicate that when an excitation (e.g., a sinusoidal current (AC), or any other waveform) at different frequencies is applied in series across the volume of interest (1 cubic millimeter, for example), the impedance magnitude varies depending on the type of bodily material that occupies that volume.

Figure 3:
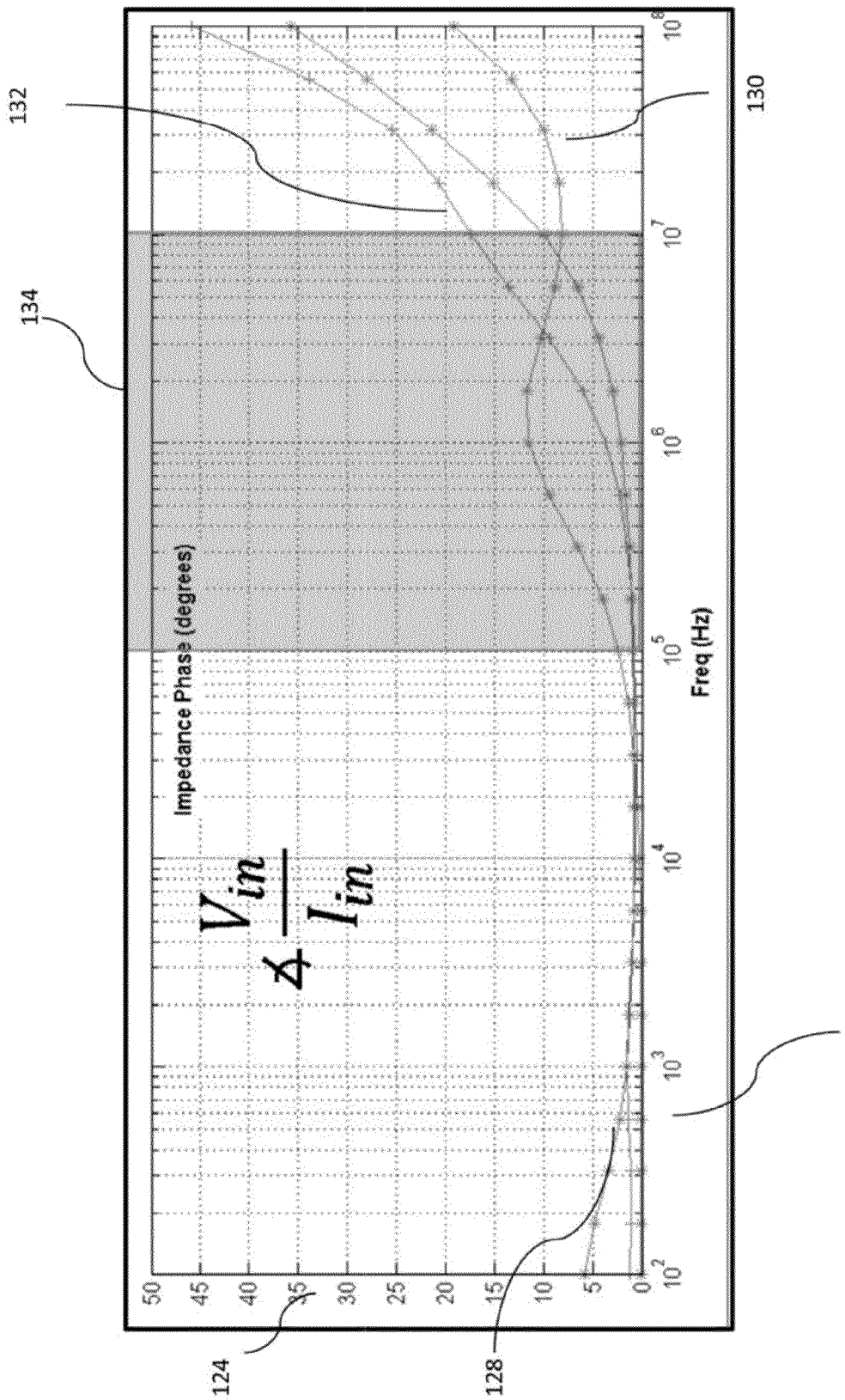
FIG. 3 is a graphical representation showing phase of specific impedance for various tissue types over a range of frequencies.

FIG. 3 is a graphical representation of an example of impedance phase 124 (in degrees) for various tissue types over a range of frequencies 126. Line 128 represents the impedance phase (angle of Vin/Iin measured in degrees) of tissue (e.g. aortic vessel) across a frequency range of 100 Hz to 100 MHz; line 130 represents impedance phase (angle of Vin/Iin measured in degrees) of blood across a frequency range; line 132 represents impedance phase (angle of Vin/Iin measured in degrees) of fat across a frequency range. Vin represents voltage and Iin represents current. The plots of impedance phase (angle of Vin/Iin measured in degrees) for blood, tissue and fat shown indicate that when an excitation (e.g., a sinusoidal current (AC), or any other waveform as described elsewhere) at different frequencies is applied in series across the volume of interest (1 cubic millimeter, for example), the impedance phase depends on the type of bodily material that occupies that volume.

The electrical excitation sequence used to excite the excitation elements is designed so as to simultaneously excite the lumen with multiple frequencies spanning a suitable frequency range. The frequency range is preferably chosen where the various bodily elements (e.g., blood, fat, plaque, tissue) show distinctively different frequency dependent electrical characteristics, such as in the range shown in FIG. 2 and FIG. 3. These differences lead to unique characteristics in the measured frequency-dependent signals, which help in accurate assessment of lumen dimension.

FIG. 1 illustrates a representation of an exemplary elongate medical device with electrodes T1-T4 within a vascular bodily lumen. Current is shown passing between excitation electrodes T1 and T2 along current filaments 54. Some of the filaments extend solely through the blood within the lumen, and some pass through both blood and through the vessel wall as shown. It is understood that additional tissue, such as fatty tissue or calcified fatty tissue, can be deposited on the lumen wall such that some filaments pass through one or more of blood, lumen tissue, fatty tissue, calcified fatty tissue, etc. The total electrical current between terminals T1 and T2 is the sum total of all the individual current filaments. Terminals T1, T2, T3 and T4, which are in this embodiment electrodes, are adapted to measure voltages. This provides three unique voltages, V1, V2 and V3 (e.g., the voltage between T1 and T3, between T3 and T4, and between T4 and T2). There are alternate ways of measuring the 3 unique voltages. For example, the terminal T2 could be used as a common reference, and the 3 unique voltages can be measured between T1 and T2, between T3 and T2, and between T4 and T2. This alternate measurement is essentially a linear combination of the previously stated example of measuring V1, V2 and V3, and they carry the same information. The particular method of measuring voltage chosen depends on convenience of implementation and the degree of noise present in each type of measurement.

From FIG. 1, it is evident that the current lines are crowded near the electrode, and fan out away from the electrode. This effectively increases the impedance that is measured between the excitation electrodes (also referred to as two-port impedance). The measured two port impedance would be significantly larger than the impedance determined by the formula used for calculating the resistance or impedance of a cylindrical section of a conducting medium, which is p*L/A (where p is the resistivity of the medium, L is the length of the cylindrical section, and A is the cross-sectional area). In some instances, a value several times greater than the formula impedance was observed. The extra impedance, sometimes called contact impedance or electrode fringe effects, is a function of the geometry of the electrode and the conductivity of the medium in which it is in. Even if the cross-sectional area of the lumen is increased to a very large value, the two-port impedance does not fall below a certain value. To alleviate the effects of contact impedance, a 4-point impedance measurement is used that uses electrodes away from the excitation electrodes and are closer spaced. With reference to FIG. 1, it can be seen that the electrical current filaments are fairly parallel to the axis between electrodes T3 and T4. A 4-point measurement would be a measurement taken between electrodes 13 and T4 with the excitation occurring between the outer electrodes, T1 and T2. This reduces the effect of electrode geometry, but not completely unless the excitation electrodes are placed very far apart. Further, the amount of current passing outside the blood (wall and surrounding tissue) is also influenced by electrode geometry, which cannot be compensated for by the 4 point measurement. Hence the approach followed in the methods herein includes the effects of the geometry of the electrodes in the calculations. The methods do not attempt to determine any impedance, but instead use the electrical voltage distribution at various locations in the region of interest to determine cross-sectional area. These voltage distributions are influenced by both the electrode geometry and the lumen dimensions. By building equivalent electrical models that include electrode geometry, both of these factors are automatically accounted for in the calculation of the cross-sectional area of the lumen, as is described below.

Spatial diversity of excitation electrodes provides for more accurate and robust estimated lumen parameters. With reference to FIG. 1, some current passes through the lumen while some passes through the lumen wall. If the electrodes are spaced close to one another other, most of the current passes through the lumen, while very little of the current passes through the wall. In such a situation, the observed voltages become insensitive to wall boundary, and hence the lumen dimension. On the other hand, if the electrodes are spaced too far apart, most of the current flows through the wall. In this situation, the voltage becomes insensitive in small changes in lumen size. In some embodiments, an optimal spacing exists where approximately half of the current flows through the lumen and the remainder through the wall. This generally leads to the desired sensitivity to lumen dimensional changes. The optimal spacing depends on the lumen dimension and the electrical characteristics of the tissues. As a general rule of thumb, for typical electrical characteristics of tissue, it has been empirically found that the optimal spacing between T1 and T2 is approximately equal to the diameter of the lumen, although the spacings are not so limited. For fixed electrode spacing, the spacing should be optimized for an entire operating range of potential lumen sizes. In this case, the spacing is optimized for a value in the middle of the operating range so that sensitivity is reasonable throughout the operating range. In an alternate method, many sets of electrodes are provided with different spacings between them. One set is chosen for the procedure depending on the expected lumen dimension. Alternatively, the first measurement is done using a default set of electrodes. Based on this measurement, a second set of electrodes is chosen to obtain a more accurate estimate of the lumen dimension.

In the exemplary embodiment in FIG. 1, electrodes T3 and T4 are used solely for measurement. More electrodes are, however, possible. The two shown in FIG. 1 are merely exemplary. The positions of these electrodes are shown roughly uniformly spaced between the excitation electrodes T1 and T2. In alternative embodiments the measurement electrodes can be staggered so that they are not exactly uniformly spaced between T1 and T2. This asymmetry is found to provide additional lumen information. For example, when only one measurement electrode (e.g., T3) is used between T1 and T2, and is placed exactly in between T1 and T2, the voltage measured between T3 and T2 will be exactly half of the voltage between T1 and T2. This voltage measurement is independent of the lumen dimension, and thus does not provide any extra information. On the other hand, if the single measurement electrode (e.g., T3) is placed slightly off center between T1 and T2, the voltage value between T3 and T2 is dependent on the lumen dimension. In general, if there are many measurement electrodes uniformly spaced between the excitation electrodes, about half of the measurements will not provide any additional information, whereas roughly half will provide additional information. Hence, a slightly skewed spacing of electrodes can be chosen to maximize information obtained while using a minimal number of measurement electrodes.

The size of the excitation electrodes corresponding to T1 and T2 have to be chosen keeping in mind the contact impedance and mechanical and anatomical constraints. Because of mechanical constraints and the winding nature of the anatomy, the vessel dictates that the sizes are kept as small as possible. If the size is made too small, however, the contact impedance of the electrode would become the dominant factor affecting the voltage measurements. Since the contact impedance is largely independent of the lumen dimension, this reduces the sensitivity of the voltage measurements to lumen dimension. Based on experimentation, the suitable electrode size was found to be one with an outer surface area of about 1 to 2 square millimeters. However this does not imply that a size that does not conform to this range is unsuitable. There would be a trade-off with accuracy of lumen dimension estimation and mechanical properties.

Figure 4:
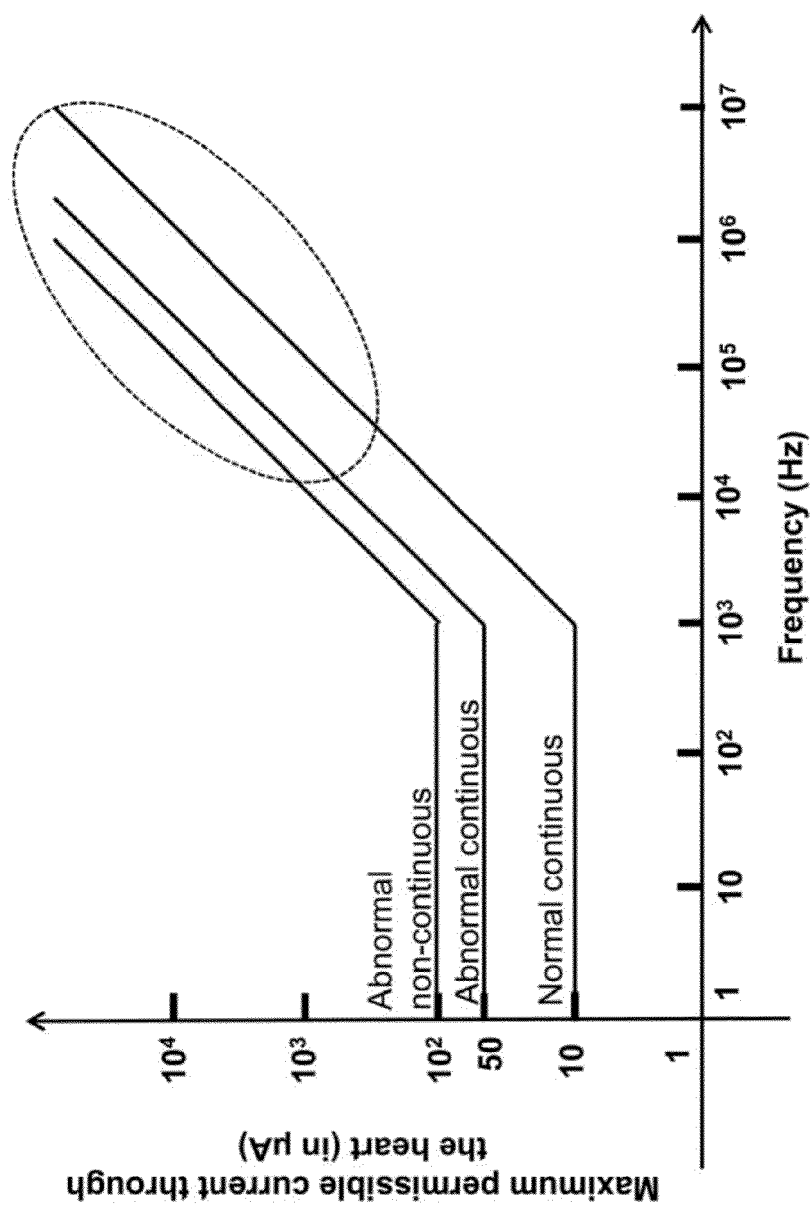
FIG. 4 is a graphical representation that shows examples of current values that may be provided to a heart tissue over a range of frequencies.

FIG. 4 shows a graphical representation for exemplary current values that may be provided to a heart over a range of frequencies. For example, maximum permissible current through a heart (in miliamperes) may vary over the range of frequencies. The maximum permissible current through a heart may also vary depending on whether the current is applied in an abnormal non-continuous manner, abnormal continuous manner, or normal continuous manner as shown. The embodiments described herein under operation are designed to use the excitation currents within the permissible safety limits. In some embodiments the excitation may be applied at a specific frequency or at specific sets of frequencies. In some other embodiments the excitation may be applied over a range of frequencies. In some embodiments, the range could be 40 KHz to 10 MHz. In general, the frequency range is chosen so as to provide maximal differentiation of the electrical properties of the constituent elements of the electrical network of the region of interest.

Because blood, vessel wall, fatty tissue, and calcified tissue each have distinctive frequency-dependent electrical properties, the total electrical current applied, as well as the three measured voltages, have values whose magnitudes, phases and frequency dependences depend upon the relative portion of the current flowing through the blood and the vessel wall. Overall, the frequency-dependent measurements depend upon several factors, including the frequency dependent electrical characteristics of blood, the diameter of the blood vessel (DBLOOD), the frequency dependent electrical characteristics of the wall, the thickness of the wall (TWALL), and the electrode geometry and spacing. Referring to the example in FIG. 1, once the values of V1, V2 & V3 over a range of frequencies are determined (or any other number of voltages measured depending on the number of electrodes), it is possible to estimate DBLOOD with a high degree of accuracy through method described below. Optionally, in the process electrical characteristics of blood can also be estimated. This may provide additional clinical value in terms of physical properties of blood such as hematocrit.

Some prior art approaches to determine lumen size have serious deficiencies. For example, one prior art approach attempts to estimate the lumen diameter using a device which consists of only two terminals. The method uses simplistic electrical representation of the blood and wall and requires injection of a second fluid for the measurements. A single frequency is used when passing the excitation current through the terminals, and therefore does not excite through a range of frequencies. The electrical path through blood is represented by a single electrical impedance. The electrical path through the wall is represented by a parallel impedance. The method involves taking a minimum of two measurements—the first measurement is with the existing conditions, and the second measurement taken after replacing blood with a saline solution whose electrical conductivity is markedly different from that of blood. In this approach two assumptions are made: the impedance of the parallel electrical path through the wall is unchanged over the two measurements; and that the impedance of the "blood" path in the two measurements is inversely proportional to the conductivities of the medium. In other words, the impedance Z=K/sigma, where sigma is the conductivity of the blood or saline and K is a constant whose value depends on the diameter of the blood vessel and the electrode geometry. The value of Z does not depend upon the electrical characteristics of the wall of the vessel.

Figure 5:
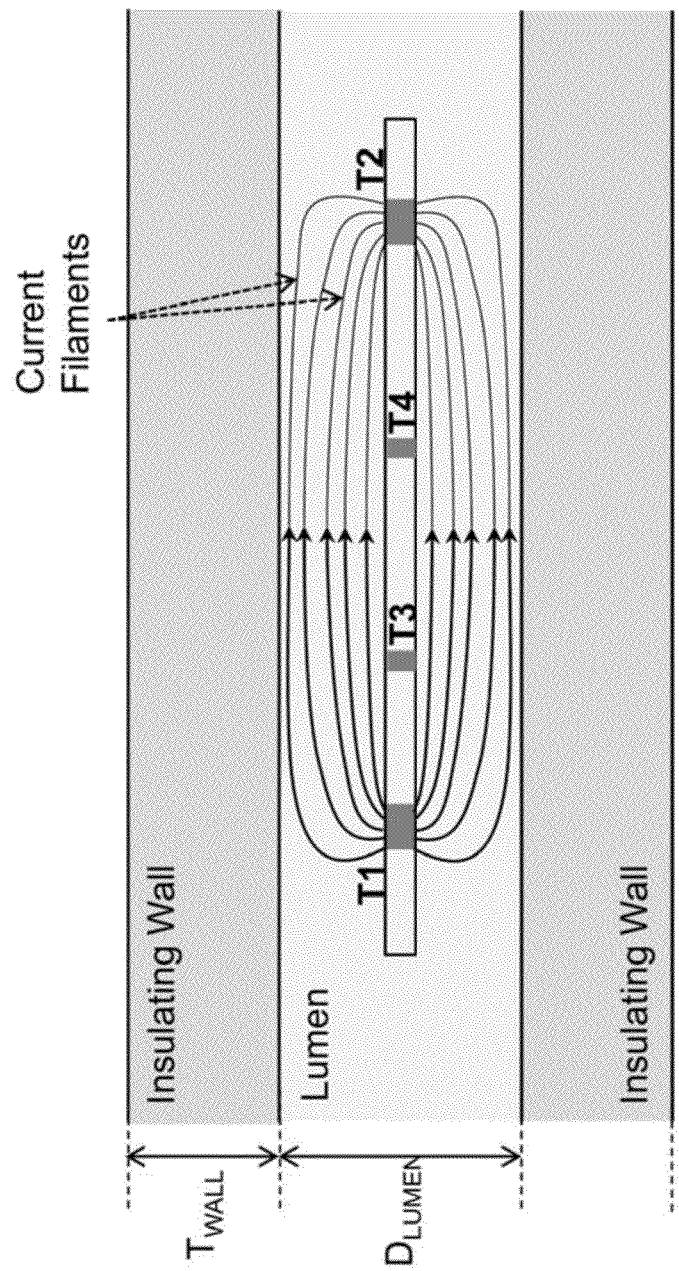
FIG. 5 depicts current filaments when the vessel wall is insulating.
Figure 6:
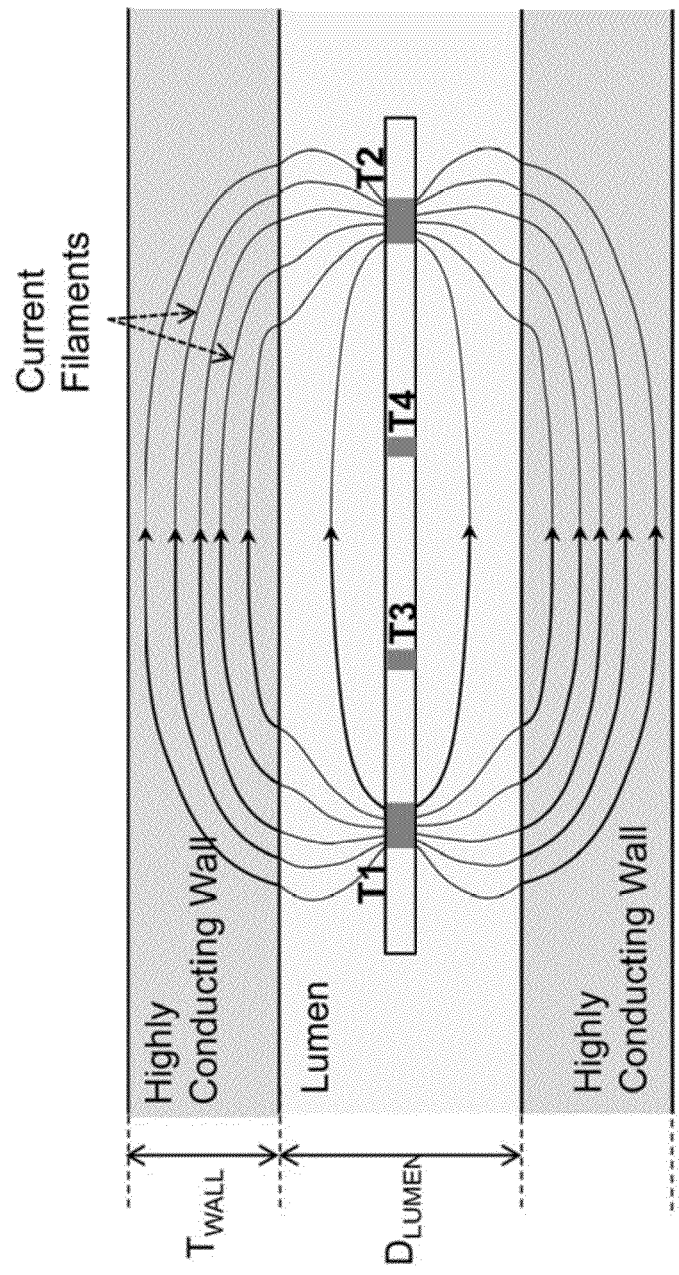
FIG. 6 depicts current filaments when the vessel wall is highly conducting.

There are fundamental problems with the above described prior art approach. First, the parallel path through the wall is not composed of a single type of tissue. As can be seen in FIG. 1, the electrical path involving the vessel wall has many electrical current filaments that pass through varying degrees of blood and vessel wall. Additionally, in the diseased section of the artery there will be varying degree of plaque of different morphology (calcified, not calcified, fibrous etc.). Thus, the overall impedance of the "parallel path" would depend on the electrical characteristics of the blood as well in healthy arteries and other plaque tissues in diseased arteries. Hence, during the second measurement, the parallel path would change in impedance since the blood is replaced by saline. The second problem is subtle but perhaps more crucial. The assumption of the blood path being independent of the wall characteristics is incorrect. As an illustration of this problem. FIG. 5 and FIG. 6 depict the electrical current filaments for two extreme cases—the first case shown in FIG. 5 occurs when the wall of the vessel is insulating (i.e. the conductivity of the wall is much lower than the blood). The second case shown in FIG. 6 occurs when the wall is highly conducting. Comparing the two figures, it is seen that for the second case in FIG. 6, the electrical current filaments have a distinctly different shape. The filaments are drawn towards the wall where most of the current conduction happens. In consequence, the volume of blood conducting the electrical current is reduced, leading to an effective increase in impedance of the "blood path".

In this previous approach, the conductance of the wall stays the same, while the conductance of the medium in the lumen is varied. But the effect is the same when the conductivity of the wall is varied (i.e., relative conductance is the important factor). While extreme conductivities have been used to illustrate a point, the effect is less pronounced in most cases but nevertheless present even with moderate changes of relative conductivities. It is straightforward to verify these observations objectively using Electromagnetic (EM) simulations.

In addition to the deficiencies of the prior art approach as set forth above, it also does not vary the frequency of the excitation (i.e., frequency diversity), nor does it utilize spatial diversity. The lack of frequency diversity generally leads to poor to no discrimination between various types of tissues. The lack of spatial diversity leads to reduced robustness. It also reduces sensitivity to the effects of electrode geometry. The current filaments crowd near the electrodes and progressively span out away from the electrodes. This effect is inherently captured by measuring the voltages along multiple points along the axis of the wire.

As set forth above, different types of tissue (or non-tissues found in the body) have different signature in voltage and current relationships as the frequency of excitation is varied. For example, as shown in FIG. 2 and FIG. 3, a blood vessel, blood, and fatty tissue each have different signatures in voltage and current. In some exemplary embodiments the methods and systems herein provide an excitation signal simultaneously at multiple frequencies, and that measure electrical responses as a result of the excitation signal (i.e., frequency diversity). These methods and systems allows the measurements to be made simultaneously, which allows the measurements to be made during the same phase of a heartbeat, such as during the systolic phase or the diastolic phase. This overcomes the difficulty associated with overlaying multiple measurements made at different times to account for the phases of the heartbeat. Some exemplary measurements made using the methods described herein include, for example, but not limited to, lumen dimension, nature of a specific region of the lumen like fat, stenosis, block, artery, blood pressure, blood flow rate, tissue, and the like, and combinations thereof.

In some embodiments the measured signals are voltages measured between a plurality of sensors, such as electrodes. For example, in reference to FIG. 1, after an electrical signal with a plurality of frequencies is flowed through terminals T1 and T2, voltages V1, V2, and V3 are measured at each of the frequencies, although any number of voltages could be measured based on the number of sensors. Terminals T1, T2, T3 and T4 are additionally spaced such that the sensitivity of measurement to changes in lumen dimension are maximized, as described above in reference to spatial diversity. The frequency response of V1, V2, and V3 are then used to estimate a lumen dimension, such as the lumen diameter.

Figure 7:
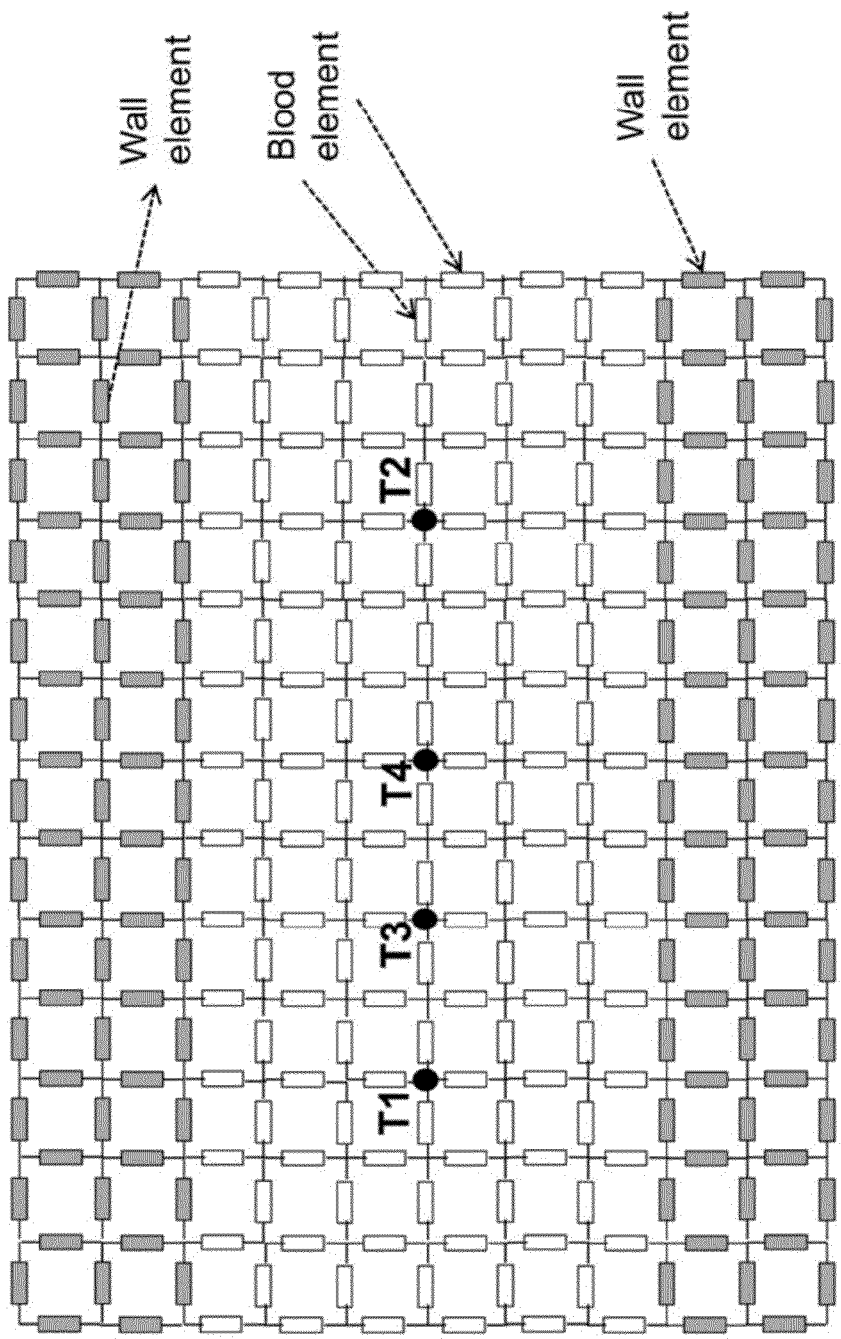
FIG. 7 illustrates a mesh modeling network.

In one embodiment in which one or more lumen cross sectional areas are being determined, the electrical path in the area of the lumen is modeled using a mesh network. One such example is depicted in FIG. 7. There are 2 types of electrical elements, blood elements and lumen wall elements, each representing a unit element of the tissue. Such a mesh network is an approximation of the continuous medium that conducts electricity. To reduce the approximation error, a finer mesh can be chosen. The trade-off is between the required accuracy and the computational complexity. The more accurate the approximation, the more computational complexity is required. In its coarsest form (with the least accuracy), the mesh is reduced to one element for blood and one element for the wall, which is an approach that has been previously attempted. Needless to say, this is too gross an approximation.

In the mesh network, the impedance of each blood element is a linear function of the lumen cross-sectional area and inversely proportional to the conductivity of blood. In an alternate formulation, the impedance of the blood element can be kept independent of the lumen dimension, but the number of elements would change based on the lumen dimension. The latter is practically inconvenient since the topology of the electrical network is not constant, and the changes allowed in lumen dimension are discrete steps rather than being arbitrary. Similarly, the lumen wall elements have impedance that depends on the wall thickness as well as on the electrical conductivity of the wall. Anatomically, the lumen wall may have multiple layers. For a more accurate model, additional types of elements may be added to the mesh network. For example, elements related to fatty tissue or calcified tissue are included in the model. Additionally, a 3-dimensional mesh may also be constructed for better accuracy of modeling.

Given this mesh network and the voltages V1, V2 and V3, which are measured over a range of frequencies, the lumen dimension is solved iteratively as follows, and as shown in FIG. 7A. After obtaining electrical voltage measurements VM1, VM2, and VM3, assume particular frequency-dependent electrical model parameters for blood, tissue, lumen dimension, and wall dimension. Then, using the assumed parameters, solve the equivalent electrical network and obtain voltages V1, V2, and V3. Then, compare the model voltages with the actual observed voltages. If the differences are not minimal, apply a correction to all of the parameters based on the differences and repeat the solving step. When the differences are minimal, the lumen dimension can be declared based on the converged geometrical parameters. The steps can be implemented using standard fitting techniques such as, for example without limitations, least squares fitting methods such as Gauss Newton method, Steepest Descent method, and Levenberg-Marquardt method.

Figure 8:
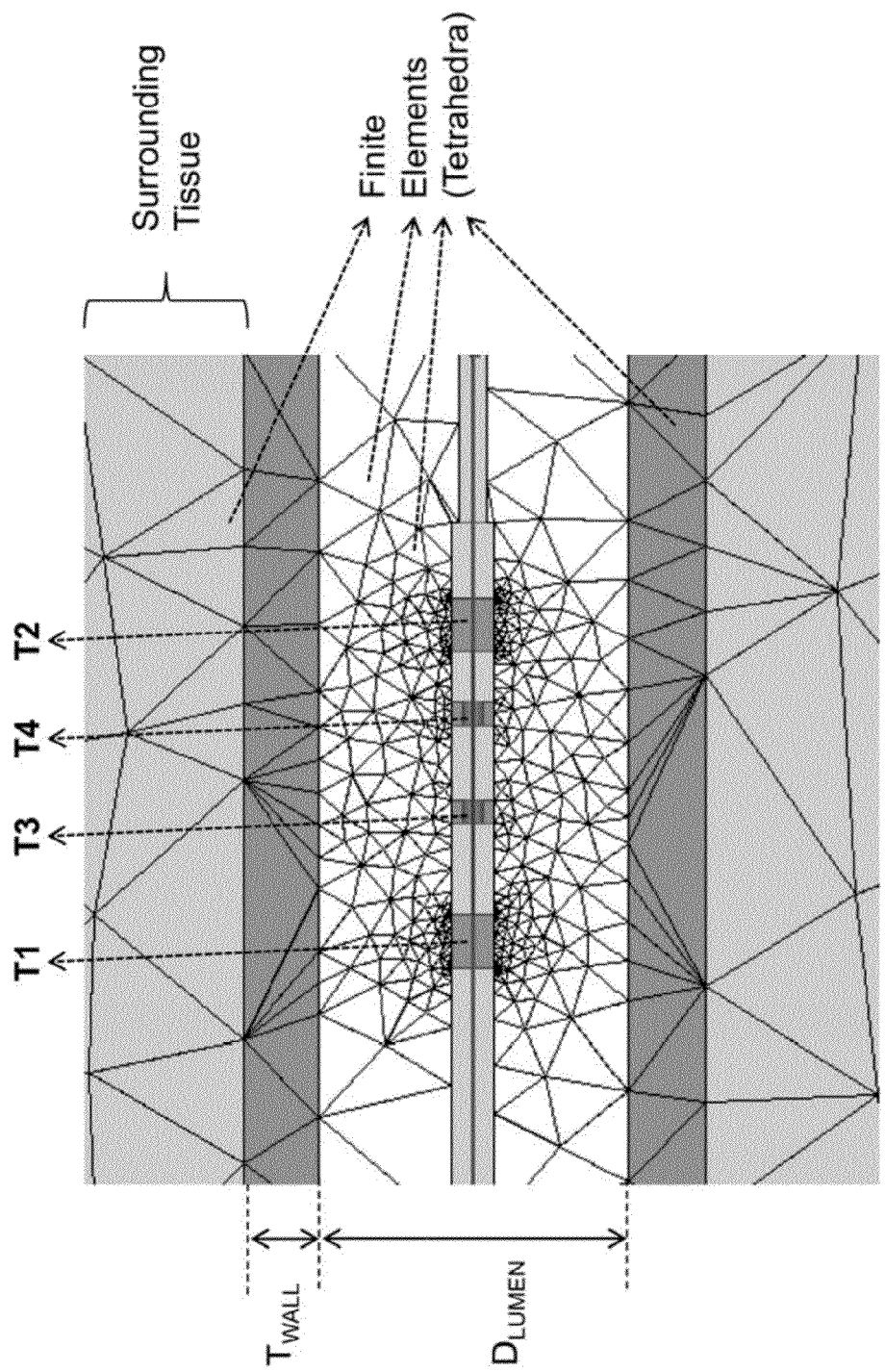
FIG. 8 illustrates a finite element model of a lumen with a medical device therein.

In a second embodiment in which a lumen dimension is being determined, the lumen region, including the blood and lumen wall, is modeled using an Electromagnetic (EM) simulation tool. The EM tool uses finite element method ("FEM") to break down the lumen region into smaller elements (e.g. with tetrahedron shapes). One example of breaking down into finite elements is depicted in FIG. 8. Given the electrical and magnetic properties of the bodily material in the lumen region, the tool applies fundamental Maxwell's equations of electricity and magnetism to solve for all voltages and currents in the entire lumen region. An iterative approach similar to the method described for the mesh network can be used to determine the lumen dimension. The difference between FIG.

7A and FIG. 8A is the step of solving the equivalent EM FEM model and obtain voltages V1, V2 and V3 for the given parameters.

In both the iterative methods described above, the lumen dimension is reasonably assumed to be approximately constant in the vicinity of the electrodes. The typical electrode separation is in the order of few millimeters. This means that the lumen dimension is assumed to be approximately constant over a few millimeters along the axis of the lumen. In most practical cases, the lumen dimension does not change significantly within a few millimeters of axial traversal. In the case of variations within these few millimeters, the estimated lumen dimension would be a local average of the lumen dimensions along the axis. The local average would be representative of the mid-point between the two excitation electrodes. In a typical procedure, the measurement electrodes would traverse the length of the blood vessel, and measurements would be taken at multiple places. Thus the lumen dimension would be estimated for different regions of the blood vessel.

In the iterative methods described above and illustrated in FIGS. 7A, 8A and 8B, it can be noted that, along with the lumen dimension, electrical properties of the bodily elements are also determined. These include the conductivity of blood and wall. These electrical properties are also available as output to infer clinical parameters such as hematocrit and characteristics of blockages if any (for example calcified blockages).

The EM approach is a much more accurate model for the lumen region than a mesh electrical network, such as is shown in FIG. 7. However, it is also very computationally complex. The solving step in the EM model would generally require a large amount of time. To speed up the calculations, a modified approach can be taken. In the modified approach, the EM tool is used offline, prior to use within a patient, to compute voltage distributions for many possible sets of geometrical parameters and frequency-dependent electrical model parameters. The values of the parameters for which the EM simulation is performed cover the entire operating range of the parameters. EM simulations are done for discrete (and judiciously chosen) parameter values and a look-up table is created. For parameter values that are not explicitly simulated, interpolation is performed. In rare cases the parameter values may lie outside the range for which EM simulations have been performed. In such cases extrapolation is done rather than interpolation. Extrapolations generally have larger errors than interpolations, but in such cases, it has been found that it did not affect the accuracy of lumen dimension estimation. Thus, the EM simulation results corresponding to any possible set of parameters are made available even before any measurement is actually made. Creation of the look-up table is a time consuming task, but one that can be done off-line using arbitrarily heavy computing resources. Once the look-up table is created, the solving step in the EM model becomes computationally simpler. For the given parameter values—geometrical dimensions for the lumen wall, and frequency-dependent electrical model parameters—the corresponding voltages V1, V2 and V3 are read out from the look-up table. It is possible that interpolation or extrapolation is required to obtain the voltage values for the given set of parameter values. The values V1, V2 and V3 thus obtained would be equivalent to what would have been obtained if a full EM simulation were to be run for the given set of parameter values. FIG. 8B illustrates a flowchart for creating a look up table for voltage responses (the flowchart on the left side of the figure) and a method of determining lumen dimension using the look-up values (the flowchart on the right side of the figure).

In embodiments in which pulses are delivered in a range of frequencies simultaneously, measurements can be taken over any frequency range. Measurements may be taken at any frequency range where the resulting plots for the various tissue types vary in shape. For example, as shown in the shaded region 134 in FIG. 3, the shapes of the impedance magnitude and/or phase curves for aorta, blood, and fat vary over the frequency range. Measurements may be taken within a frequency range with any degree of frequency step size. Step size may remain the same or may vary over the frequency range. In some embodiments, measurements are taken at about 40 KHz to about 10 MHz, where the frequency characteristics of impedances of blood, fat and other tissue types show distinctive differences.

The impedance magnitude and/or the impedance phase, illustrated in FIG. 2 and FIG. 3, may be scalable. For example, if measurements are taken for 1 cubic millimeter of a tissue type, and if the measurements are taken for 2 cubic millimeters of the same tissue type, the measurements for the same tissue type across the frequency spectrum will be some factor multiplied by the first measurements' value. In another example, if the first set of measurements for a first amount of a tissue type yields a particular curve over a range of frequencies, the second set of measurements for a second amount of the same tissue type over the same range of frequencies may yield a curve that is a scaled version of the first curve. The difference in one or more dimensions of the tissue may result in a factor that is multiplied by the first set of measurements.

The impedance magnitude and/or the impedance phase may also be additive. For example, if measurements are taken for a first amount of a first type of tissue, measurements are taken for second amount of a second type of tissue, and measurements are taken for a combination of the first and second types of tissue, the measurements for the combination may include the first set of measurements and the second set of measurements added together. In some embodiments, the first and second sets of measurements may be weighted by one or more factors. In another example, if the first set of measurements for the first tissue type yields a particular curve over a range of frequencies, and the second of set of measurements for the second tissue type yields a second curve over the same range of frequencies, a third set of measurements for a combination of the first and second tissue types may yield a third curve over the same range of frequencies that may be the first curve times a first factor plus the second curve times a second factor. The factor may be 1, less than 1, or greater than 1. In some embodiments, scaling only occurs in magnitude and not in phase.

In some embodiments, for a combination of impedance magnitude and impedance phase measurements taken over a range of frequencies for a combination of tissue types, there may be one set of tissue types of particular dimensions that will yield that combination of impedance magnitude and impedance phase measurements. Thus, the impedance measurements taken over the range of frequencies can yield the dimensions of the various tissue types. These dimensions can be used to determine lumen dimensions, such as blood vessel cross-sectional areas. Thus, the unit electrical properties may be converted into volumetric data of the environment, utilizing the uniqueness of the combination.

In some embodiments where stimulating is performed over a range of frequencies, a pseudo random binary sequence ("PRBS") is used and in some embodiments orthogonal frequency division multiplexed ("OFDM") sequence is used, both of which are described in more detail below.

Figure 9:
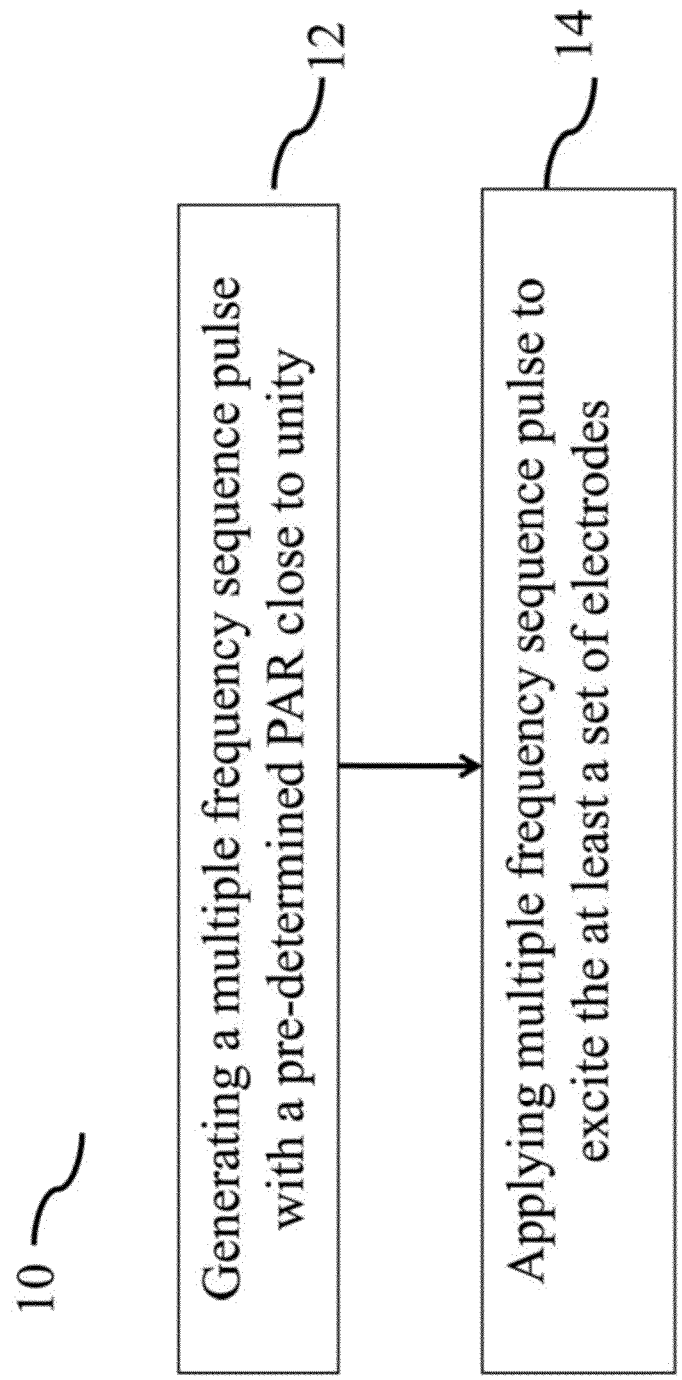
FIG. 9 illustrates an exemplary method of generating and applying a multiple frequency excitation signal.

In some embodiments the excitation signals are delivered through a plurality of electrodes in a target area in the vasculature. FIG. 9 shows an exemplary method 10. The method comprises generating a multiple frequency sequence pulse having a predetermined peak to root-mean-square (rms) ratio ("PAR") that is close to unity (i.e., 1) at step 12.

The level of excitation (i.e., energy of excitation) is limited due to restriction of peak admissible current into the area of interest. Consider a situation where the maximum current that can be injected into the body is Imax. The rms value of the current that can be safely injected is Imax/PAR, which is lowered if PAR is high. This in turn causes proportionately lower signal-to-noise ratio ("SNR") of the electrical responses from the lumen corresponding to the electrical excitation. A lower SNR causes a poorer accuracy of the final estimates.

In some embodiments the electrical hardware has a limited dynamic range. The receive chain design has to adjust its gain so as to keep the peak signal instances lower than its dynamic range. For a signal with high PAR, it would lead to lowering of the overall signal energy in the receive chain. As an example, a PAR of 2 would mean the receive chain is working at 2× lower signal strength than it could have worked and it can create a SNR degradation of up to 6 dB.

Designs with relatively higher PAR values do not necessarily prevent the system from functioning. It can potentially make it more inaccurate due to lowered SNR. Having a lower PAR is preferable. However, systems that can operate on a lower SNR or have a very high dynamic range (added complexity and cost in design) can still work with relatively high PAR values.

In some embodiments, an excitation with multiple frequencies and a desired PAR, i.e. PAR close to unity, is constructed by generating a pseudo random sequence. Without being bound to any theory, it is known that a pseudo random sequence of length L generated at a sampling of fs would contain discrete un-aliased tones of frequency from 0 (which corresponds to a DC frequency) to fs/2, in steps of fs/L. The power at each frequency (except DC) is equi-distributed while the phase of the individual tones is uniformly spread over $-\pi$ to $+\pi$.

One exemplary method of achieving the excitation would be using a digital-to-analog converter ("D/A" or "DAC") with low noise. D/As having the above stated requirements are known in the art, and can be effectively used with the disclosure herein. The D/A sampling rate needs to be at least double the required maximum frequency of excitation. The basic shape of the D/A converter output is a rectangular pulse of width equal to the time difference between two consecutive samples. It would be understood by those skilled in the art that if the D/A converter that outputs a pseudo random sequence is sampled at twice the desired maximum frequency (fH), it would create a frequency shape that is the product of the frequency shape of the basic pseudo random sequence and the frequency shape of the rectangular pulse (i.e. a Sine function with the first null at fs).

A significant advantage of an excitation based on pseudo random sequence with a basic rectangular shape is that its PAR is unity. This leads to maximizing the rms signal power for a given peak amplitude of the signal. There are further advantages on the performance of electrical hardware. The output of the D/A converter in this implementation has only two levels (−A and A), where A is the amplitude of excitation. The linearity of the transmit chain is irrelevant since non-linearity only produces a gain error and offset error to the signal. The receive chain design is also simplified with a lower PAR since dynamic range and linearity requirements are less demanding. Another major advantage of such an excitation based on rectangular pulse shapes (of duration ts=1/fs) is that the DA can be excited with a single bit excitation, minimizing the digital noise associated with toggling multiple bits simultaneously. A minor fall back of the rectangular pulse shape based approach is the small drop at higher frequencies of interest due to the roll off of Sine response (up to about 4 dB at fH=fs/2) which results in proportionate drop in SNR of the information for channel estimation. However this drop in SNR for channel estimation does not impact system performance. In alternate implementations, it may be possible to make the basic pulse shape as close to a Delta function, in which case, the frequency characteristics would be flat across frequency. However, this is associated with an increased PAR. The D/A converter output needs to be filtered effectively to prevent out of band emissions outside the band of interest. The filtering may be accomplished using a passive or an active analog filter with pass band at the region of interest. Filtering results in a small yet insignificant increase in PAR and PAR would still remain substantially close to unity.

In other embodiments, the excitation sequence is constructed as a repetitive orthogonal frequency division multiplexed (OFDM) sequence. The OFDM sequence consists of equal amplitude of all frequencies starting from a low frequency of interest to a high frequency of interest. The number of frequencies excited is proportional to the ratio of the high frequency (fH) to the low frequency (fL), while the spacing between frequencies is the same as the lowest frequency (fL) of interest that is chosen. The duration of the basic OFDM sequence is inversely related to its lowest frequency. The PAR of the OFDM sequence can be made to a low value close to unity by a suitable choice of phase for each frequency. In some embodiments, the PAR of the OFDM sequence is kept lower than 1.4. An OFDM based sequence is a sum of several discrete tones whose number is a power of 2, and provides distinct advantage of implementing the processing circuitry in an efficient manner based on Fast Fourier Transform (FFT).

In yet other embodiments, the excitation sequence can be constructed as additions of multiple coherent sinusoids with a method that would minimize the overall PAR of the sequence. PAR minimization can be achieved by suitably adjusting the phase of each sinusoid. Such sequences can also be constructed by appropriately dropping out one or more tones from the OFDM sequence. These sequences are particularly useful over a full-fledged OFDM sequence where the electrical hardware may not handle a large set of frequency information due to its limited capacity or, the non-linearity is too high and dictates the use of tones that have non-multiplicative relationship with each other, so that the non-linear effect of one or, more tones do not impact another tone.

It will be appreciated that the admissible rms current into the body is a function of frequency for a single frequency excitation. The admissible current levels are at a minimum of 10 uA and increase linearly with the frequency beyond 1 KHz. Approaches to this point have not described admissible current levels for multi-frequency excitations. FIG. 4 shows a graphical representation 16 of exemplary current values 18 that may be provided to a heart over a range of frequencies 20. For example, maximum permissible current through a heart (in milliA) may vary over the range of frequencies. The maximum permissible current through a heart may also vary depending on whether the current is applied in an abnormal non-continuous manner, abnormal continuous manner, or normal continuous manner. One possible way of determining the value of rms current for an excitation based on multi-frequency excitation sequence can be by matching the rms current of the composite signal to the corresponding admissible rms current for the lowest frequency.

The exemplary method 10 in FIG. 9 also includes delivering the multiple frequency sequence pulse across the set of electrodes placed in vivo 14. The excited set of electrodes then sends a pulse of electric current across the region of interest. Depending on the nature of the region of interest, a voltage is developed across the lumen in which the electrodes are positioned. There will be one voltage corresponding to each excitation frequency from the multiple frequency pulse. A vast amount of information can therefore be simultaneously obtained using the methods described herein.

Upon the excitation, the plurality of voltages developed across the lumen may then be detected using an appropriate measurement device that is capable of handling the signals simultaneously. Different types of bodily material have different signature in voltage and current relationships as the frequency of excitation is varied, as described above. For example without limitation, a blood vessel, blood, and fatty tissue have different signatures in voltage and current. The measurement device(s) may be configured to process the multiple sets of information sequentially, in parallel, or in groups to provide results.

The systems and methods herein provide the capability of making multiple measurements of a lumen at the same time. Because they are made at the same time, all the measurements are made during the same phase of heartbeat, such as in the systolic phase or diastolic phase. This overcomes the difficulty associated with overlaying multiple measurements made at different times to account for the phases of the heart.

The methods of use described herein can be administered effectively in the form of a software program, or algorithm. Thus, in another aspect, this disclosure provides algorithm(s) that performs the methods herein. In some embodiments the software includes algorithm steps adapted to generate multiple frequency pulses as described herein. The software may also be configured to then excite the set of electrodes with the multiple frequency pulse. The software may be configured to subsequently receive the multiple signals from the lumen to be processed. Further, other components that may be used with the algorithm include, for example without limitation, a display module such as a monitor having a suitable resolution, an input module such as a keyboard, a mouse, etc.

Figure 10:
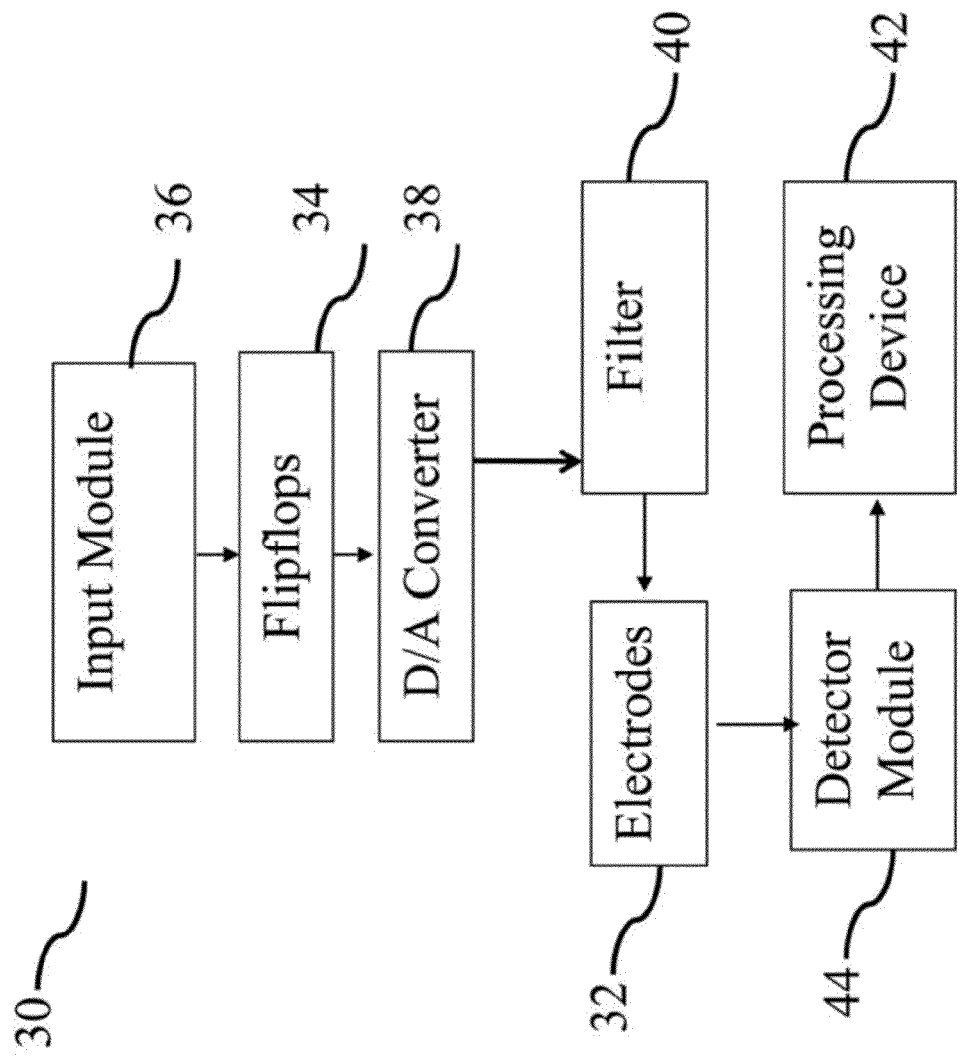
FIG. 10 is a block diagrammatic representation of an exemplary system.

In yet another aspect, the disclosure provides systems, including algorithms, that are adapted to perform the methods described herein. FIG. 10 shows an exemplary system 30 comprising at least a set of electrodes 32 configured to be placed in vivo in a lumen. The set of electrodes is capable of being excited by a multiple excitation pulse. The multiple excitation pulse is made possible using pseudo random generator that involves using a suitable number of flipflops 34. The number of flipflops desired depends on the complexity of the pulse to be generated, among other factors. The exact sequence to be executed by the pseudo random generator may be inputted using an input module 36. The input module may be configured to take manual inputs, or may be configured to automatically generate a sequence for the pseudo random generator to execute. As mentioned herein above, instead of a pseudo random sequence a OFDM sequence may also be used with the associated electronics for generation of the OFDM sequence as would be known to one skilled in the art.

In system 30, the multiple excitation pulse generated is then sent through a D/A converter 38. The system further comprises a filter 40, which may be a passive or an active filter, depending on various factors, such as, the necessity, the requirement of the situation, computing abilities, cost, and etc., and combinations thereof. In one specific embodiment, the filter comprises a passive multi-stage LC ladder network. Depending on the application, some embodiments can work without the need of such a filter.

The system further comprises a processing device 42 adapted to process the input for a pseudo random generator. The processing device may also be configured to send the multiple excitation pulse to the set of electrodes. The system may also comprise a communicating device (not shown in FIG. 3) to communicate the pseudo random generator with the set of electrodes. The communication between different components and modules may be achieved through any wired or wireless means known to those skilled in the art, and the exact requirement may be arrived at without undue experimentation.

System 30 also comprises a detector module 44 to detect the voltages developed across the lumen, which are described above. The detected signals may then be fed into processing device 42 for further processing. The signals may give rise to a wealth of information related to the lumen, which the processing device is configured to determine based on inputs such as, but not limited to, the signal, the algorithm, the lumen characteristics, and the like. Thus, the system of the invention may be used to make multiple simultaneous measurements of the lumen, without having to resort to stitching of data acquired at different time points which may introduce errors into the final measurement.

Example 1

Figure 11:
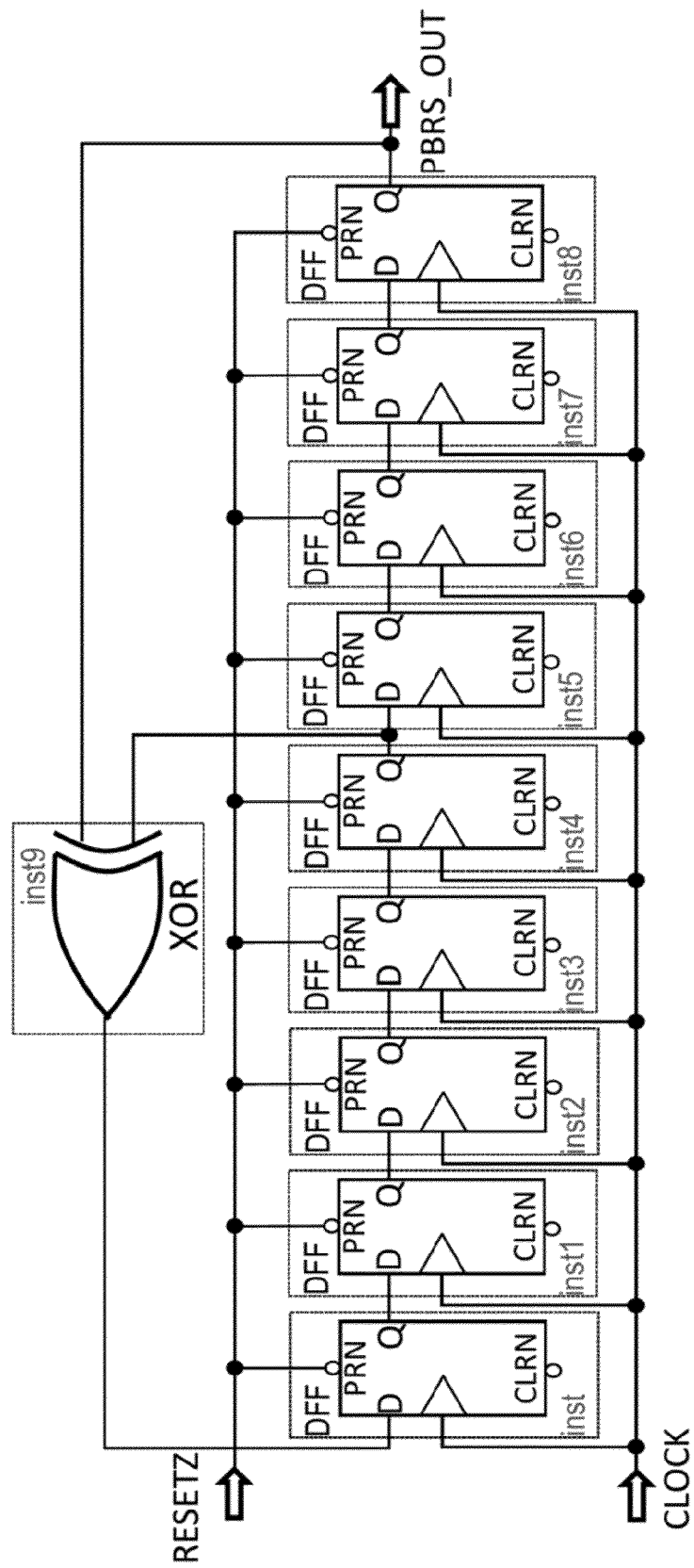
FIG. 11 shows an exemplary implementation of a pseudo random binary sequence.

In an exemplary implementation, the excitation frequency band was chosen between 40 KHz (fL) to 10 MHz (fH) based on the electrical characteristics of blood, tissue and fats. A 16 bit D/A converter was chosen to operate at a sampling rate of fs (=20 MHz). The chosen D/A converter accepts offset binary sequence (0x00000 for the lowest value and 0xFFFF for the highest value). The Most Significant Byte of the converter is toggled according to the single bit pseudo random pattern, while the next bit was kept permanently at logic 1. All other bits were kept at logic 0. Hence the D/A input toggles between 0x4000 and 0xC000, depending on a 0 or a 1 from the pseudo random generator. The pseudo random generator resides on a back end entity and is comprised of a chain of 9 D-flipflops referred to as flops, to represent a 9-tap pseudo random sequence. The resultant sequence is a maximal length pseudo random sequence with length of L=511 (29-1). The generator polynomial used to generate the sequence is $$X9+X4+1=0 \quad (1).$$

which would mean that the input of the last tap is an xor-ed output of the first and the fifth flops, as shown in FIG. 11. The flop outputs are all initialized to 1's to begin with (Reset condition). The tones present in the excitation sequence are multiples of fl, wherein:

$$fl=fs/L=20/511 \ MHz=39.14 \ KHz \quad (2)$$

The D/A converter produced an output with frequencies spaced at 39.14 KHz. The output was passed through a bandpass filter whose pass band starts at a value lower than 39.14 KHz and ends above 10 MHz ensuring decent flatness over the entire band. In the specific implementation, the filter is designed using a passive multi-stage LC ladder network. Since the minimum frequency of the final composite signal is at 39.14 KHz, the signal rms value is maintained to be lower than 391 $\Box$A. The choice of the sampling frequency and the tap length depends on the minimum and maximum frequencies of operation. As described before, the sampling frequency is at least twice the maximum desired frequency in the excitation, while the tap-length (L) is the nearest integer satisfying the relationship $$L = [\log 2(fs/fmin)] \quad (3)$$

Figure 12A:
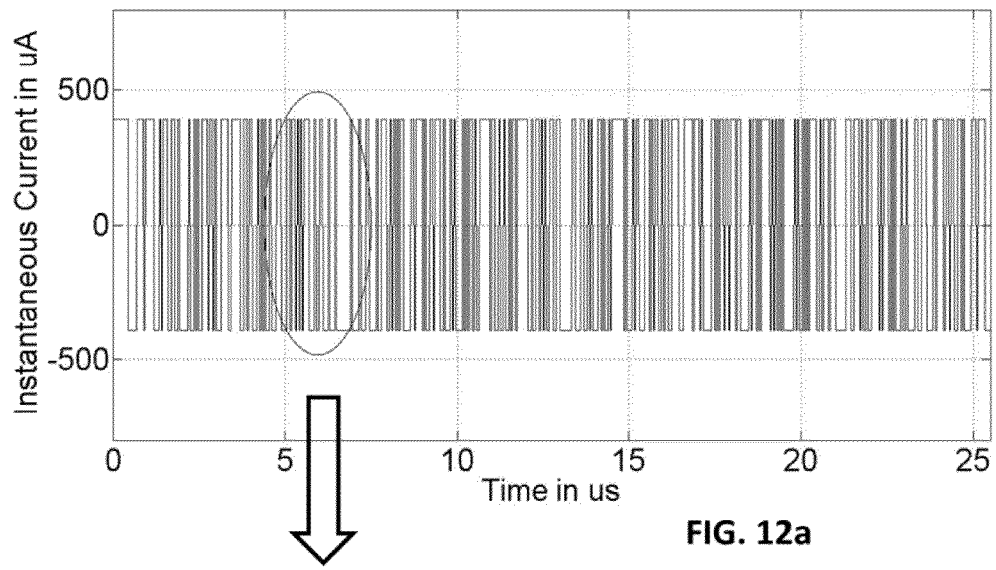
FIG. 12A shows the exemplary pseudo random binary sequence in time domain.
Figure 12B:
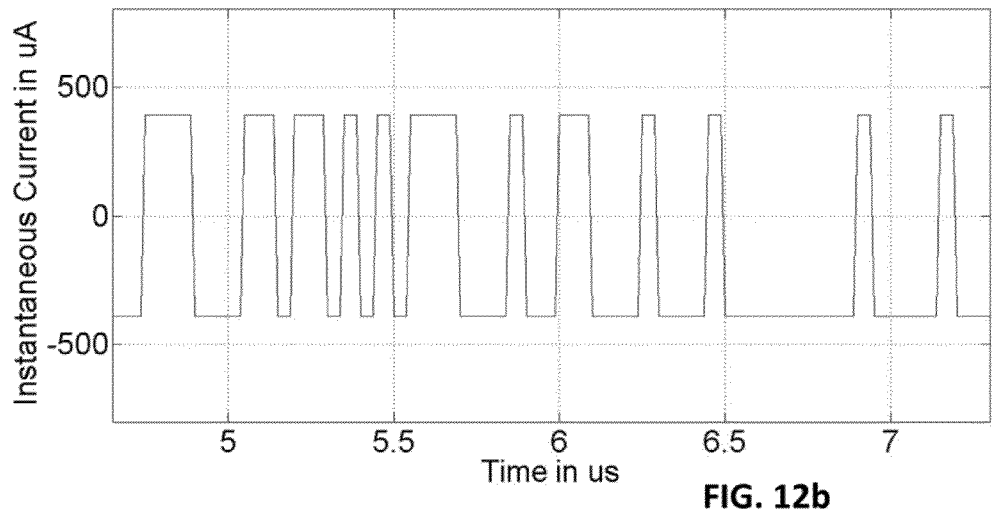
FIG. 12B shows a zoomed portion of the exemplary pseudo random binary sequence in time domain.

FIG. 12a shows the time domain waveform of the 9-tap pseudo random binary sequence generated as described herein. The waveform has an amplitude of 391 □a. FIG. 12b shows a highlighted portion of the exemplary pseudo random binary sequence in time domain.

Figure 13:
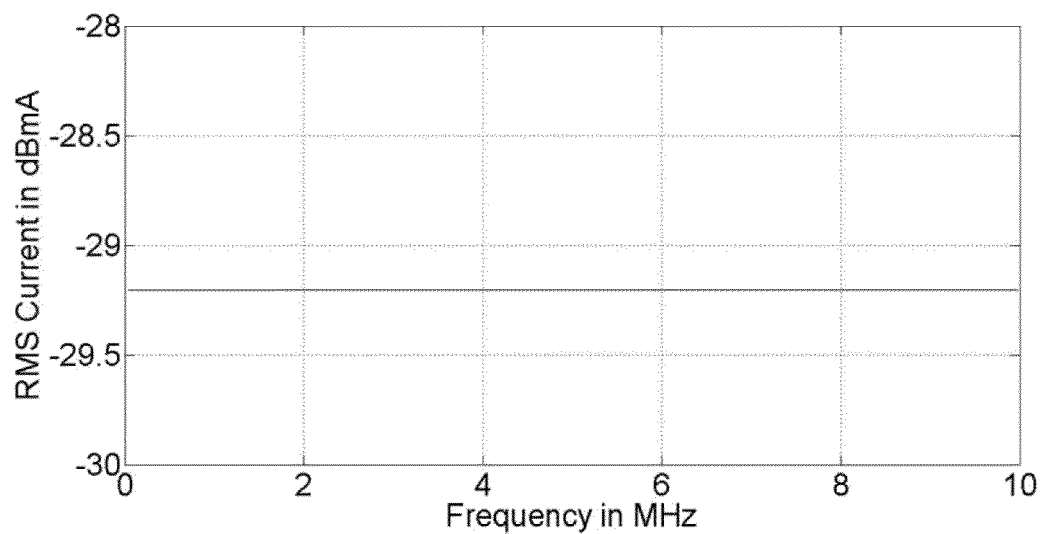
FIG. 13 shows the power spectral density of the exemplary pseudo random binary sequence.
Figure 14:
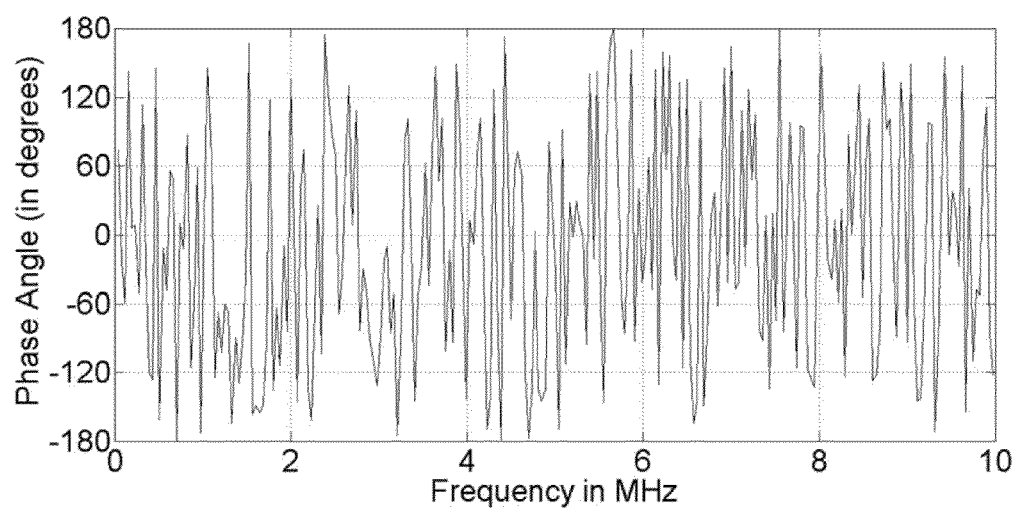
FIG. 14 shows the phase plot of the exemplary pseudo random binary sequence.

FIG. 13 shows the power spectral density of the same 9-tap pseudo random binary sequence generated. FIG. 14 shows the plot between phase angle and frequency for the 9-tap pseudo random binary sequence.

Example 2

Figure 15:
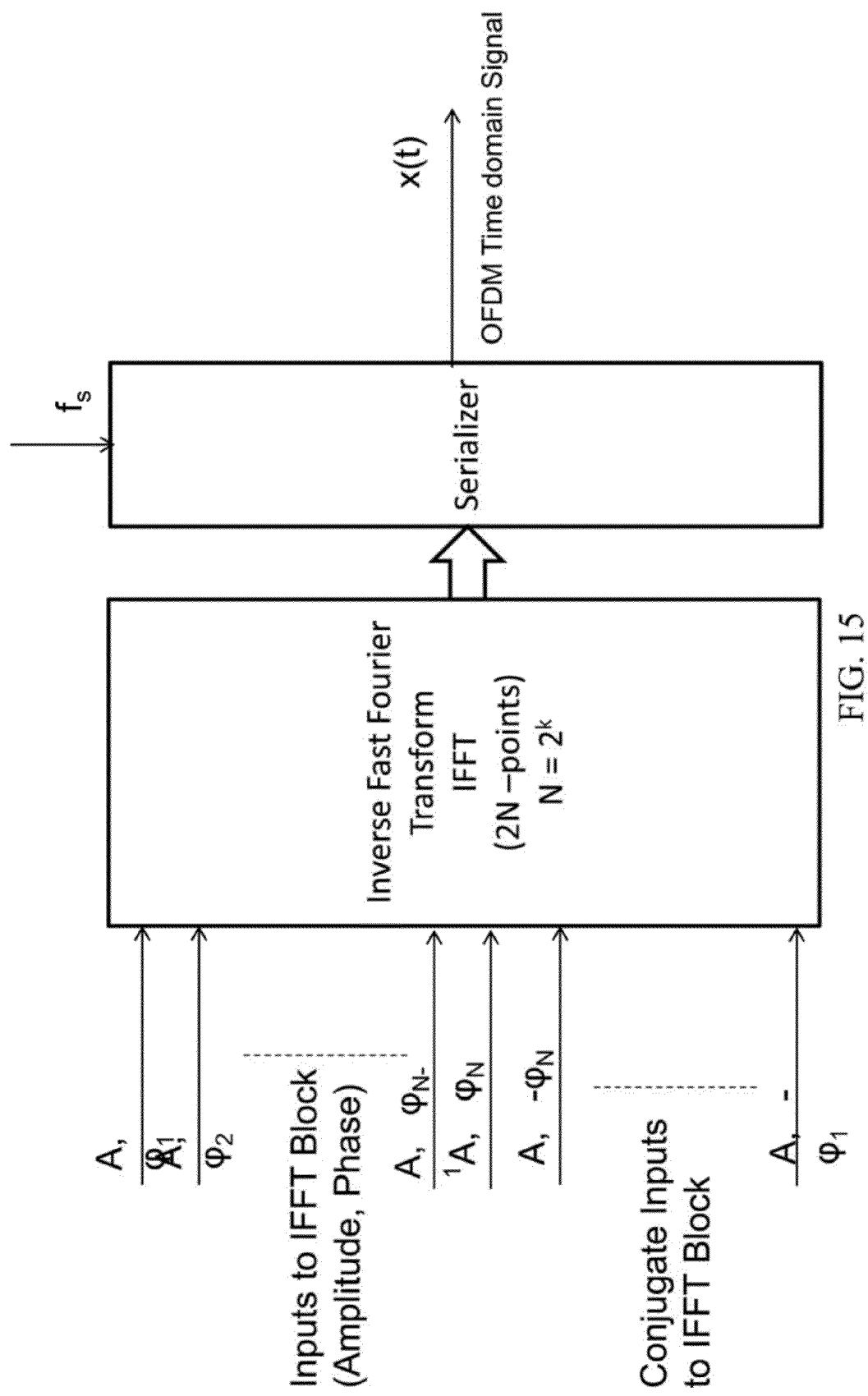
FIG. 15 shows an exemplary implementation for orthogonal frequency division multiplexed (OFDM) sequence using IFFT.
Figure 16:
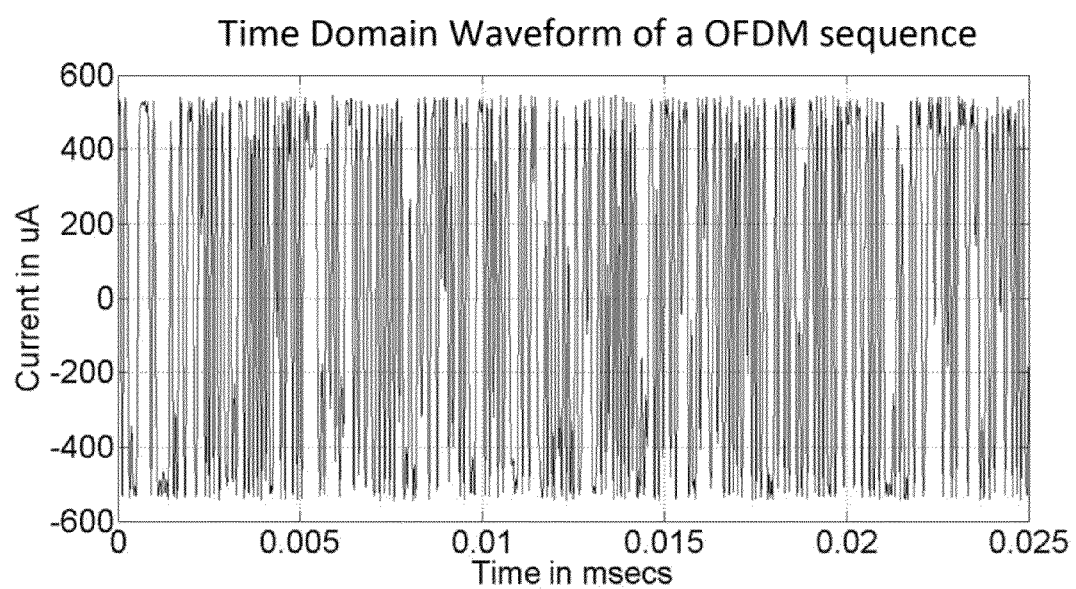
FIG. 16 shows a time domain signal for the OFDM sequence of FIG. 14 and FIG. 15.
Figure 17:
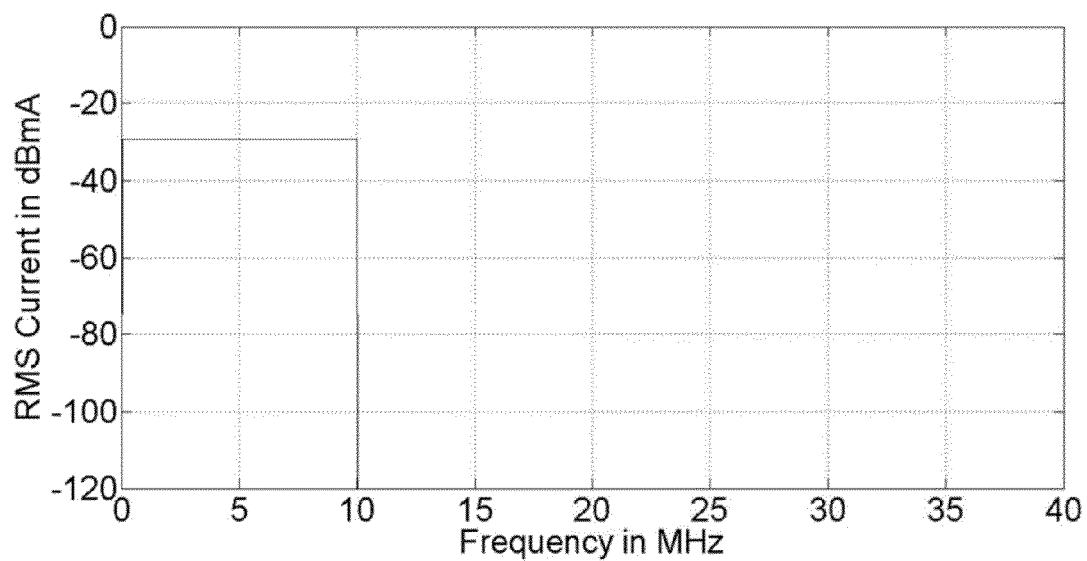
FIG. 17 shows the OFDM Frequency Response for the implementation of FIG. 15.

In yet another implementation, as shown in FIG. 15, an OFDM sequence is constructed using Nfreq (=256) discrete tones of equal amplitudes and each being at a random phase. The phase angles for each tone are adjusted so as to obtain the PAR lower than 1.4. The construction of the OFDM sequence can be done either simply by adding all the discrete tones together or, by performing a IFFT (Inverse Fast Fourier Transform) of a symmetric sequence of 2Nfreq (=512) complex numbers, where the first 256 complex numbers relate to the amplitude and phase of the individual tones and the next set of 256 complex numbers are simply the complex conjugate of the first 256 arranged in the reverse order (FIG. 15). The resultant time domain signal is shown in FIG. 16 that is sampled at fs (=20 MHz) which is twice the largest frequency of interest (fH). The lowest frequency in this sequence is fL (=fs/2Nfreq=39.0625 KHz). The time domain OFDM sequence can also be produced at higher sampling rates using appropriate size of IFFT inputs keeping the lowest frequency same. A higher sampling rate eases the requirement on anti-aliased filtering while increasing the complexity of the hardware in the transmit side FIG. 17 shows an exemplary OFDM frequency response for the implementation of FIG. 15.

Figure 18:
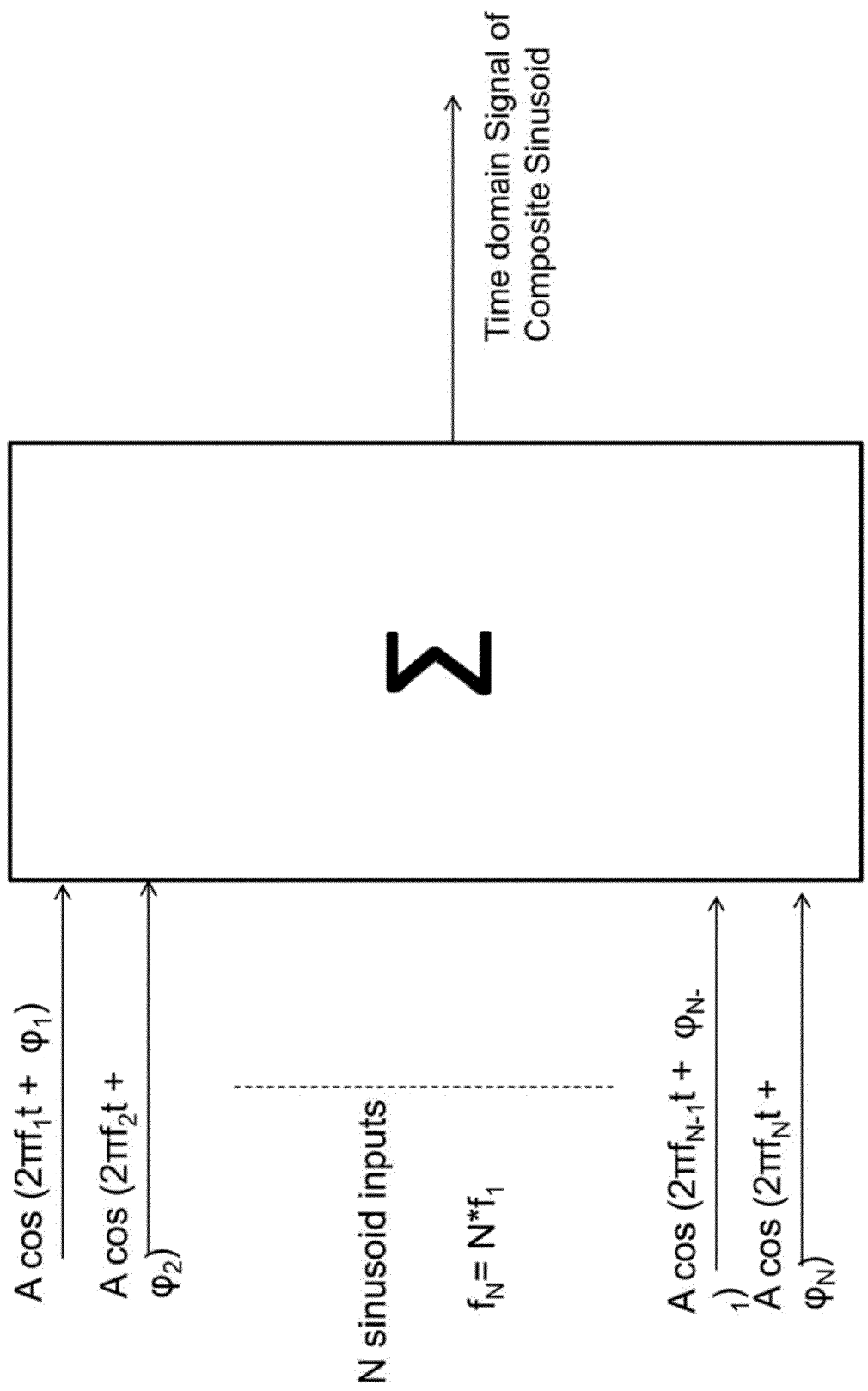
FIG. 18 shows an exemplary implementation for generating a multi frequency composite sinusoid.

In yet another embodiment as shown in FIG. 18, a customized sequence is created using multiple coherent sinusoids added with appropriate phase angles so as to minimize the PAR. The resultant sequence may bear the property where any given frequency is not harmonically related to any other frequency. The same can also be constructed in the OFDM framework described above, where one or, more IFFT inputs are nulled to remove a set of tones from the original sequence.

As referenced above, some embodiments also utilize spatial diversity, which generally refers to a difference in separation between electrodes. For example, voltage measurements may be taken between a first electrode and a second electrode that are at a distance from one another, and measurements may be taken between a first electrode and a second electrode that are at a second distance from one another. With spatial diversity the first and second distances are different. In other embodiments any number of electrodes may be used, and the distances between any two electrodes can be different from the distance between any two other electrodes, as is described above. Using different spacing between electrodes provides different voltage measurements for the same lumen dimension. Using all these sets of measurements to solve for a common lumen dimension leads to increased robustness. There are two reasons for this. First, the optimal electrode spacing depends on the dimension of the lumen being measured. Since the dimension is not the same in different cases, using such spatial diversity allows at least one set of electrodes being optimally or nearly optimally spaced. Secondly, some of the measurements can be affected by other factors that reduced its reliability. Some of the factors are (1) the touching of the specific electrode with the wall leading to anomalous measurement (2) Glitches in the measurement circuitry leading to incorrect voltage measurements for some electrodes. In these cases, some of the measurements can be identified as outliers and discarded, leading to a more accurate lumen dimension estimation.

Figure 19:
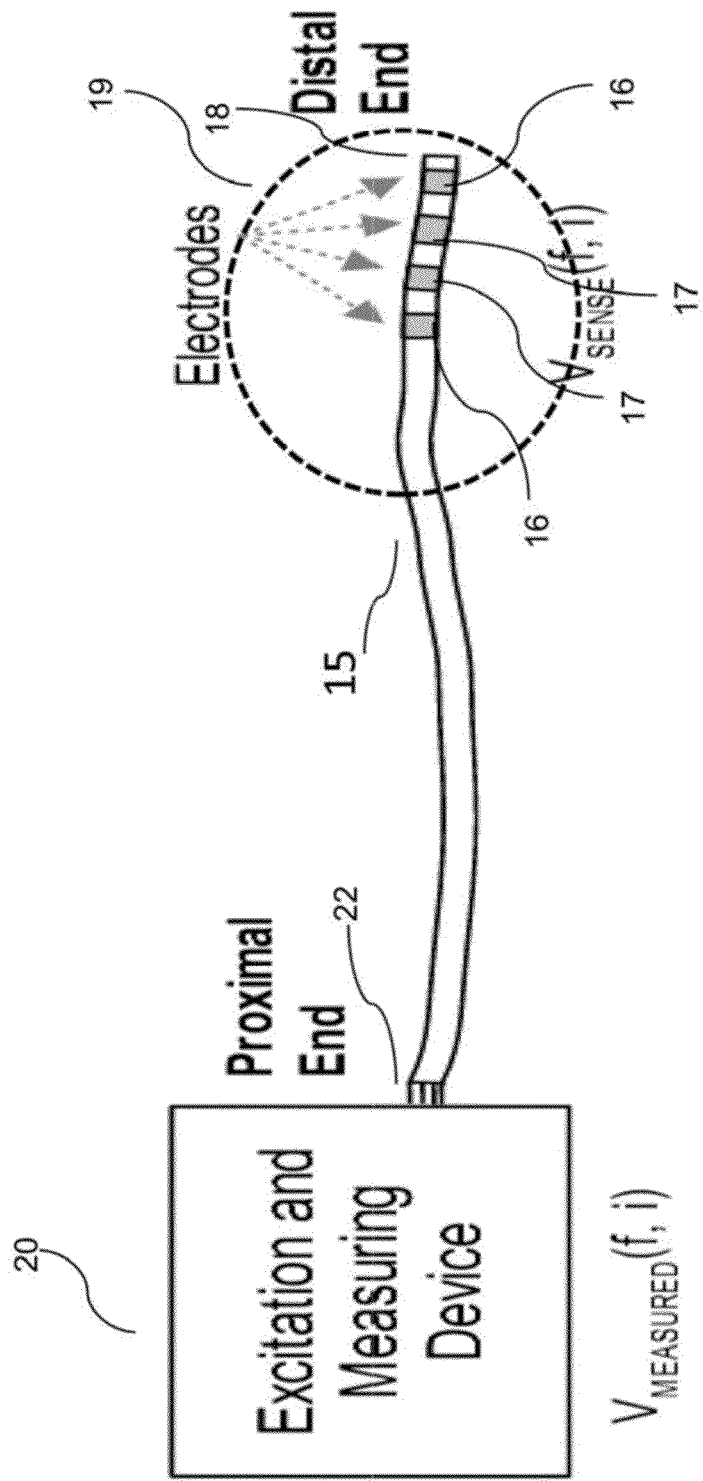
FIG. 19 is a diagrammatic representation of an exemplary diagnostic element and the associated circuitry for measuring a lumen dimension.

In some embodiments above the methods are described as providing excitation pulses across at least two electrodes. Exemplary delivery devices that can be incorporated into an overall system will now be described. The delivery devices can, however, be considered stand-alone devices. FIG. 19 is a diagrammatic representation of an exemplary embodiment of a diagnostic element. Diagnostic device 15 includes an elongate medical device on which at least two spaced-apart sets of electrodes 16 and 17 are disposed near distal end 18. Diagnostic device 15 is configured to be placed in vive proximal to a volume of interest 19 in a vasculature, for example a blood vessel, wherein a first set of electrodes is configured to receive an input excitation from excitation and measuring device 20, and a second set (or the first set) of electrodes is configured to receive a voltage signal referred to herein as an "response," or "responsive" voltage signal from the volume of interest 19. The second set of electrodes is configured to transmit the response voltage signal to excitation and measurement device 20 at proximal end 22 of the elongate medical device. Excitation and measurement device 20 receives and measures an output signal that is a function of the response voltage signal, and the output signal is processed to calculate a voltage difference between the spaced apart electrodes. The voltage difference is indicative of a lumen dimension, and is used to calculate one or more lumen dimensions. A set of electrodes has been referred to for measuring the signals from the volume of interest, however the device may have any number of electrodes. An exemplary advantage of the exemplary embodiment in FIG. 1, and the other embodiments herein, is that the system does not require that fluids be injected into the body lumen for obtaining the measurements. Additionally, the exemplary embodiment provides a direct method for obtaining the lumen parameters, increasing the ease of the procedure and the patient comfort.

Figure 20:
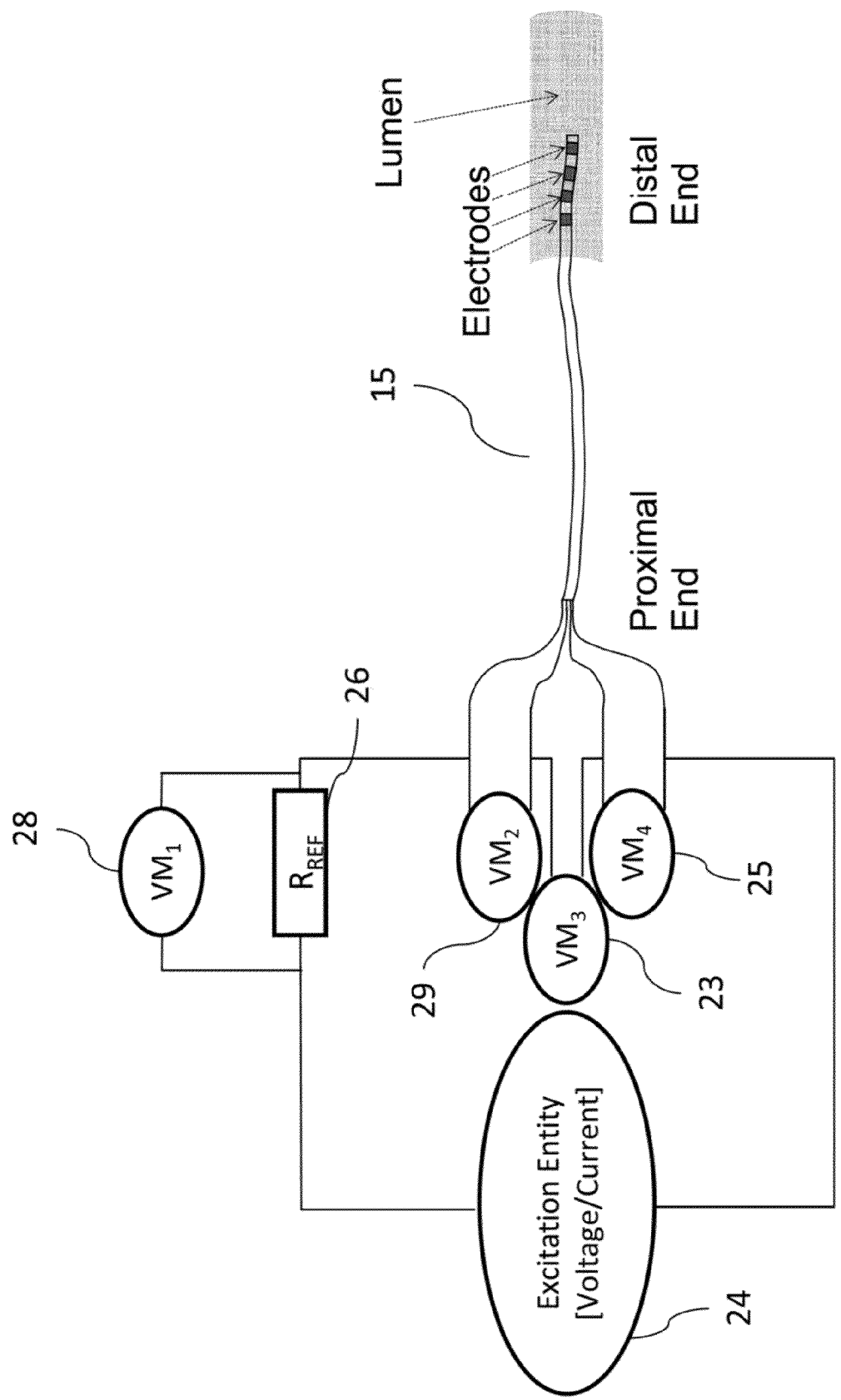
FIG. 20 is a diagrammatic representation of an embodiment of an excitation and measurement device to be used with the diagnostic element of FIG. 19.

FIG. 20 shows an exemplary non-limiting embodiment of excitation and measurement device 20 of FIG. 19. Excitation source 24 is used for exciting a set of electrodes of diagnostic element 15 via reference resistance 26, and the voltage measurements VM1 28. VM2 29, VM3 23, and VM4 25 (also referred to as output voltages in the description of specific embodiments) are received and measured after the excitation. It would be appreciated by those skilled in the art that other topologies for making these measurements are possible and are included herein. Measurements, such as electrical measurements as shown, may be taken between two or more electrodes. The voltage distribution, for a given excitation with frequency diversity, between the two electrodes may be measured continuously as the diagnostic element is advanced through the vessel. As mentioned earlier, the voltage distribution between the electrodes is indicative of the cross-sectional area of the lumen or volume of interest with the lumen, and is used for determining these lumen dimensions.

Figure 21:
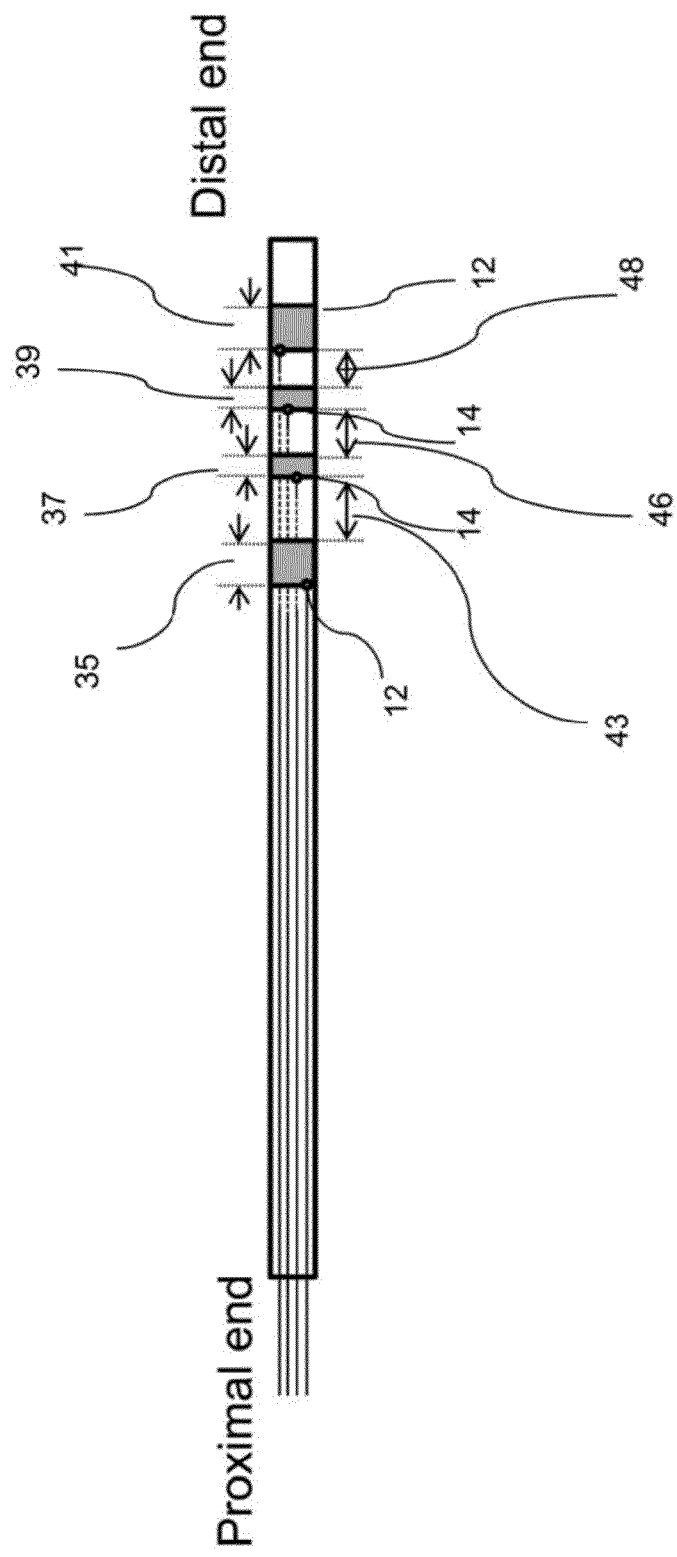
FIG. 21 is a diagrammatic representation of spaced apart electrodes at pre-determined positions according to one aspect of an exemplary embodiment.

The spaced apart electrodes of the diagnostic element may be arranged on the elongate element at pre-determined positions indicated by reference numerals 35 through 48 as shown in FIG. 21. The size and spacing of electrodes are designed for optimal performance. The electrodes may be mounted on a catheter or on a guide wire for placing them in vivo in the body lumen. In some embodiments, electrodes may be formed of a conductive material. For example, electrodes may include a metal, such as copper, silver, aluminum, gold, or any alloys, plating, or combinations thereof. Electrodes may include exposed portions of wires. Electrodes may include any electrically conductive material in electrical communication with electronics for providing and/or receiving an electrical signal and/or current.

Figure 22:
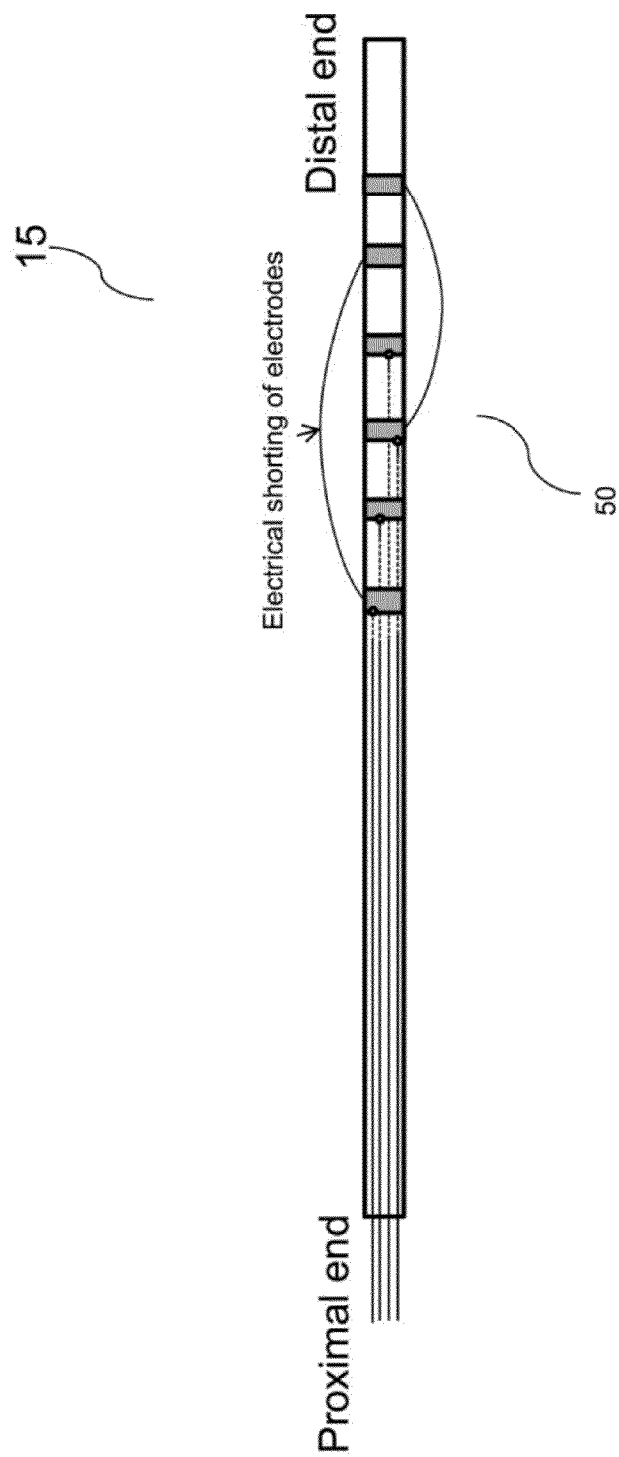
FIG. 22 is a diagrammatic representation of distributed electrodes.

The electrodes may also be arranged as distributed electrodes 50 as shown in FIG. 22 where multiple electrodes may be used. The distributed electrodes refer generally to a distributed electrode configuration where a single electrode is split into many and placed in several locations and are all connected to the same terminal. There are several ways for achieving the distributed electrode configuration and FIG. 22 is one non-limiting example. Here, several electrodes are connected to the same excitation source by shorting them through internal wires and thus achieving a distributed electrode configuration.

Additional different configurations of electrodes are possible for different aspects and some non-limiting examples are described herein. In one specific example the diagnostic element comprises three spaced apart electrodes, and in another example the diagnostic element comprises four spaced apart electrodes. In alternate embodiments, any number of electrodes may be used.

Further, the spacing between electrodes may be asymmetric with respect to a guide wire on which the electrodes are mounted. In yet another example, the electrodes do not surround the wire completely. Only a sector of the wire is covered by an electrode. Multiple such electrodes are placed covering different sectors of the wire. Specific electrodes are chosen such that they are most favorable. For instance, if the wire is touching the wall or the stent, it would be more favorable to use an electrode that covers a sector of the wire that is away from the wall or stent. It may be noted that in some configurations, the electrodes adapted to send the input excitation and the electrodes adapted to transmit the response signals may be pre-determined. Further it is possible to select more than one pair of electrodes to send the input excitation and similarly more than one pair may be selected to transmit the response voltage signal.

In yet another example the distance between each of the electrodes in the pair of electrodes may not be pre-determined, but the location of each electrode is deterministic by any known techniques. In some other embodiments, the distances between each of the electrodes may be fixed. In other embodiments, distances between electrodes may vary. In specific method of use, electrodes may be positioned in close proximity to an anatomical feature. For example, electrodes may be positioned in close proximity to a body lumen, such as a blood vessel, where the electrodes may contact the outside surface and/or inside surface of the body lumen. In some embodiments, the electrodes may be positioned within a body lumen while touching or not touching the body lumen. Each of the electrodes may be similarly positioned with respect to the body lumen (e.g., all electrodes contacting the outside surface of the body lumen), or various electrodes may have different positions with respect to the body lumen (e.g., some electrodes within a body lumen, some electrodes contacting the inner surface of the body lumen).

Further, in some embodiments, a guide wire may be integrated with the diagnostic element. The guide wire may also comprise multiple terminals that are spaced apart. In a specific example a first terminal and a second terminal are used that are spaced apart by a separator there between. The separator may comprise a polymer. The separator may be, in some embodiments, a non-conductive coating around the first terminal and the second terminal. The separator may electrically isolate and/or insulate the first terminal from the second terminal. The separator may comprise, but is not limited to, polypropylene (PP), polyimide, Pebax, polyphenylenc oxide (PPO), polystyrene (PS), high impact polystyrene (HIPS), acrylonitrile butadiene styrene (ABS), polyethylene terephthalate (PET), polyester (PES), polyamides (PA), polyvinyl chloride (PVC), polyurethanes (PU), polycarbonate (PC), polyvinylidene chloride (PVDC), polyethylene (PE), polycarbonate/Acrylonitrile Butadiene Styrene (PC/ABS), any other polymer, rubber, a thin walled heat shrink material or any other electrically insulating material. The electrical conducting wires may be made of copper, drawn filled tube (e.g., Fort Wayne metals or alike) stainless steel, silver alloy, tungsten or any other non-toxic electrically conductive material, chosen on the basis of their electrical and mechanical properties for particular applications. The electrical wires may further be insulated using extrusion, enamel coating, spray, or dip coating processes and using biocompatible insulating materials whose mechanical properties are appropriate for the application.

In some embodiments, the guide wire may also comprise a third terminal and a fourth terminal and wire. Separation and/or separators may be provided between the first, second, third, and/or fourth terminal. Any number of wires connected to discrete terminals may be provided in various embodiments of the invention. As would be appreciated by those skilled in the art, electrical insulation may be provided between the plurality of wires.

Separate electrically conductive wires or conductor wires may be additionally used or may be integrated with the guide wires and are used to connect the distal electrodes to the proximal end. These conductor wires may also be embedded either inside or the outside of a guide wire. In some case, the guide wire support itself can be employed as one of the aforementioned conductor wires. In a specific non-limiting embodiment, the guide wire may have a hypotube construction that would be well understood to those skilled in the art. In one particular non-limiting example, a conductor wire or multiple conductor wires may be wrapped on an outside surface of the core wire and encased within an external hypotube or within a polymeric material (e.g. heat shrink, or extruded polymer).

In another embodiment, a surface of the guide wire may have patterns such as and not limited to laser cut patterns to provide variable stiffness along the length of the guide wire. It would be appreciated by those skilled in the art that at different lengths different stiffness levels may be needed for ease of movement of the guide wire being placed in vivo inside a patient's body and these stiffness requirements may be met by providing different patterns on the surface of the guide wire. The stiffness may also be varied by providing different thickness polymer jackets around the guide wire. The guide wire may be a round or a flat wire depending on the desired application.

The attachment of electrodes with the wires may be achieved by using different techniques including but not limited to providing a slit in the electrode to route the conductor wire, crimping the electrode on the conductor wire and then laser welding, soldering or brazing the electrodes on the wires. In another example a hole may be provided in the electrode to attach the conductor wire. Electrodes may also be provided as coils that can be held on the hypotube by means such welding or bonding. Electrodes may also be provided as rings or bands mounted on the conductor wires. In another embodiment that uses guide wires, multiple electrodes in the coiled section of the guide wire can be implemented by exposing the coil to the blood by avoiding the non-conductive coating at the required places. To create multiple electrodes, a multifilar winding can be used and different mutually insulated wires can be exposed at the requisite places.

Further, in some embodiment the electrode terminals may be provided on separate wires which may or may not share a common support or active guide wire. Terminals may be arranged in a straight line. In other embodiments, terminals may be provided in a staggered configuration, within a planar arrangement, within a spatial arrangement, or may have any other location relative to one another. For all combinations of terminals, measurements may be provided responding to the same current and voltage values.

In some embodiments the electrodes are called leads, and are configured much like other coronary leads known in the art, but are configured to be part of the active guide wire. Some embodiments comprise more than two electrodes. In some embodiments one or more electrodes are positioned on a portion of the active guide wire's circumference at its distal end on the active guide wire. In some embodiments one or more electrodes encompasses the active guide wire's entire circumference at its distal end on the active guide wire.

In other embodiments sectorially-spaced electrodes may be provided. Sectorially spaced electrodes do not go completely around the active guide wire. This will allow an azimuthal delineation of the blockage i.e. the spatial orientation or plaque in a given cross section maybe feasible to determine as opposed to only cross section area. Since they only go around a portion of the active guide wire, the direction of the dimensions measured will be on the side of the active guide wire that the sectorially spaced electrode is on. In some embodiments, sectorially spaced electrodes may all be positioned on the same side of the active guide wire. Alternatively, they may be provided in varying axial locations around the active guide wire. As previously mentioned, other embodiments of the invention may provide other winding or braiding techniques for the wires.

An active guide wire may include a support with one or more wire wrapped around. The wires may have any configuration, which may include the types of windings or braiding previously described. The core of the active guide wire may have any diameter. In some embodiments, the diameter of the core may remain the same for the length of the core. In other embodiments, the diameter of the core may vary along the length of the core. There may be sections where the diameter of the core may remain the same for sections of the core, and may vary for other sections of the core. In some embodiments, the diameter of the core may be greater toward a proximal end of the active guide wire, and may be smaller toward a distal end of the active guide wire. In some embodiments, a standard diameter may be provided in a normal section, and a larger diameter may be provided in an x-support section. Similarly, the cross-sectional shape and size of core may remain the same or vary along the length of the active guide wire.

In some embodiments, one or more wires may be wrapped around the core of the active guide wire. In some embodiments, the wires may have sections where the coating is ablated and metal is exposed, as previously described. Such ablated sections may occur anywhere along the length of the active guide wire. In some embodiments, the active guide wire may have a flexibility zone and a stent zone. In some instances, the ablated sections may be provided within the stent zone. In other embodiments, the ablated sections may be provided in the flexibility zone, or anywhere else along the active guide wire.

In some embodiments, the wires may be wrapped so that they have varying degrees of floppiness. For example, a standard configuration may have the wires be rigid, or not floppy. In an intermediate configuration, the wires may be slightly floppy. In other configurations the wires may be wound to be floppy or extra floppy. The type or tightness of wire winding or braiding, or the materials of wires or coatings, may be selected to provide a desired degree of floppiness.

In some embodiments, a proximal end of the active guide wire may be formed of a plastic, such as PTFE, or any other type of polymer described elsewhere herein.

In some other embodiments, a section of the active guide wire may include a spring coil. In some implementations, the spring coil may be formed of a material that is different from the rest of the wire. In one example, the spring coil may be formed of a platinum alloy. Furthermore, in some embodiments, the active guide wire may include a hydrophilic and/or hydrophobic coating.

Figure 26:
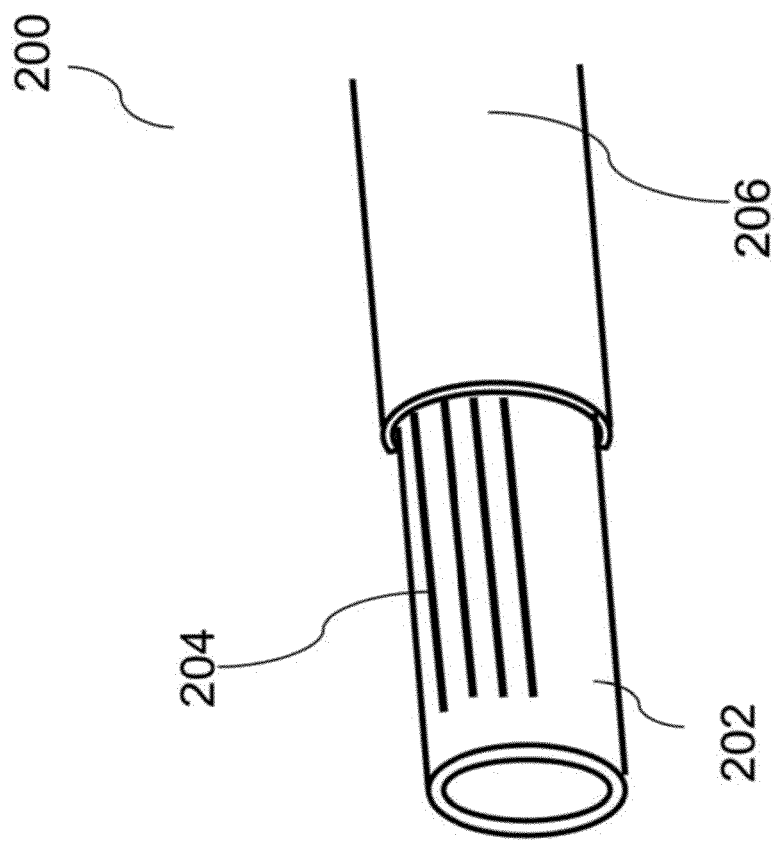
FIGS. 26-33 are diagrammatic representations of a few exemplary embodiments of the active guide wire.
Figure 27:
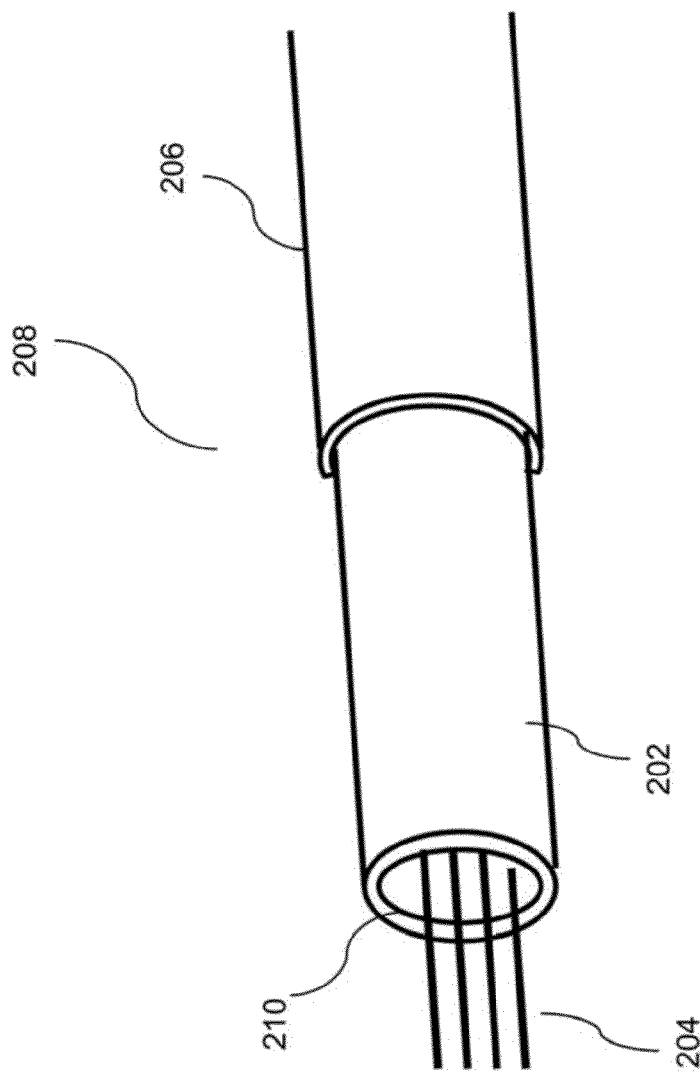
Figure 28:
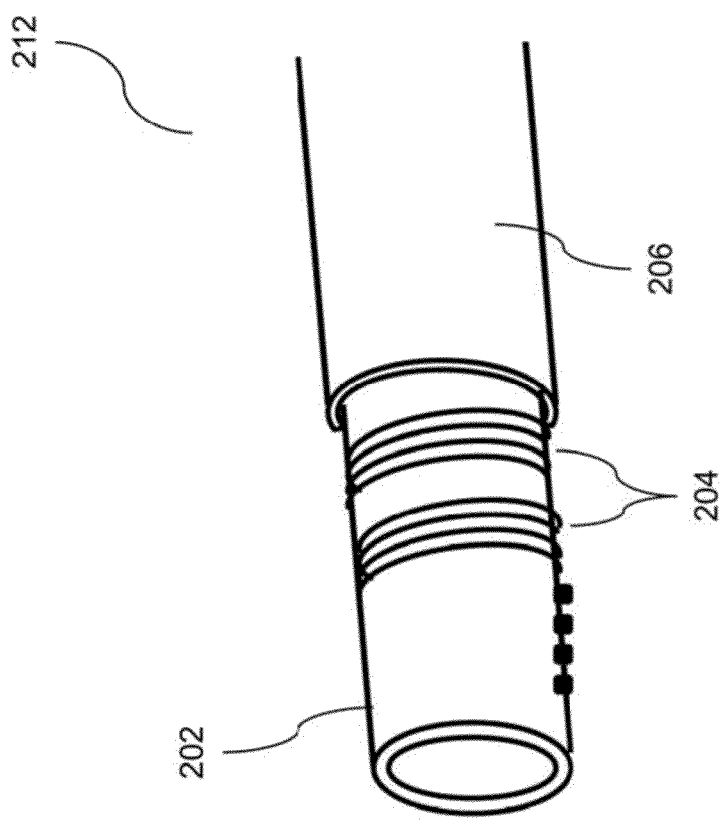

FIGS. 26-34 illustrate exemplary embodiments of active guide wires. FIG. 26 shows active guide wire 200 with core shaft 202 upon which insulated electrode wire 204 (also referred herein as conductors or conductor wire) run in parallel. Jacket 206 is disposed over the core wire and conductor assembly and reflowed for desired diameters. In another embodiment shown in FIG. 27, guide wire 208 includes conductor wires 204 that are drawn from the hollow 210 of core 202 and core 202 is covered by jacket or heat shrink 206 that can be sleeved, shrunk or extruded over the surface of the core shaft. In another embodiment of guidewire 212 as shown in FIG. 28, conductor wires 204 are wrapped around core shaft 202. The outer jacket 206 may be extruded, sleeved and reflowed over the conductor wires. The distal end of the conductor wires may be made of more flexible materials to be drawing into electrode terminals and make a floppy transition at the tip.

Figure 29:
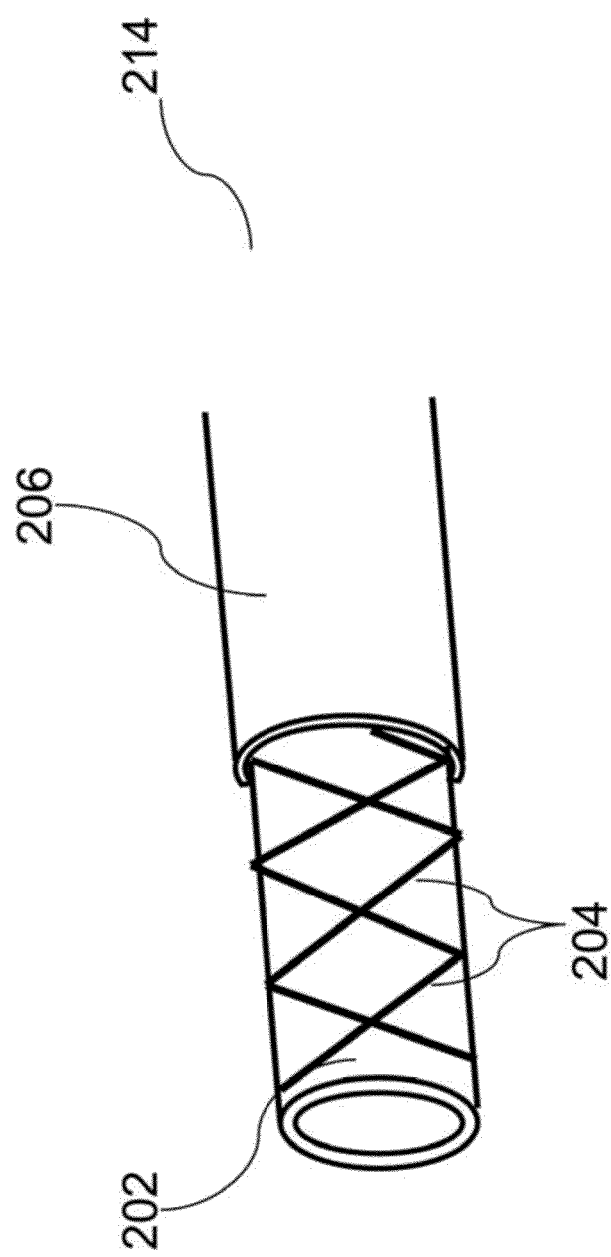
Figure 30:
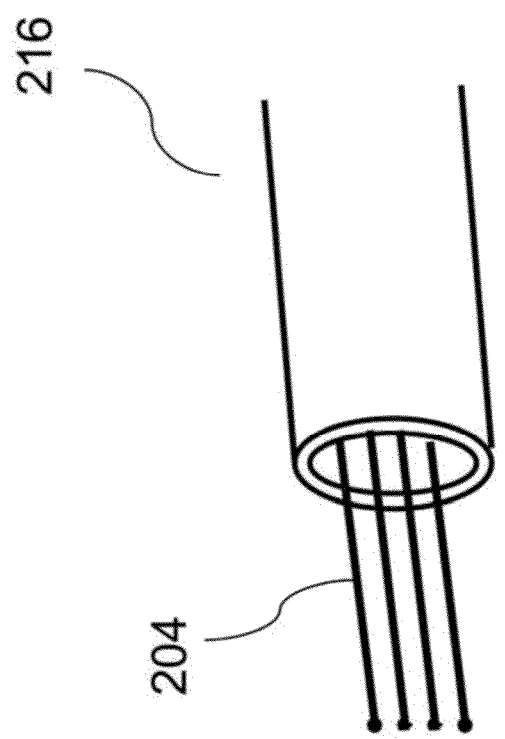
Figure 31:
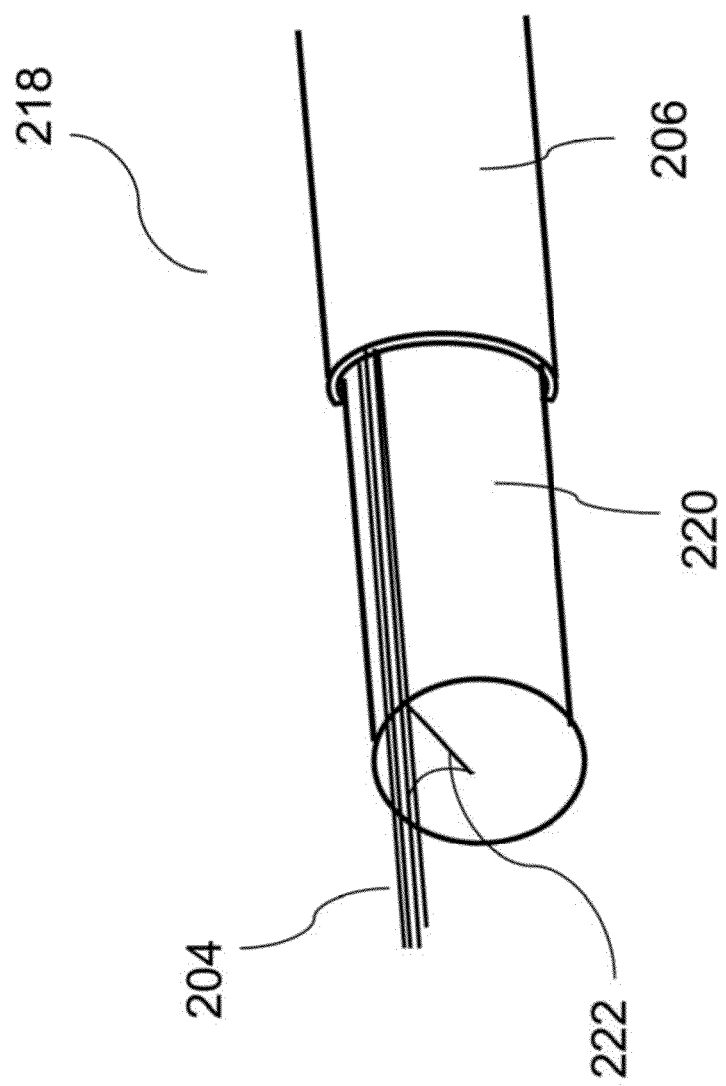
Figure 32:
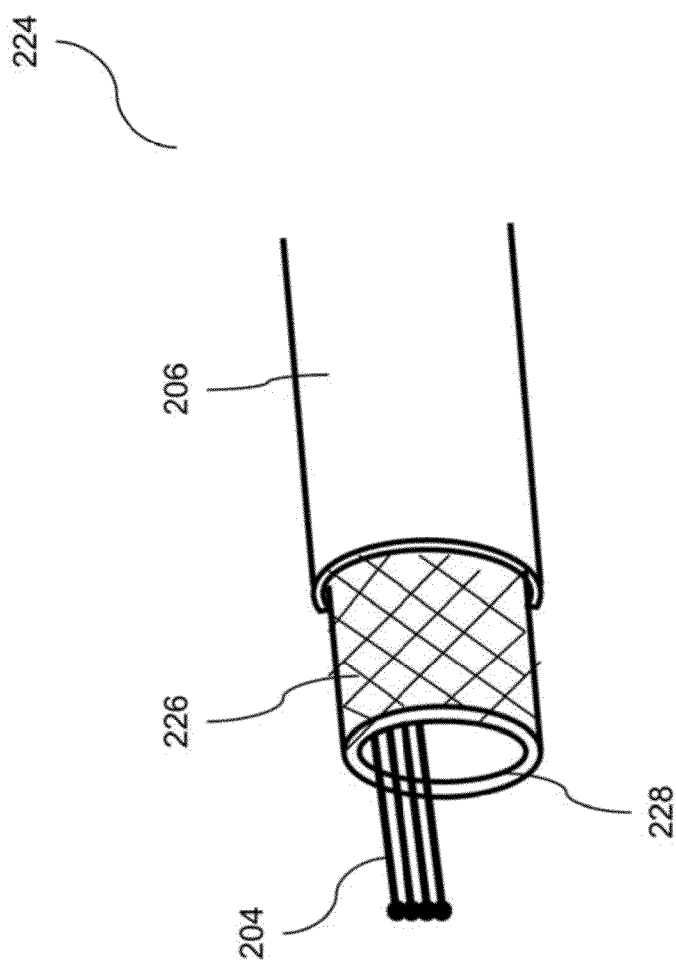
Figure 33:
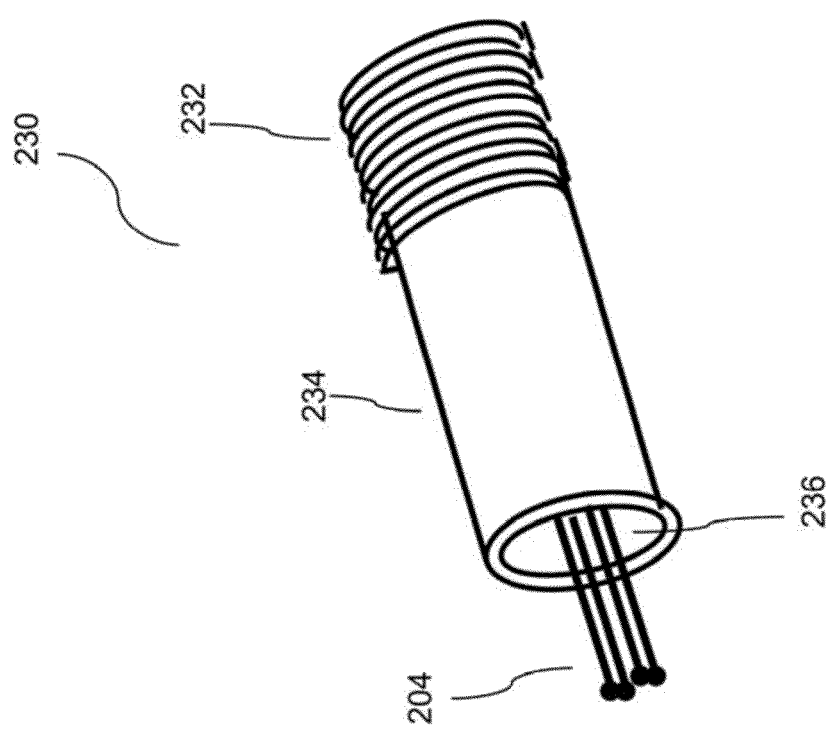

Another embodiment of guidewire 214 shown in FIG. 29 has conductor wires 204 braided over central core shaft 202. The proximal end of the conductor wires may be stiffer and the distal end may be flexible. In addition, the entire active guide wire may be made stiffer at the proximal end and flexible at the distal end. The jacket 206 may be provided to cover the braided conductor wires by any of the techniques as described in reference to other embodiments. In yet another embodiment of guidewire 216 as shown in FIG. 30, an extrusion wire may house the conductor wires 204 running internally making a main shaft and the proximal and distal ends may have a different configuration on which the electrodes may be mounted. In yet another embodiment of guidewire 218 as shown in FIG. 31, an inner extrusion shaft 220 may have a suitable groove 222 to accommodate the conductor wires 204. An outer sleeve 206 may be heat shrunk over the inner shaft. In yet another embodiment as shown in FIG. 32, the outer shaft 226 may be braided for stiffness and polymer may be reflowed over the top of the outer shaft to form a jacket 206. The conductor wires 204 may be drawn out from a central core 228. In yet another embodiment 230, a coil 232 may be sleeved over the outer shaft 234 as shown in FIG. 33, while the conductor wires 204 are drawn from a core 236 of the outer shaft.

In some embodiments, the device, which may or may not include an active guide wire, may be provided in a balloon catheter. Embodiments incorporating a balloon catheter may have some or all of the aspects described elsewhere herein, and may perform the same measurements. In some embodiments, electrodes may be provided in front of the balloon, behind the balloon, and/or on top of the balloon.

Figure 34:
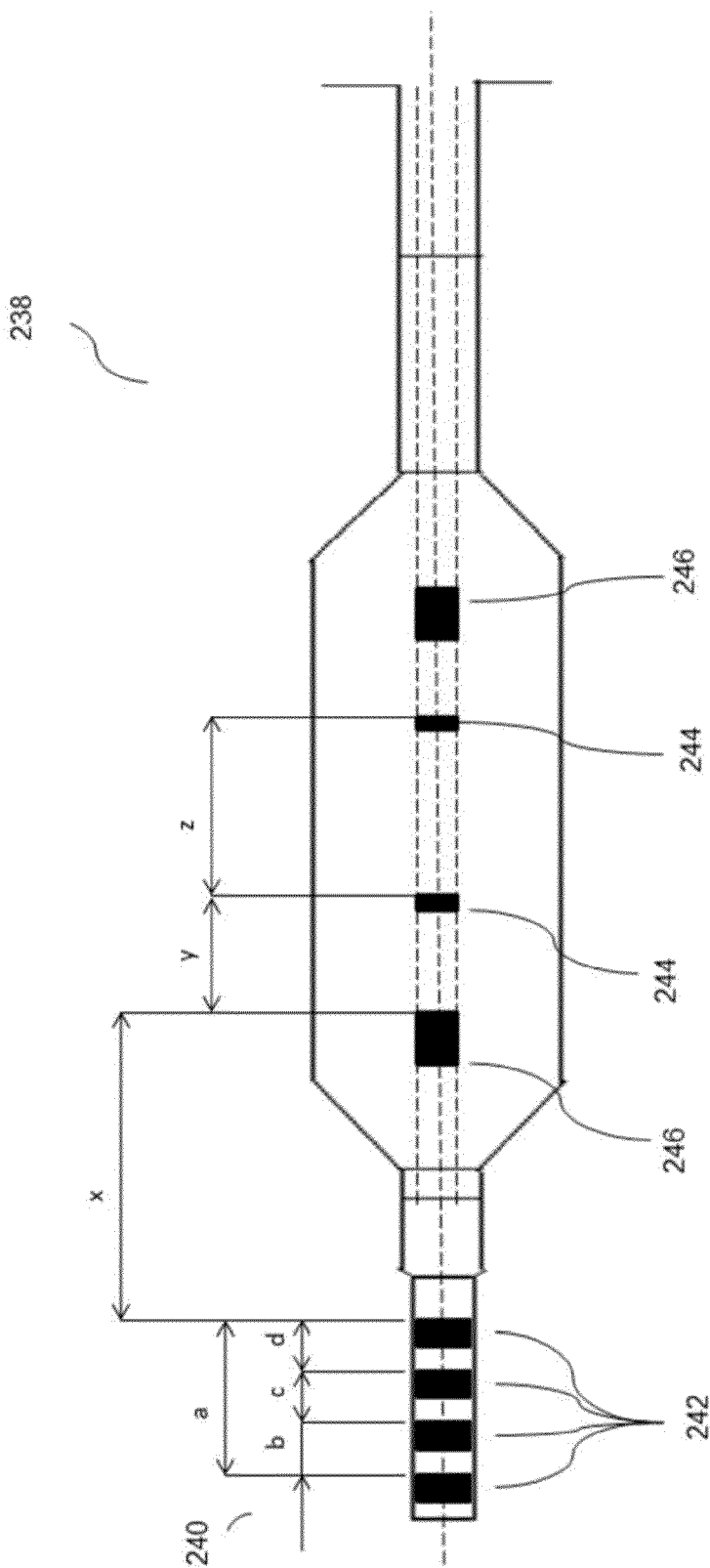
FIG. 34 is a diagrammatic representation of a balloon catheter that includes a diagnostic element.

FIG. 34 illustrates exemplary balloon catheter 238 that includes the diagnostic elements described herein. Distal end 240 of the catheter has four spaced apart electrodes 242 disposed thereon, and another set of electrodes 244 inside the balloon. The catheter also has markers 246 inside the balloon. Though only two electrodes are shown inside the balloon, there may be multiple electrodes. In this exemplary, non-limiting configuration, the distal end electrodes aid in measuring the lumen dimensions and the electrodes inside the balloon aid in determining the balloon diameter during the inflation process. The distances x, y, z and a, b, c, d as shown in the drawing, may be predetermined during the design of the balloon catheter. In another embodiment, electrodes may be present only inside the balloon. In another embodiment, electrodes may be present only outside the balloon.

A balloon catheter may also have a ring electrode disposed inside or outside the balloon, on the balloon material, for inflated dimensions. In some embodiments, the ring may be formed of a conductive material. When a conductive ring is stretched, its intrinsic resistance may increases. This can be used to measure the inflated diameter of the balloon.

The electrodes placed at the distal tip of the catheter or guide wire and the electrical conductors that connect those to the electrical hardware may behave as an antenna and pick up unwanted electro-magnetic interferences from the environment that affect the integrity of excitation and that of measured voltages. In some embodiments, the outer jacket of the catheter or a guide wire may be used as a shield against electro-magnetic interference and is connected to the GND or any fixed voltage source of the electrical hardware. Only a metallic jacket can be used as an electro-magnetic shield. In some embodiments the metallic jacket can extend along the entire length of the catheter or guide wire. In some other embodiments, the metallic jacket covers only a partial section, while the rest of the section may be covered by a non-metallic jacket such as polymer jacket. A conductive structure may be etched on the non-metallic jacket by the use of conductive ink, or, by any other means. The conductive structure may be electrically connected to the metallic jacket at the boundary edge separating the metallic and non-metallic portion of the jacket.

Embodiments of devices, systems, and methods described herein allow a practitioner to use the catheter or active guide wire or balloon catheter with no (or negligible) change in feel and no (or negligible) loss of ability to manipulate these devices as compared to the feel and manipulability of similar standard devices.

A prototype 4-electrode device (electrophysiology catheter) was created and coupled (mated) to a electrical hardware. The electrical hardware was coupled to a computer (standard). The electronics board comprised data acquisition electronics, power electronics and an electrocardiogram (ECG). Multiple glass and plastic tubes having diameters varying from 3 mm to 80 mm (measured using a vernier caliper) were fitted with simulated lesions (stenoses) that were created with various materials inserted into the tubes. The tubes with lesions were placed in saline having various concentrations. The device was inserted in each tube through each simulated lesion and the device generated electrode signals during the procedure that were transferred to the electronics board. The electronics board received the signals from the electrodes generated as the electrodes of the device sit in the simulated vessel/lesion, and/or move within the simulated vessel/lesion and transferred these signals to the data acquisition module of the electronics board. Algorithms in this embodiment were implemented on a computer to convert the signals from the device electrodes into various vessel measurements. The computer (algorithms thereof) determined the diameters and other measurements in real time and created plots of the same. The results of the experiment indicated that measurement (vessel/lesion diameter) accuracy was up to about 50 microns (micrometers).

Referring now to the embodiment comprising a first wire and a second wire, a first terminal (i.e. emitting terminal) of the first wire may be adapted as a first electrode, in some embodiments, to receive, emit or transmit a signal and/or current to a volume of interest, which may be picked up (i.e. detected and/or received) by a second terminal adapted as a second electrode (i.e. receiving terminal) of the second wire.

Figure 23:
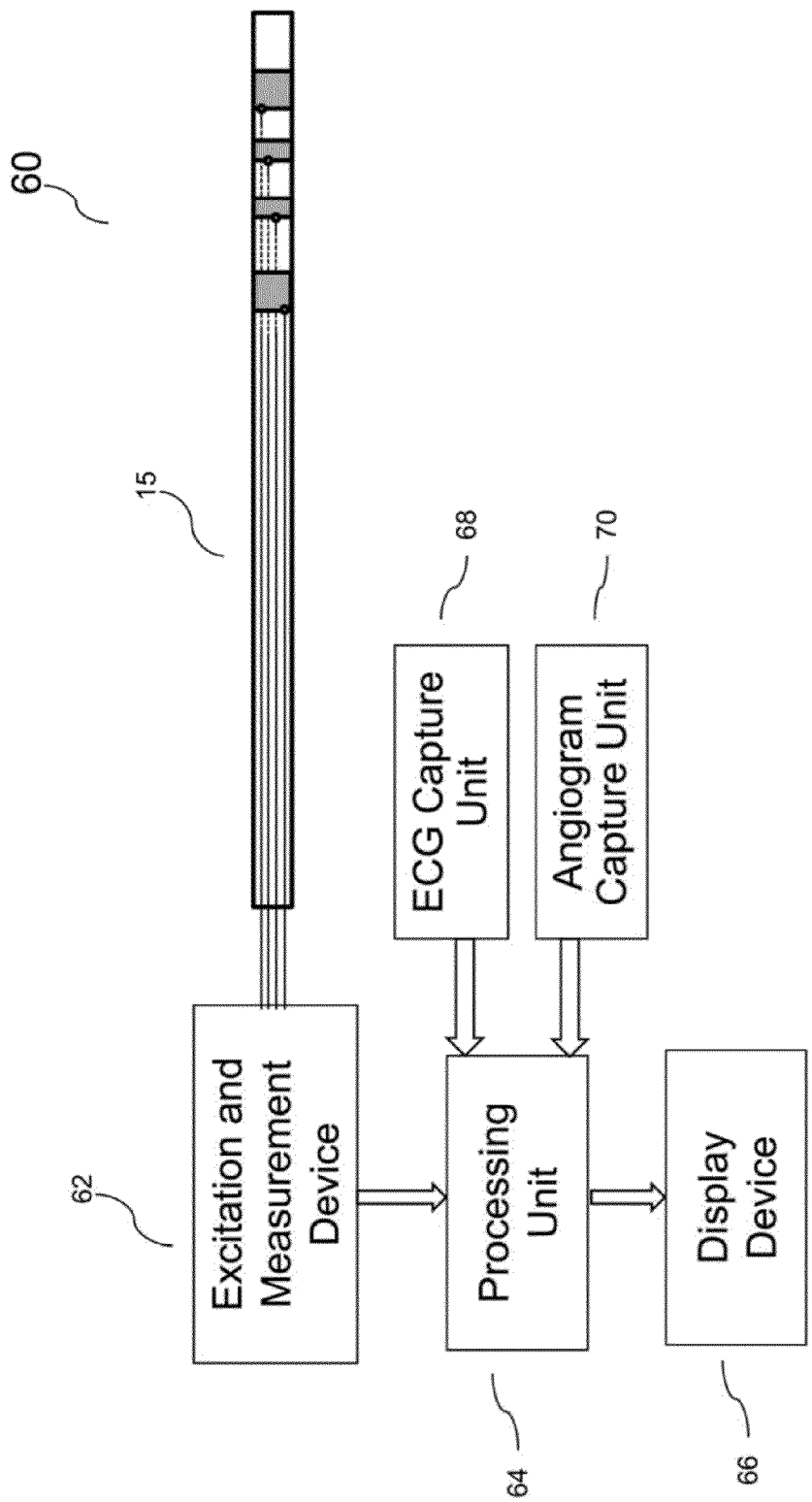
FIG. 23 is a diagrammatic representation of an exemplary embodiment of a diagnostic device.

In one embodiment, the proximal ends of the wires are connected (i.e. coupled) to a measurement device as shown in FIG. 23. A connector may be used for connecting the proximal end of each wire to the measurement device.

FIG. 23 illustrates an exemplary embodiment of a diagnostic device. Diagnostic device 60 comprises excitation and measurement device 62 adapted to receive the signals from at least one set of electrodes of diagnostic element 10 and convert (and/or transform) them to measurements and/or other anatomical information using processing unit 64. In some embodiments, excitation and measurement device 62 may receive the signals from the one set of electrodes and transform them to a visual representation of the dimensions of the anatomical feature of the subject (the anatomical feature of interest) that are displayed on display device 66. Display device 66 shows the results in different forms, dimension values, graphical representation, or visual representations overlaid on angiograms. The display device and the processor or part of the processor may be incorporated in a host computer.

Signals may be analyzed using a data acquisition module (integrated with the processing unit in the exemplary non-limiting embodiment) which can be external to a standard computer, or incorporated within a standard computer. Processing unit 64 also incorporates one or more signal processing algorithms to enable the conversion of data from the measured output voltage and current signals into desired anatomical measurements or lumen dimensions as described herein.

Processing unit 64 may also be coupled to an ECG capture unit 68 and angiogram capture unit 70 for further processing. The results from processing unit 64 can be overlaid on an angiographic image obtained from the angiogram capture unit. The ECG data from the ECG capture unit is used in an exemplary embodiment to synchronize the lumen measurements with angiographic images, examples of which are described below. Thus the devices, systems, and methods described herein can provide an imaging output, rather than only dimensions, and can superimpose the image on, for non-limiting example, an angiogram or another radiographic output image.

Figure 24:
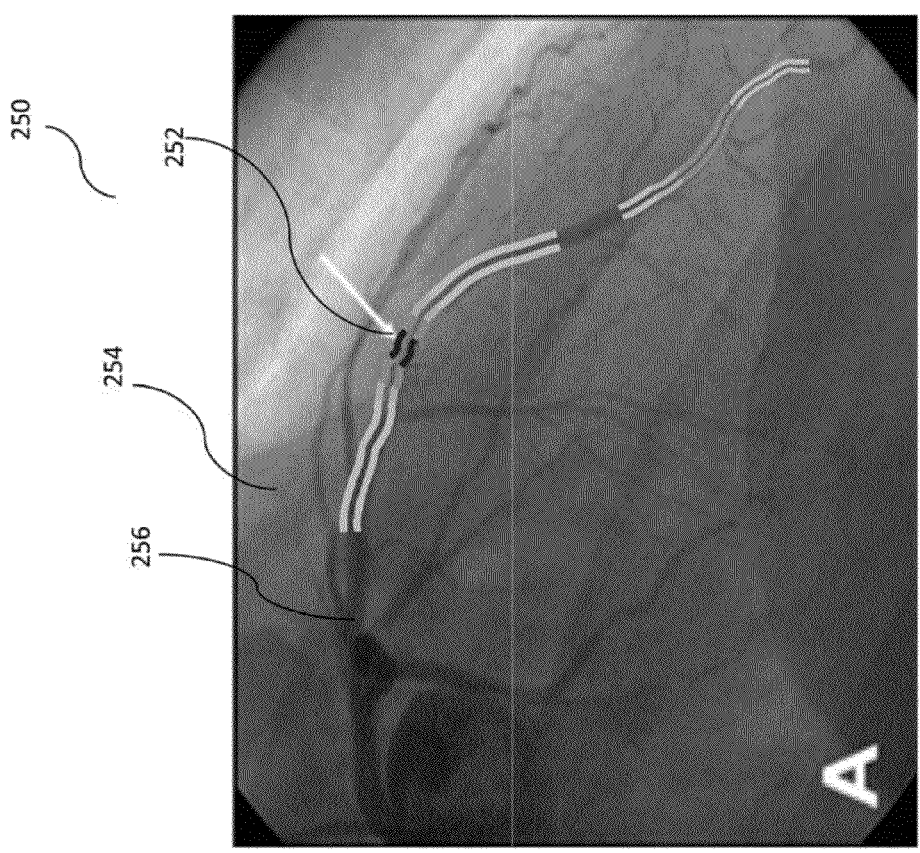
FIG. 24 shows an overlay image of an output from the measurement device and an angiogram image.

FIG. 24 shows an exemplary image superimposed on a radiographic image. Overlay 250 includes two-dimensional (2D) representation 252 of a lumen profile overlaid (or superimposed) on angiogram picture 254 of the blood vessel 256. The measurement and processing techniques enable co-registering lumen dimension information (e.g., cross sectional area) with the positional information of the endo lumen instruments, such as catheters or guide wires that have one or more radio opaque markers that can yield positional information when imaged, as is described below. These techniques are extremely useful for diagnostic guidance during a medical procedure. In some embodiments these measurements are used for determining a lumen trajectory in a 3D volume. Color coding may be provided to indicate for example a healthy region by green, a suspect region by yellow, and an alarm region by red color, other ways for providing such added information may be used as well. These techniques are more fully described below.

In some embodiments, the representation and angiogram picture may be provided on a video display. Video displays may include devices upon which information may be displayed in a manner perceptible to a user, such as, for example, a computer monitor, cathode ray tube, liquid crystal display, light emitting diode display, touchpad or touch screen display, and/or other means known in the art for emitting a visually perceptible output. Further in some embodiments, the visual representation may be monochromatic, or may include color. In some embodiments, colors or shading may be indicative of the vessel dimensions.

In some embodiments, the representations displayed on the display device may include vessel dimensions along the length of the vessel or lumen. In some embodiments, the dimensions may include vessel diameter, vessel radius, vessel circumference, or vessel cross-sectional area. The dimensions may be automatically displayed by the processing unit onto the display unit. Alternatively, the dimensions may be displayed in response to a user input. Examples of user input may include, but are not limited to, a cursor over a portion of the display (which may be controlled by a pointing device such as a mouse, trackball, joystick, touchscreen, arrow keys, remote control), or a keyboard entry. In some embodiments, the dimensions are provided in proximity to a cursor, or other user input. For example, as a user positions a mouse cursor over a portion of the visual representation, the dimension at that portion may be revealed. In other embodiments, all dimensions may be displayed.

Figure 25:
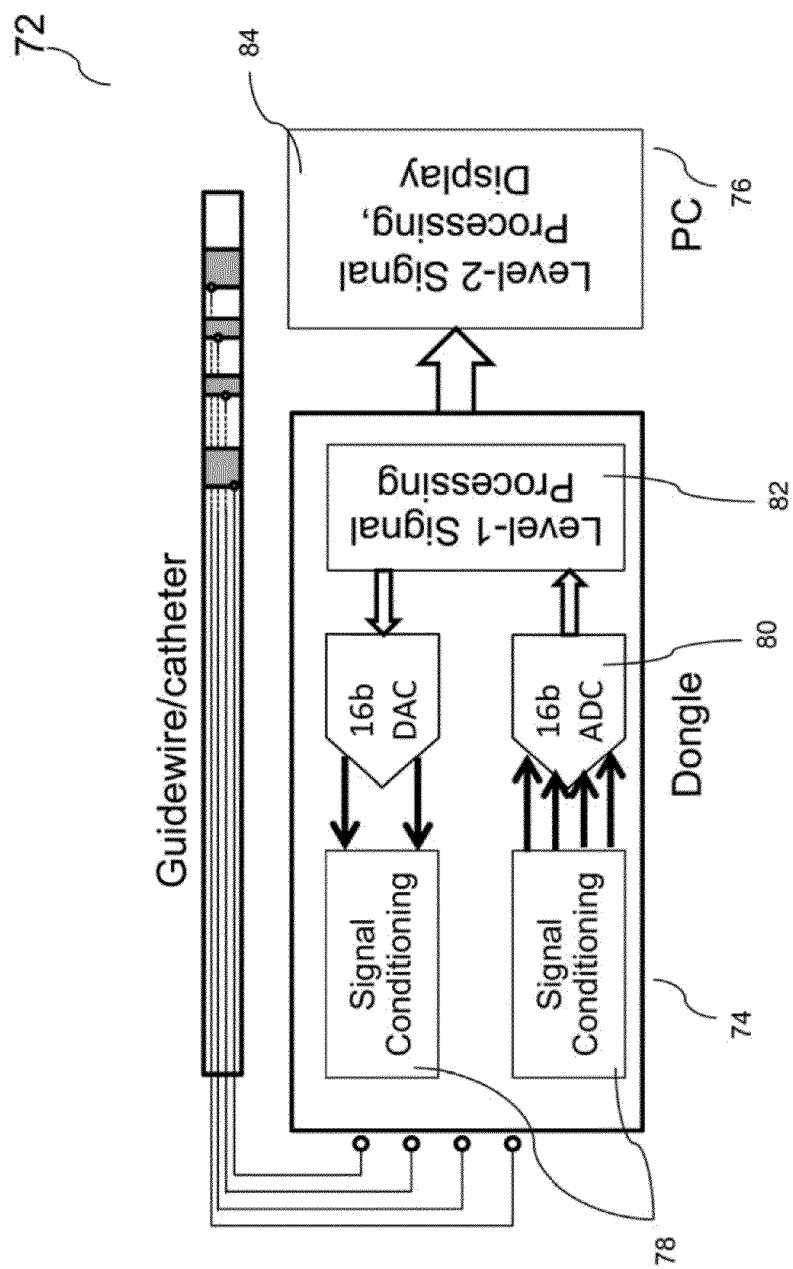
FIG. 25 is a diagrammatic representation of an exemplary embodiment of the diagnostic device showing exemplary electronics.

In one exemplary embodiment shown in FIG. 25, measurement and excitation device 62 of FIG. 23 is incorporated in dongle 74 and a host computer like a personal computer (PC) 76. The dongle 74 includes an electrical hardware that comprises signal conditioning modules 78 adapted to send and receive a signal to and from one or more electrodes. Each signal conditioner may be coupled to a high precision circuit shown general by 80 (for non-limiting example: a 16 bit data acquisition [DAQ] circuit, or an 18 bit DAQ), which converts a digital signal to an analog signal and is coupled to a level 1 signal processing unit 82. The signal may comprise any waveform known in the art. For example, the signal may comprise a sinusoidal waveform, square waveform, triangular waveform, saw tooth waveform, pulse waveform, or any other composite thereof. These data acquisition circuits further digitize the output voltages measured by the measurement devices, and the digitized signal may be processed first by a level 1 signal processing unit 82. It may be noted here that any discussion of a computer or host computer, or any specific type of network device may include, but is not limited to, a personal computer, server computer, or laptop computer; personal digital assistants (PDAs). In some embodiments, multiple devices or processors may be used. In some embodiments, various computers or processors may be specially programmed to perform one or more step or calculation or perform any algorithm, as described herein.

Signal processing unit 82 can be split into multiple sections, some residing in hardware in the dongle and the rest on a host computer as shown in FIG. 25 by a level 2 signal processing unit 84. This splitting is not mandatory and in some embodiments, signal processing units 82 and 84 may be incorporated entirely on the host computer, or signal processing units 82 and 84 may be provided entirely on a dongle. In one exemplary embodiment, a first level of the signal processor (level 1 signal processing unit) may reduce the sheer volume of data making it amenable to be transferred into a PC where the rest of the processing is done. A level 1 or a first level signal processing unit may compress the output signal such that essential information is not lost, but noise is reduced in the data, thus reducing the size of the data packet (or processed digital signals) passed to a level 2 or second level signal processing unit. In one exemplary embodiment the level 1 signal processing unit may remove the effects of device resistance and coupling.

The level 2 signal processor may be part of a computer or part of the electronics board itself. This level 2 processor may execute an algorithm or a technique or a method to determine the dimensional aspects of interest (measurements, tissue characterizations, displays of the same for non-limiting example). The level 1 and level 2 processors may be contained in a single processor which carries out both functions of the separate level 1 and level 2 processors described. Also, at least one of the processors and/or conditioner is configured and/or programmed to remove the effects (at least in part, if not entirely) of device resistance and coupling.

In one specific example the diagnostic element is incorporated into an active guide wire, also referred to herein as a smart guide wire. In one example, the active guide wire may have a pair of electrode rings at the distal end separated by a definite and unchangeable distance. In another example more pairs of electrode rings may be provided. The methods of the invention may accommodate off-axis active guide wires, blood and tissue property variations, patient-to-patient variations (such as flow, temperature, blood chemistry, etc.), and non-isotropic tissue in the wall (i.e. localized lipid pools, thrombos, calcification, etc.).

Figure 35:
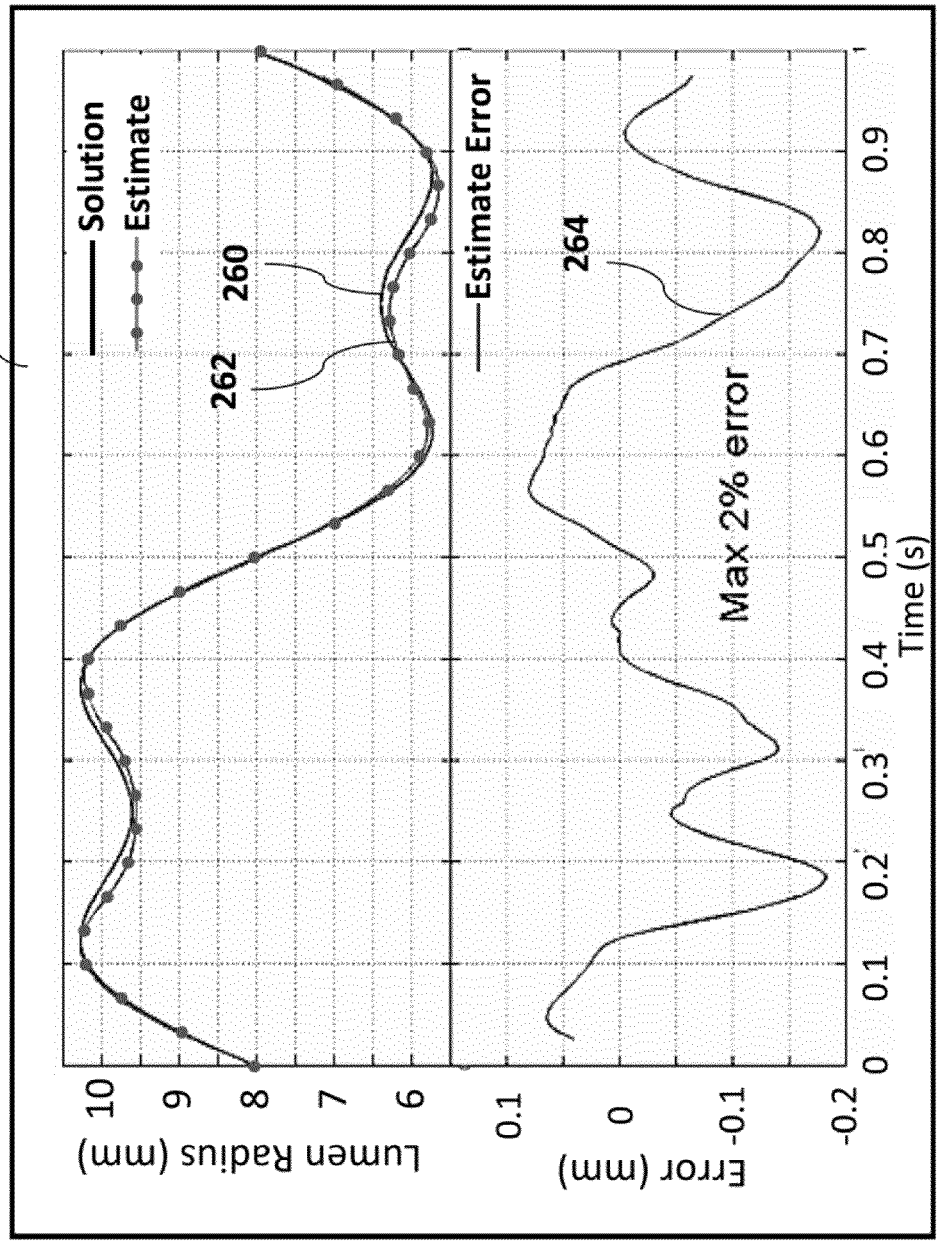
FIG. 35 is a diagrammatic representation that shows an example of raw data from vasculature in accordance with an exemplary embodiment.

FIG. 35 shows an example of data in the form of graphical output 258 from vasculature in accordance with an embodiment of the invention. Data from the vasculature was created using a Finite-Element-Modeling (FEM) technique. FEM is very accurate for any given model, and models can be arbitrarily changed to assess modes of failure and limitations. FEM uses carefully calculated electrical properties of tissues. Data was created by the FEM model, and analyzed by the algorithm (allows quantification of errors) provided in embodiments of devices, systems and methods described herein. Pulsatile flow was also created, with lumen dimension changing over time. The lumen dimensions using the device were calculated at approximately 150 times per heartbeat. This example generated four times more noise than in a real in-vivo situation as a challenge to the device, system, and methods. The results indicated a maximum of 2% error (solution versus estimate) and thus, stable tracking of the lumen. In the upper plot, the top line 260 was the actual known dimensions (radius) of the vessel across the length of the lumen (measured as a function of time). The bottom line 262 in the upper plot was the calculated (or estimated) dimensions (radius) of the vessel across the length of the lumen (measured as a function of time on the x-axis). The error of known dimensions versus the dimensions calculated by the system is shown in the lower plot 264, which indicates a maximum of a 2% error for the embodiment tested.

While the initial aspect of the disclosure may focus on determining dimensions of cardiac blood vessels, the methods can be used in other parts of the body, in other types of other vessels or organs, and may be applied for any other type of treatment or diagnostic applications for various anatomical features of a subject. For example, the methods and systems can be used in trans catheter aortic-valve implantation (TAVI). TAVI is a procedure in which a bioprosthetic valve is inserted through a catheter and implanted within the diseased native aortic valve. For a successful TAVI, two critical steps include sizing of the aortic root diameter and thereby picking the right sent size, and determining the exact location and orientation of the bioprosthetic valve with respect to the aortic root before deployment. Sizing is typically achieved by means of pre-procedural echocardiographic imaging study (either TEE or 3D echo). The echo is a separate procedure done in the echo lab and requires skilled operators. The accuracy of diameter determination is limited by quality of the image and the skill and experience of the echo technician. Currently, the position of the prosthetic valve is eyeballed angiographically and only very well trained and skilled operators are able to determine correct position. The appropriateness of the position is decided on consensus basis between operators and experienced catheter lab nurses. Once the valve is deployed there are little to none options for correction in case of erroneous placement, and furthermore the clinical repercussions are adverse. Aspects of the present technique as described herein advantageously provide a guidance system that is integrated into the current technique which can aid in sizing, positioning and deployment of the prosthetic valve.

A typical TAVI procedure begins with crossing the aortic valve by a standard 0.035" or 0.038" diameter J tip guide-wire through femoral artery access. A balloon valvuloplasty is typically performed by a balloon catheter to open up the stenotic aortic valve in preparation for the prosthetic valve deployment. This step is then followed by sliding a prosthetic deployment delivery catheter in the zone of interest and deploying the prosthetic valve. Once the valve is deployed it is checked for leakage (regurgitation) and function.

In one embodiment, the guidewires and methods herein determine the cross sectional area of the aortic system as it is being inserted across the aortic valve and thereby help in determination of the prosthetic size. Another embodiment for determining the accurate size involves placing electrodes inside the balloon catheter. As the balloon is expanded for valvuloplasty, the diameter of the balloon and hence the size of the aortic root may be determined. In yet another embodiment, the electrodes may be placed at the tip of the valvuloplasty balloon catheters. As the tip crosses the valve the electrodes can measure the cross sectional area. In addition, the electrodes can also be integrated at the tip of the prosthetic deployment catheters (at the tip) to enhance the accuracy of placement.

Figure 36:
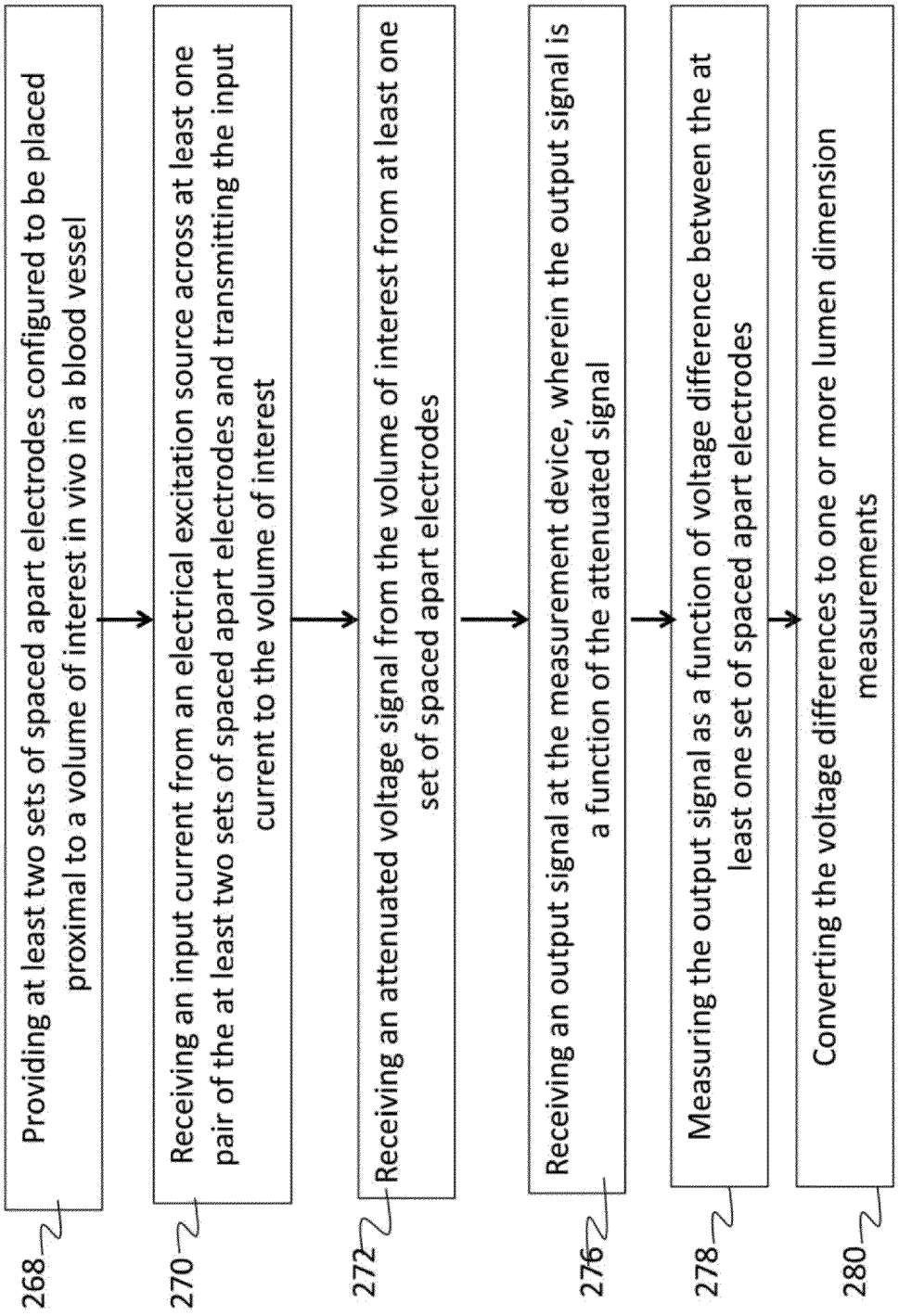
FIG. 36 is a flowchart representation of an exemplary method for determining lumen dimensions according to an aspect of the disclosure.

FIG. 36 provides a summary of one method of measuring vascular bodily lumen dimensions. The method includes a step 268 for providing at least two sets of spaced apart electrodes configured to be placed proximal to a volume of interest in vivo in a blood vessel, a step 270 for receiving an input excitation from an electrical excitation source across at least one pair of the spaced apart electrodes placed in the volume of interest, a step 272 for receiving an response voltage signal from the volume of interest from at least one set of spaced apart electrodes. The method further includes a step 276 for receiving an output signal at the measurement device, wherein the output signal is a function of the responsive voltage signal, a step 278 for measuring the output signal as a function of voltage difference between at least one set of the spaced apart electrodes; and a step 280 for converting the voltage differences to one or more lumen dimension measurements through the various techniques that have been described herein.

Thus, one aspect of the disclosure provides vascular bodily lumen dimensions. These methods and systems can be stand alone or they can be part of a larger medical procedure, some examples of which are described below.

Another aspect of the disclosure provides systems and methods for determining lumen information, such as a cross sectional area of interest, and tracking the movement of a diagnostic device relative to the area of interest. Some embodiments comprise obtaining lumen trajectory information in three dimensions with respect to a particular known reference point and also tracking the position of various diagnostic and therapeutic delivery devices (such as stent delivery systems, IVUS catheters, OCT systems, or other diagnostic devices described above) with respect to the same known reference point. The methods can therefore be used to provide precise guidance to anatomic regions of interest. Knowing the 3-D position of a diagnostic device (such as an IVUS catheter) that measures parameters such as a cross section area of a lumen and hence regions of blockages can enable marking the parameter (e.g., a blockage) along the 3D trajectory of the device on a visual device showing the lumen. Once marked, a stent delivery system can then be guided to the marked region precisely, accurately placing the stent delivery system at the location of interest, in this instance the location of the blockage.

This aspect also includes methods to obtain lumen trajectory in 3D of diagnostic devices that pass through a vasculature, and further methods to track the devices and stitch the parametric information measured by the diagnostic devices with positional information obtained by the guidance system. Furthermore, a method to use the described guidance system to guide any endo luminal therapeutic device to points of interest in the vasculature is disclosed.

Figure 37:
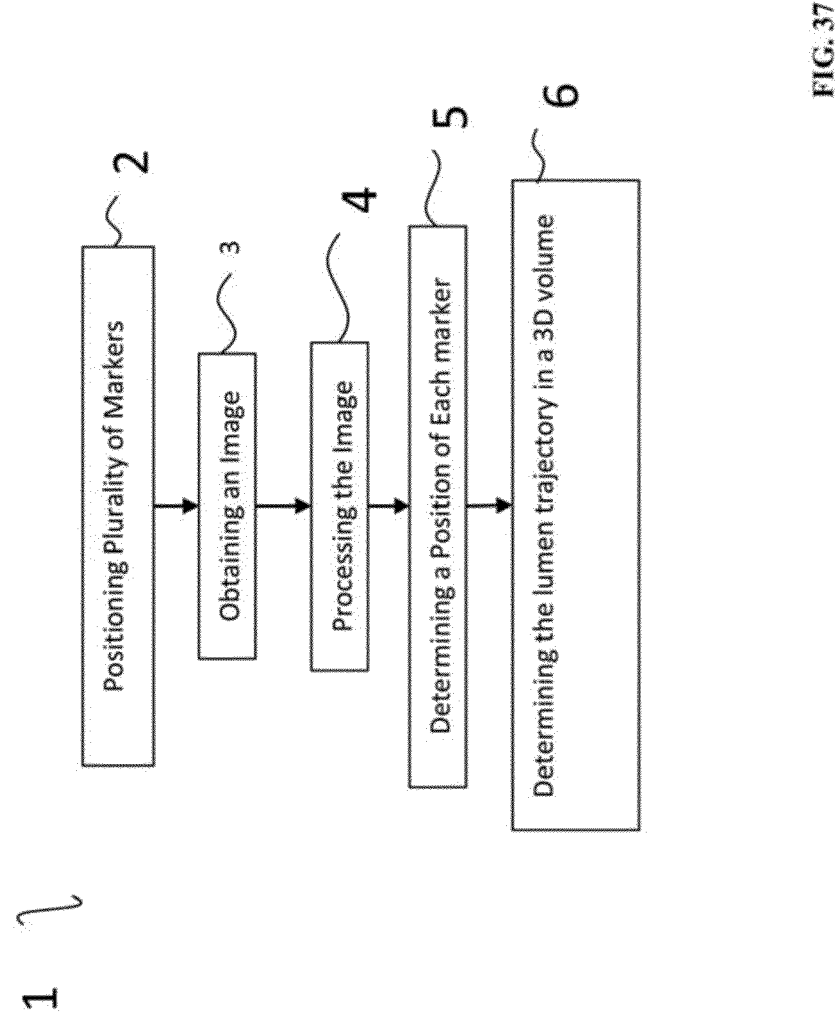
FIGS. 37 and 38 illustrate exemplary methods of determining a lumen trajectory in a 3D volume.

In one embodiment a method determines a lumen trajectory in a 3D volume. An exemplary method is shown in FIG. 37. Method 1 comprises the step of positioning a plurality of markers in vivo in a lumen 2. The plurality of markers may be advantageously present on a suitable endo-lumen instrument configured to be inserted in-vivo. "Endo-lumen instrument" as used herein includes any instrument that is adapted to make measurements, or observations of lumen, or provide guidance to such a measurement or observation instrument, for example without limitation, a wire, a guide wire, a catheter, etc. An exemplary wire for this purpose is a guide wire that is used to deliver stents. Other such exemplary wires may become obvious to one skilled in the art, and are contemplated to be within the scope of the disclosure. The guidewires described above with electrodes disposed thereon are merely examples of markers that can be positioned within a lumen in step 2.

Each marker is characterized by an original identity. The "identity" of each marker includes parameters used to identify the markers, such as a serial number of a particular marker, the position of the marker, distance from at least an end (e.g., distal or proximal end) of the device, distance from the closest adjacent markers, width of the marker, direction of orientation of the marker with reference to a reference frame, etc., and combinations thereof. Markers useful in the disclosure include those that can become identifiable under imaging techniques or image processing techniques. The imaging modalities known in the art are quite varied, and markers may be designed to include those that can be identified under one or more imaging modalities. For example, one useful marker may be a radio-opaque material that can be imaged using X-Rays. In another exemplary embodiment, the plurality of markers may include at least two spaced apart electrodes configured to give rise to a signal when excited with a pulse. In yet another exemplary embodiment, the plurality of markers may include a dye that fluoresces in the near infrared region of the wavelength spectrum upon suitable excitation, and hence, can be observed using an infrared spectrophotometer. Each marker may include a combination of materials to render it capable of being observed by multiple imaging techniques. Thus, one marker may comprise a radio-opaque material and two spaced apart electrodes. Further, the plurality of markers may include a combination of such materials. Hence, in an exemplary embodiment, one marker may comprise of a radio-opaque material, while another marker may be two spaced apart electrodes.

Method 1 also comprises the step of obtaining an image of the plurality of markers 3. The manner of obtaining an image will depend on the nature of the markers involved. Subsequently, method 1 involves processing the image 4. The processing is done to determine at least an observed identity for each of the plurality of markers. The observed identity provides current information of the markers in an in vivo position. The processing of the image also provides an observed spacing between at least two markers from the plurality of markers. Processing of the image 4 may also be undertaken to identify other anatomical landmarks, such as identity of the lumen near the marker, identifying cells or blockages, bifurcation of arteries, etc.

Method 1 also includes determining a position of each marker in a 3D space 15. The position of each marker defines a region of lumen based on the observed identity, the observed spacing, and the original identity of each of the plurality of markers. For example, in one exemplary embodiment, if the original identity of two markers defined by serial numbers M1 and M2 that are spaced apart from each other by a certain distance d1 wherein both markers are facing the same direction, and the observed identity shows that the distance between has been reduced to d2, and one of the markers is twisted away by a certain angle relative to the other marker, then the trajectory in 3D space between the two markers may be determined using mathematical techniques such as interpolation. Mathematical techniques may be applied, such as maintaining the same relative distance as compared to the original relative distance would indicate a linear path with little or no twists, while a decrease in relative distance would indicate a tortuous path undertaken by the wire.

Method 1 further comprises determining the lumen trajectory in a 3D volume based on the position of each marker 6. Using the processed image from step 16 and the position of each marker in a 3D space from step 5, the entire lumen trajectory in a 3D volume may be reconstructed using techniques known in the art, such as interpolation. Such interpolation techniques may take advantage of the physical properties of the lumen trajectory device as well as the orientation each of the markers. The reconstruction may be done using an appropriate computing device with a processor. The computing device may be a personal computer, and may be capable of providing the lumen trajectory in a 3D volume online or in an offline manner.

Figure 38:
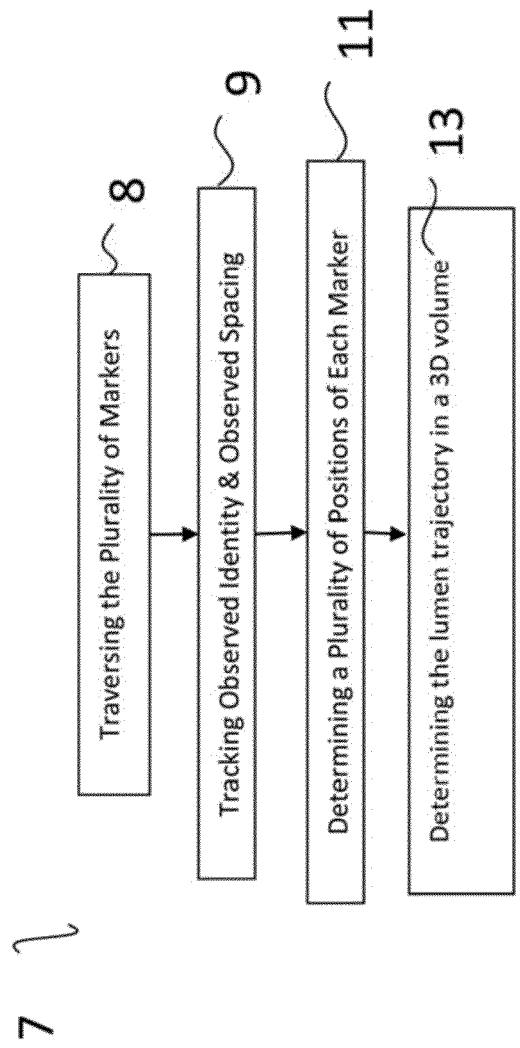

FIG. 38 shows further exemplary steps 7 of some exemplary methods of the disclosure. Step 8 comprises traversing the plurality of markers through the volume of interest in a lumen. The volume of interest in a lumen may be identified from some prior information, or may be identified based on immediate observations, such as those by an expert like a surgeon or an experienced technician. An exemplary volume of interest may be a diseased artery. Another exemplary volume of interest may be an aneurysm in the aorta. Traversing may be achieved by known methods in the art, such as manually actuating the device comprising the plurality of markers, or actuating the device using a controller mechanism such as, for example, a stepper motor.

The method 7 optionally comprises tracking the observed identity and the observed spacing while traversing the plurality of markers, as shown in step 9. This may then be recorded as observed identity and observed spacing. Tracking the observed identity and the observed spacing may be conducted using the relevant imaging techniques, as described herein. The tracking may be achieved by obtaining a series of images at periodic intervals, and noting the time associated with each image. Alternately, if the imaging modalities allows for it (such as fluoroscopy), a continuous image, such as a movie slice, may be obtained, and then the tracking may be done using the different frames of the movie slice. Thus, each data point extracted or obtained gives rise to an observed identity and an observed spacing. The periodicity of obtaining image and sampling rate may depend on a variety of factors, and may include, for example, the nature of the imaging modality, the computing power of the processor, the nature of information required, the condition of the lumen being observed, and the like, and combinations thereof.

An exemplary X-ray image of a guidewire G inserted through a guide catheter C with several markers M (only four are labeled) is shown in the left of FIG. 38A. An image analysis algorithm was run that scans the individual pixels in each frame (picture) to identify the pixel grade and identify those that belong to the marker and reject others that do not correspond to the markers. Discriminators can be built into the algorithms that help the algorithm hone in on markers of interest and reject the rest of the markers that may be present in the field of view. An example of a discriminator can be the size of the marker, another example can be distance between markers in a particular angle of view, yet another discriminator is the constraint that all markers are on a smooth curve. A circle was placed on identified markers in the right side of FIG. 38A. As the guidewire traversed longitudinally through the inner diameter of catheter C a series of picture frames are generated and the image identification algorithm identifies markers in each picture frame. Sequences of images in FIG. 38B show different frames obtained as the guidewire is being advanced through catheter C. The different markers were identified by the image processing algorithm in each of the frames. Thus, the position of markers in each frame is located. FIG. 38C shows two views of the same wire with markers. It can be seen that in the second view, the apparent relative spacing between markers changes. For example the markers numbered 2 and 3 appear closer in the first view (on the left) even though their physical separation in 3D is exactly the same. The actual physical distance between the markers is known a priori. Further, the mapping of pixels to physical distances was found to be about 0.25 mm per pixel in this example. Using this information, the trajectory of the endolumen device can be tracked by first estimating the trajectory of each inter marker segment, and integrating all the segments in a frame and then from frame to frame.

Subsequently, method 7 in FIG. 38 comprises determining a plurality of positions of each marker in a 3D space 11 that defines the volume of interest based on the observed identity, the observed spacing, and the original identity of each of the plurality of markers. As already described herein, the observed identity and observed spacing and original identity and spacing may be used effectively to reconstruct a lumen trajectory in which the endoluminal device traversed. Thus, the method 7 further comprises determining the lumen trajectory in a 3D volume 13 based on the plurality of positions of each marker. Such a lumen trajectory in a 3D volume may be determined offline from the imaging, or on a substantially real-time basis, depending on the computing ability available.

The positions of the markers are determined with respect to the origin of each image. However, to guide other endoluminal devices after a particular lumen trajectory is known it is essential to mark the position of the trajectory with respect to a fixed reference. Additionally, the known size of the reference element can enable calibration of observed markers and distances to accurate physical dimensions. Methods herein further involve the use of a reference component, such as a patch positioned on the skin of the subject that is used as a reference (origin) and calibration of all observations. The reference component comprises at least one reference marker. In some embodiments, by virtue of its precise 2-dimensional construction, a reference patch allows the mapping of the number of pixels in an image to physical dimensions. Further, reference patches can also account for movements by the subject during measurement, which may otherwise render measurements difficult to interpret. A reference patch allows for any offsets and deviations in measurements to be accounted for, thus giving rise to more accurate lumen trajectory in a 3D volume. The reference component, such as a patch, may be present ex-vivo. In a typical use situation, the exact position, direction of orientation, width, depth and other dimensions of the reference patch is known at all times, and this measurement is taken along with the measurement of the at least two markers of the lumen trajectory device to determine the position of each such marker accurately. In some instances, the reference patch may be placed on the subject. In other embodiments the reference patch may be attached to the operating table. A reference patch may be similar to the at least two markers mentioned earlier in its composition, and may be a radio-opaque material, at least two spaced electrodes, a fluorescent dye, and the like, and combinations thereof. In one specific embodiment, the reference patch is a radio-opaque material that is capable of being imaged using X-Ray modality. In another embodiment, the reference patch is at least two spaced electrodes. The shapes of the patch markers may be varied to allow easier determination of orientation of the patch and hence the 2D image in relation to the subject.

Methods herein may further be used in conjunction with other techniques currently being used. For instance, the lumen trajectory in a 3D volume obtained from methods herein may be overlaid onto an angiogram obtained independently. In another exemplary embodiment, the processing of the image in step 4 of method 1 in FIG. 37 is done using an angiogram obtained independently and/or simultaneously.

Figure 39:
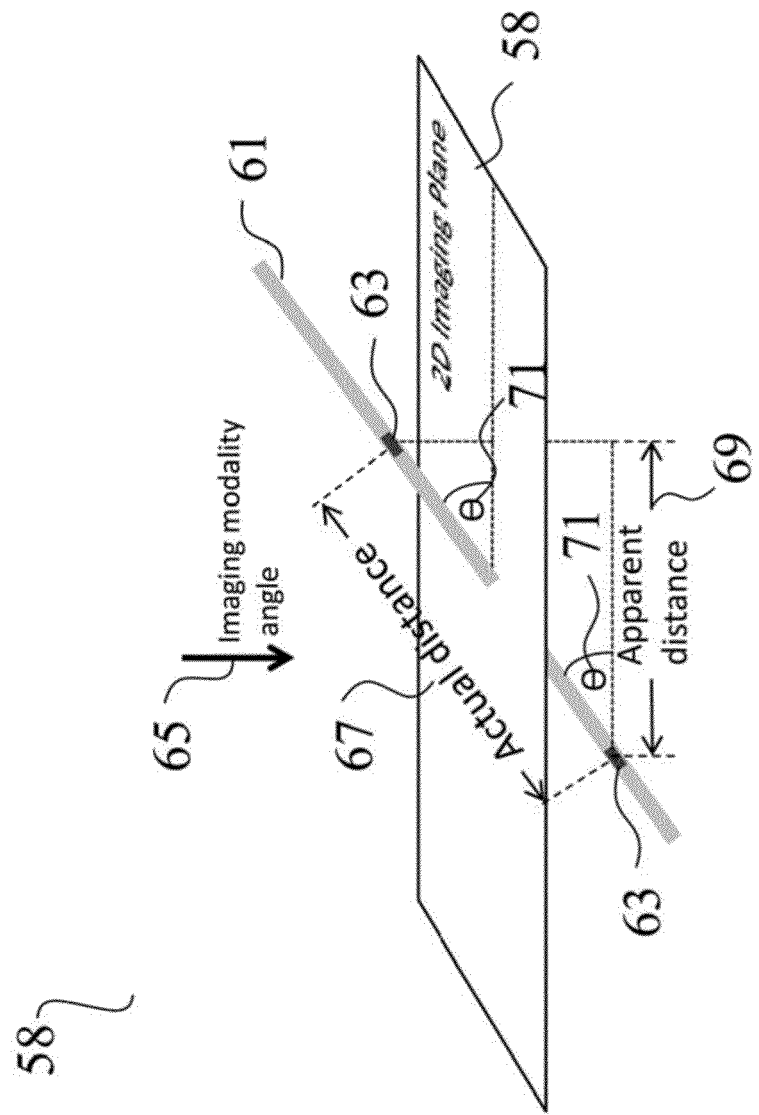
FIG. 39 shows a specific embodiment of the application of the method of disclosure to obtain a lumen trajectory in a 3D volume.

FIG. 39 illustrates an exemplary method of use 58, wherein the method is applied in a specific embodiment in determining actual dimensions to determine lumen trajectory. FIG. 39 shows the endo-lumen instrument 61 having two markers 63. However, one skilled in the art will understand this principle can be extended to any number of markers on any endo-lumen instrument, and even to multiple endo-lumen instruments, each having a plurality of markers. The markers 63 are viewed by a suitable imaging modality at a particular angle, represented by numeral 65. As stated herein, suitable imaging modality may include, for example, X-Ray technique. The actual distance between the markers 63, represented by numeral 67 in FIG. 39, is already known from the specification of the endo-lumen instrument, as provided by, for example a manufacturer, or may even be made available by a suitable independent measurement technique. The actual distance as measured by the imaging modality 69 will be different from the actual distance 67, due to angle 71 between the axis of viewing by the imaging modality and the axis of the 2-D plane of the endo-lumen instrument 63. When the apparent distance between two markers in 2D is less than the expected distance in a planar layout, it can be inferred that the endo-lumen instrument is going into the plane or coming out of the plane. The angle, theta (θ), 71 which it subtends to the 2D plane is given by $$\cos(\Theta) = \frac{\text{Apparent distance between markers}}{\text{Actual distance between markers}} \quad (4)$$

The actual distance 67 between two markers in a linear layout is known in absolute terms a priori. However, all measurements made from the 2D image are typically viewed in terms of number of pixels on a suitable viewing medium, such as a screen. There is a need to convert the distances measured in terms of pixels into real world dimensions (such as millimeters). A mapping of pixels to millimeters is needed to compute 3D mapping. This mapping depends upon various parameters specific to the imaging modality used, such as the picture resolution used by an X-Ray scanner, X-ray zoom factor used, and the like. In one exemplary embodiment, the pixels to millimeters mapping can be obtained by at least one of: (i) The zoom and picture resolution (rows & columns) of the X-ray image as obtained from the imaging device; (ii) Analysis of the 2D picture of the "reference patch" placed on any plane whose marker spacing is known a priori. By measuring patch marker distances along rows and columns, and the angle between rows and columns, it is possible to derive the number of pixels per actual length (for example 1 mm).

In some aspects the endoluman device is a non-elastic guidewire or other medical device, and the methods take advantage of the nature of the non-elastic nature of the guidewire. If a portion of the wire is tracked and found to advance or retract by a certain distance along the lumen trajectory, then the entire guidewire can be assumed to advance or retract by the same distance. Thus, even if the markers in certain regions cannot be tracked accurately due to reasons such as occlusion, interference from other objects and lack of clarity in the X-Ray image, the tracking of a subset of markers would be sufficient to estimate the movement of all the markers. If the wire is being advanced and if the distal markers are obscured, one would not be able to determine the exact 3D trajectory of the lumen in the newly visited region into which the distal part of the wire is entering. However, the distance by which the distal markers advance into the lumen is still obtainable, and is thus clinically useful. When markers in the newly visited region eventually become visible, the 3D trajectory of the lumen can then be re-constructed.

Another aspect of the algorithm determines the amount by which a wire or catheter is advanced into or retracted from a lumen without necessarily re-constructing the 3-D path of the lumen. This is done by tracking a subset of markers anywhere along the wire. Since the overall length of the wire of catheter does not change (since it is inelastic), the amount of advancement or retraction of any section of the wire reasonably close to the lumen site can be reasonably approximated as the amount of advancement or retraction of the distal end of the wire or catheter. This result of this aspect of the algorithm is similar to other prior art techniques such as IVUS that use motorized push and pull-back to determine the amount of advancement or retraction. Due to the elastic and compliant nature these prior art techniques are less accurate. This is because the movement measurements are made at the proximal end, while the movement required to be measured is the distal end. As the wire is pushed, the blood vessels through which the wire is inserted may stretch a little. Small changes in patient position, the heartbeat of the patient, and the breathing of the patient are other factors that can increase the inaccuracies of these methods. On the other hand, in this embodiment, the markers being tracked are very close to the anatomy of interest, which would significantly reduce the inaccuracies. Further, additional aspects of the methods herein compensate for effects of heartbeat to further improve the inaccuracies.

Yet another aspect of the algorithm is to estimate and compensate for the changes in lumen trajectory due to the beating of the heart. The beating of the heart causes a near-periodic change in the lumen trajectory. Only lumen trajectories estimated at the same phase of the heartbeat are completely consistent. Hence tracking of the lumen trajectory is done separately for different phases of the heartbeat. At other phases, the lumen trajectory would be slightly different, but correlated. The effect of the heartbeat in the change in lumen trajectory is more large scale in nature. There is little local change in the trajectory, and more of overall shifts in the entire trajectory. This nature of shifting trajectory can again be modeled and estimated from measurements. This approach leads to an overall improvement in accuracy compared to determining lumen trajectory independently for each phase of the heartbeat.

As the endo-lumen device is advanced into the blood vessel, for a given phase of the heartbeat, the lumen trajectory is a fixed while the markers move along the trajectory. Thus the same section of the lumen trajectory is visited by multiple markers. In other words, there is a constraint on a marker to follow the preceding marker along a single lumen trajectory. This can be exploited to obtain a more robust estimate for the section of the lumen trajectory that is visited by multiple markers since more information is available for the section.

Method 1 can be advantageously implemented using a suitable algorithm that works with the imaging modality in use. Fine tuning of the image to determine the position more accurately may be done using the algorithm to obtain a very clear and accurate lumen trajectory in a 3D volume.

Figure 40:
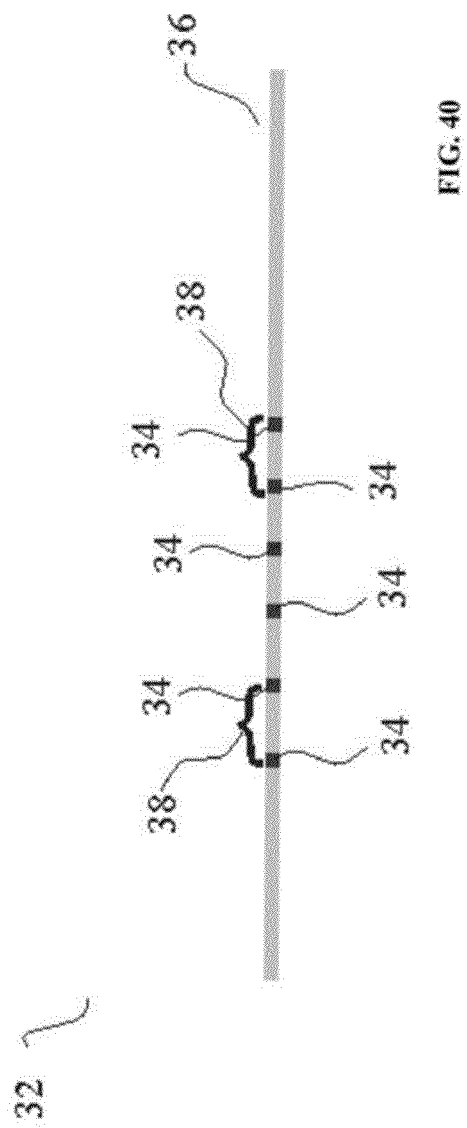
FIG. 40 shows a schematic of an exemplary lumen trajectory device of the disclosure.

FIG. 40 shows a schematic of an exemplary lumen trajectory device 32. The lumen trajectory device comprises a plurality of markers 34 positioned at predefined locations on wire 36 and configured to be placed in vivo in a lumen. The spacing between each marker 38 is known when all the markers are laid in a linear configuration. Other exemplary lumen devices and methods of use that can be used with the methods and systems herein are described above.

The lumen trajectory device is typically an endo-lumen instrument on which the markers are disposed. In one specific embodiment, the endo-lumen instrument is a guide wire with radio-opaque markers. In another embodiment the endolumen instrument is a stent delivery catheter that already has two radio-opaque markers that demarcate the ends of the balloon. In yet another embodiment the endolumen device is an IVUS catheter, known in the art, which also has radio-opaque markers that can be tracked on an X-ray image.

In some embodiments, the markers may be in a simple band shaped form, as shown in FIG. 40. Other geometric shapes for the markers are also contemplated to be within the scope of the invention. In one specific embodiment, the markers are in the form of a grid pattern, comprising a plurality of smaller shapes, all of them combining to form a marker.

Figure 41:
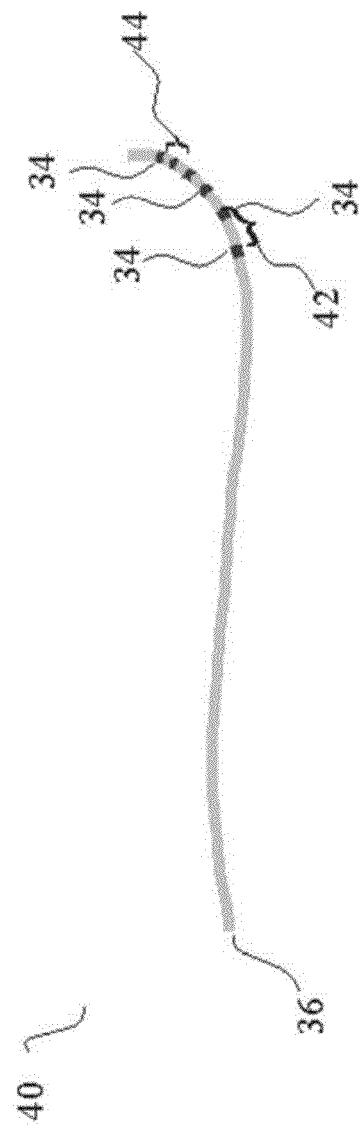
FIG. 41 shows an exemplary lumen trajectory device of the disclosure in a simulated use situation.

FIG. 41 shows lumen trajectory device 40 in a simulated method of use, wherein the device is allowed to take a tortuous path that is representative of an artery (not shown). Here, it can be seen that the distance between two markers in a linear portion 42 is similar to the spacing 38 in FIG. 40, whereas the spacing between markers 34 in the tortuous region 44 is different from that of the spacing 34 in FIG. 41.

Figure 42:
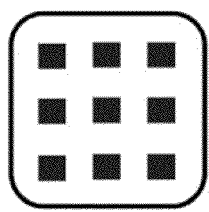
FIG. 42 shows one exemplary arrangement of one reference patch with markers on it.

For the reference patch, FIG. 42 shows one exemplary arrangement of one reference marker, wherein the marker is in the form of a grid pattern.

Figure 43:
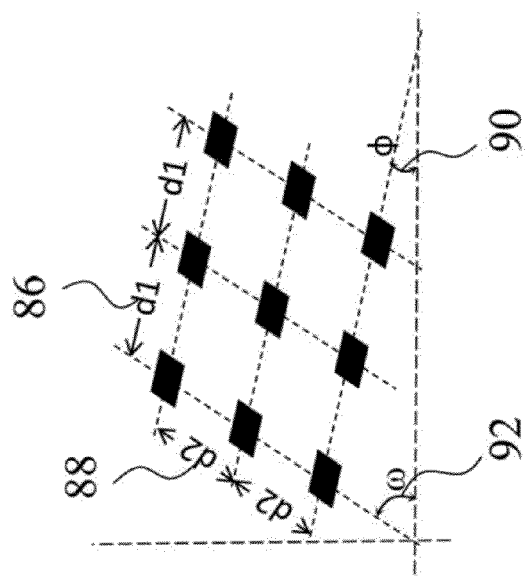
FIG. 43 shows the exemplary arrangement of one reference patch with markers on it in use situation.

In an exemplary method of use, if the plane of viewing by an imaging modality is perpendicular to the plane of the marker, then the image appears as shown in FIG. 42. However, if the lumen trajectory device takes a tortuous path, and consequently is bent, or the viewing angle of the imaging modality is altered, the image appears as shown in FIG. 43, and represented by numeral 47. Since the grid covers 2 dimensions, it is possible to determine the 3D angle of tilt of the lumen trajectory device. Once the tilt angle is known, it can be compensated for and used as a reference for distances. The same patch can also be used as a positional reference to obtain orientation and bearing at any time even when the imaging modality angle and region changes.

As noted herein, the image from the imaging modality is viewed on a suitable viewing medium such as a screen, wherein it appears in the form of pixels. If measured distances 'd1' 74 and 'd2' 88 are known in terms of pixels, and if angles 92 and 90 are measured, and if the actual spacing between the markers is 'a' (in physical dimensions such as millimeters), the pixels per unit distance (pixels per mm) may be determined. Following this, using mathematical transformation involving pitch, roll and yaw of the optical viewing modality, the measurements of d1, d2, angles 92 and 90 may be obtained to a high degree of accuracy. In other embodiments, only one marker may be used on the reference patch. In this case, the apparent shape of the marker would depend on the angle from which it is viewed. By measuring the apparent dimensions and the angular orientation of the shape itself, it viewing angle as well as the pixels per unit distance may be determined. Using more markers improves the robustness of this determination. As such, it is to be understood that one or more markers may be used for the reference patch.

When the apparent distance between two markers in 2D is less than the expected distance in a planar layout, there is an ambiguity between whether the endo-lumen instrument is going into the plane or coming out of the plane. In such cases, parameters specific to the volume of interest such as anatomical information as well as the lumen trajectory device parameters such as smooth continuity constraints of the endo-lumen instrument can be used to resolve the ambiguity.

Figure 44:
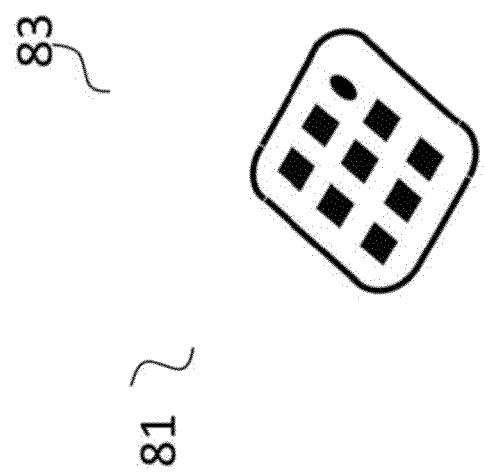
FIG. 44 shows another exemplary arrangement of one reference patch with markers on it.

The lumen trajectory device of the invention 23 further comprises a reference patch. The reference patch may be present at a pre-determined position place ex vivo in the field of view of an imaging device used for imaging the lumen trajectory device. In some embodiments, the reference patch comprises of one or more calibration electrodes arranged in a pre-determined pattern, wherein in one exemplary embodiment, the pre-determined pattern is a grid pattern. FIG. 44 shows another exemplary arrangement of a reference patch 81 on the lumen trajectory device of the invention, wherein the markers are in the form of a grid pattern, and the pattern comprises one shape 83 that is different from the rest of the shapes at a particular position on the grid, such that by viewing it using suitable imaging means, the orientation of the marker with respect to the viewing plane may be determined in a facile manner.

In a further use of the lumen trajectory device of the invention, after the 3D trajectory of the lumen is generated using a lumen trajectory device, then it is feasible to register and determine the exact position of any device that has markers (radio-graphic or otherwise) that can be identified using an imaging modality. Such determination of unique position of the device is feasible either in the presence of the lumen trajectory device in the field of view by tracking relative positions with respect to fixed and known positions of the lumen tracking device. Alternately, in the absence of the lumen trajectory tracking device, the unique position of the device may be determined by utilizing the reference patch as a common reference. Co-registering is described in more detail below.

In a yet another embodiment, the lumen trajectory device may be used to obtain more accurate renditions of the 3D trajectory of the lumen volume of interest. This may be achieved by inserting the endo-lumen instrument (by either pushing or pulling it) through the lumen during which time, different sets of markers occupy the same region in the lumen. This affords multiple measurements of the 3-D trajectory for the same region. These multiple measurements can be used to further refine the lumen 3D and make it more accurate. These multiple measurements can also be used to determine the 3D trajectory of lumen segments corresponding to multiple phases of the heartbeat.

Figure 45:
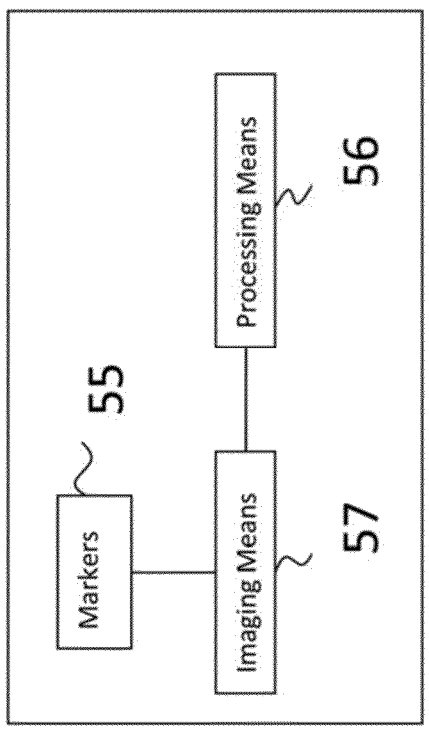
FIG. 45 shows a block diagram representation of a lumen trajectory system.

In yet another aspect, the invention provides a lumen trajectory system. Referring to the drawings, FIG. 45 shows a block diagrammatic representation of the lumen trajectory system 53. The system comprises a plurality of markers 55 positioned at predefined locations on a wire or other endoluminal device. As already noted, the device is configured to be placed in vivo in a volume of interest. The system comprises an imaging component 57 for imaging the endoluminal device in the volume of interest in a lumen as it traverses the lumen. Imaging may include, for example, but not limited to, X-Ray, infrared, ultrasound, and the like, and combinations thereof. The imaging component 57 is configured to obtain an image of the wire at different time intervals as the tracking module traverses through the volume of interest, to provide the observed identity the observed spacing. The imaging component 57 is further configured to behave as a synchronous phase imaging device to obtain phase synchronized images, so as to map the observed identity at different phases of heart.

The lumen trajectory system 53 also comprises a processing component 56. The processing component is used for processing the image obtained from the imaging component to determine at least an observed identity for each of the plurality of markers and an observed spacing between at least two markers from the plurality of markers. The lumen trajectory system 53 uses the method described herein to determine at least an observed identity for each of the plurality of markers and an observed spacing between at least two markers from the plurality of markers. The lumen trajectory system 53 is further used for determining a position of each marker in a 3D space that defines the volume of interest based on the observed identity, the observed spacing and an original identity of each of the plurality of markers, to determine the lumen trajectory in a 3D volume based on the position of each marker, using the method steps of the invention described herein.

The lumen trajectory system also comprises a reference patch to calibrate the observed data from the imaging means and the processing means. The reference patch may be configured as already described herein.

The lumen trajectory system 53 may also comprise an output module to provide the results and image as a suitable output Typical output includes a 3D static image, an animated rendition of the lumen trajectory, and the like. The lumen trajectory system further comprises a communication module to communicate the results and image to suitable recipients, such as experts, physicians, specialists, and the like. Wireless and wired communication may be possible depending on the computing capability, bandwidth, file size, and the like. Other components and features relevant to the lumen trajectory system of the invention 53 will become obvious to one skilled in the art, and is contemplated to be within the scope of the invention.

Figure 46:
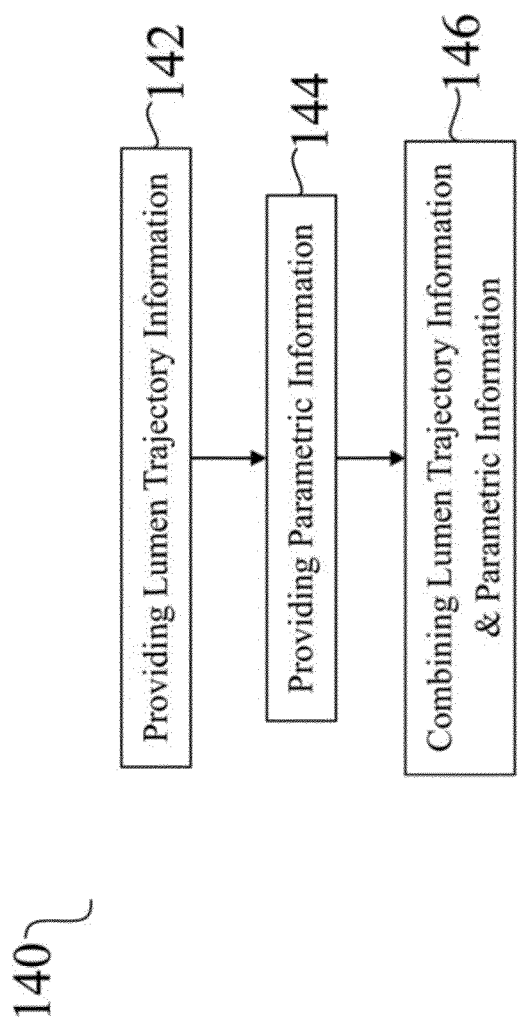
FIG. 46 is a flowchart representation comprising exemplary steps involved in a method of the disclosure.

Some embodiments provide for obtaining reference information for diagnostic guidance for an in vivo medical procedure. FIG. 46 shows exemplary steps involved in exemplary method 140. The method comprises providing lumen trajectory information corresponding to a lumen in step 142. Lumen trajectory information can be obtained as described in any of the methods herein above. Lumen trajectory information may also be obtained from a variety of techniques known in the art, and may include, for example, but not limited to, MRI, X ray, ECG, fluoroscopy, microscopy, ultrasound imaging and combinations thereof. Depending on the technique used to obtain the lumen trajectory information and the computing power available on hand, the lumen trajectory information may be a 2D image, a 3D image, in a tabular form, or any other suitable form of representation. In one specific embodiment, when the lumen trajectory information is provided in a tabular form, the table may comprise columns such as Serial Number, Distance from a Reference Point (such as the insertion point of a catheter), and the like. Data points made available in a tabular form may have the appropriate levels of experimental accuracy as required, such as ±0.01 mm.

The method then comprises providing parametric information corresponding to the lumen in step 144. Parametric information includes any information that gives an idea on the nature of the lumen, such as, for example without limitation, pressure, blood flow rate, cross sectional area, and combinations thereof. This type of information may be necessary to assess blocks, aneurysms, stenosis, and the like, and combinations thereof. Such information is obtained from any of several techniques, and may include for example, at least one of a microscopy, ultrasound, Intra Vascular Ultrasound (IVUS), Near Infrared spectroscopy (NIR), Optical Coherence Tomography (OCT), vascular optical camera type devices, other lumen measuring devices described above, and other endo-lumen diagnostic devices, and any combinations thereof. The exemplary techniques may further require the use of endo-lumen instruments as described herein.

The lumen trajectory information and the parametric information may be simultaneously obtained or they may be independently obtained. Depending on how and when the lumen trajectory and parametric information were obtained, combining the two kinds of information is done using several techniques. One such technique is to time stamp the image and use the same clock to time stamp the parametric measurements from the endo luminal instrument. Since the position information of the endoluminal device obtained through image processing technique described in this application has the same time stamp as that of the diagnostic parametric value (e.g., cross sectional area, pressure etc) the two can be stitched to form the reference information. Another method of stitching the parametric measurements with the position information is to use ECG gating. ECG is done as a routine step for all interventions. The 3D position information of the endolumen instrument is obtained from the imaging modality (e.g., X-ray) and the parametric information from the diagnostic endo luminal can be ECG gated and therefore stitched together in time domain to provide reference information.

The method further comprises combining the lumen trajectory information with the parametric information to obtain the reference information for diagnostic guidance in step 146. The combination of lumen trajectory information and the parametric information may be made available in an image form, a tabular representation, or any other visual representation, and combinations thereof. Thus, in one exemplary embodiment, the reference information is made available as an image of lumen trajectory information on which text of parametric information is overlaid. In a specific embodiment, the reference information is a fully colored image, wherein the choice of colors is an indication of certain parametric information. In another embodiment, the parametric information may be displayed as different shades of the same color indicating the degree of variation of the parameter along the lumen trajectory. In yet another embodiment, the reference information is an animation. The reference information made available as an image and/or animation may be of a suitable resolution to allow for facile diagnosis and/or treatment, or whatever the medical procedure is expected to achieve. Resolution may be measured in terms of minimum distance that needs to be distinguishable within the lumen.

In another exemplary embodiment, the reference information is made available in tabular form, wherein the columns include headers such as, but not limited to, Position ID, distance from reference, cross sectional area at the particular distance, and so on. It will become obvious to one skilled in the art that, for example, in the tabular representation, not all distances from reference may have associated parametric information like cross sectional area, whereas only certain positions will have the associated parametric information. The exact nature of the reference information will depend on various factors, such as but not limited to, the medical procedure requirement, available computing capabilities, operator's comfort and preference, and the like.

Once such reference information is made available in a suitable form, it can then displayed on a graphical user interface to be viewed having a certain suitable minimum resolution (as measured in, for example, pixels) and used by medical personnel. Such reference information provides for better identification of regions of interest and can be used to guide therapy devices more accurately to the target region. When the reference information is made available in a graphical user interface, inter-active capabilities such as zooming in and zooming out of the image can also be made possible, to enable a medical personnel to zoom into a region of interest within the lumen, and zoom out to view the entire lumen as a whole, or perform other suitable actions of relevance to enable effective diagnosis and/or treatment.

In some embodiments, while obtaining lumen trajectory information and parametric information, it may be useful to include a fixed reference for a field of view. Such a fixed reference for a field of view accounts for variations during the measurements and observations made at different times, or the movement by a subject, or any such differences arising due to extraneous circumstances. This allows for combining of the lumen trajectory information and the parametric information while accounting for all the variations and differences and still provides accurate reference information. In the absence of such fixed reference for the field of view, the error corrections due to variations from extraneous circumstances can only be corrected based on operator or technician or medical personnel's skill and experience. Fixed reference for the field of view may be obtained by a variety of techniques, and include, for example, attaching a radio opaque marker patch having known dimensions at a particular position on a subject; attaching a radio opaque marker patch on an object that may be outside the subject; an initial marking of at least one anatomic location in the lumen trajectory information by a user, wherein the characteristics of the anatomical location is known beforehand from other techniques; using a set of co-ordinates of an imaging system, such as a CNC co-ordinates of an X-ray machine. It would be appreciated by those skilled in the art that it is useful to allow users to allow the flexibility of identifying certain anatomical landmarks (e.g., beginning and end of lesions, valve root, bifurcations etc.) along the lumen trajectory.

In a further embodiment, the reference information comprises areas of diagnostic interest that are marked. For example, medical personnel can identify particular points of interest along the trajectory that they want to keep track of when subsequently delivering a therapy device such as, for example, a bifurcation. These areas of diagnostic interest may represent any particular condition of the lumen, such as blocks, stenosis, aneurysms, and the like, and combinations thereof. The one or more markings may be made by relevant personnel, such as a medical practitioner or a technician or a specialist, as a particular situation demands. Such markings allow for greater case of diagnosis and treatment of the subject. The markings can be made by physically identifying a region of interest on a screen using, for example, a touch screen or a mouse.

In some embodiments, the lumen trajectory information and parametric information are phase synchronized. The heart has phases that include pumping and back-filling, also referred to as systole and diastole. During each phase, the nature of the lumen changes as compared to the nature of the lumen in another phase. Thus, in some instances, it is important to know the phase of the heart while obtaining the lumen trajectory information and the parametric information. Methods of identifying the phases of the heart are known in the art, such as electrocardiogram (ECG). For example, obtaining lumen trajectory information and parametric information may be achieved along with ECG gating to ensure phase synchronization. Multiple measurements with ECG gating may be necessary to obtain a good average measurement that is viable for further use.

Having such accurate reference information on hand provides a distinct advantage for the medical personnel to conduct diagnosis, treat subjects, perform surgeries, and conduct any medical procedures with greater chances of success. Thus, medical personnel do not have to rely on skill, expertise, knowledge and experience in the field entirely to perform a medical procedure. The reference information made available by the method of the invention will augment a medical personnel's skill, knowledge, experience and expertise very well.

Figure 47:
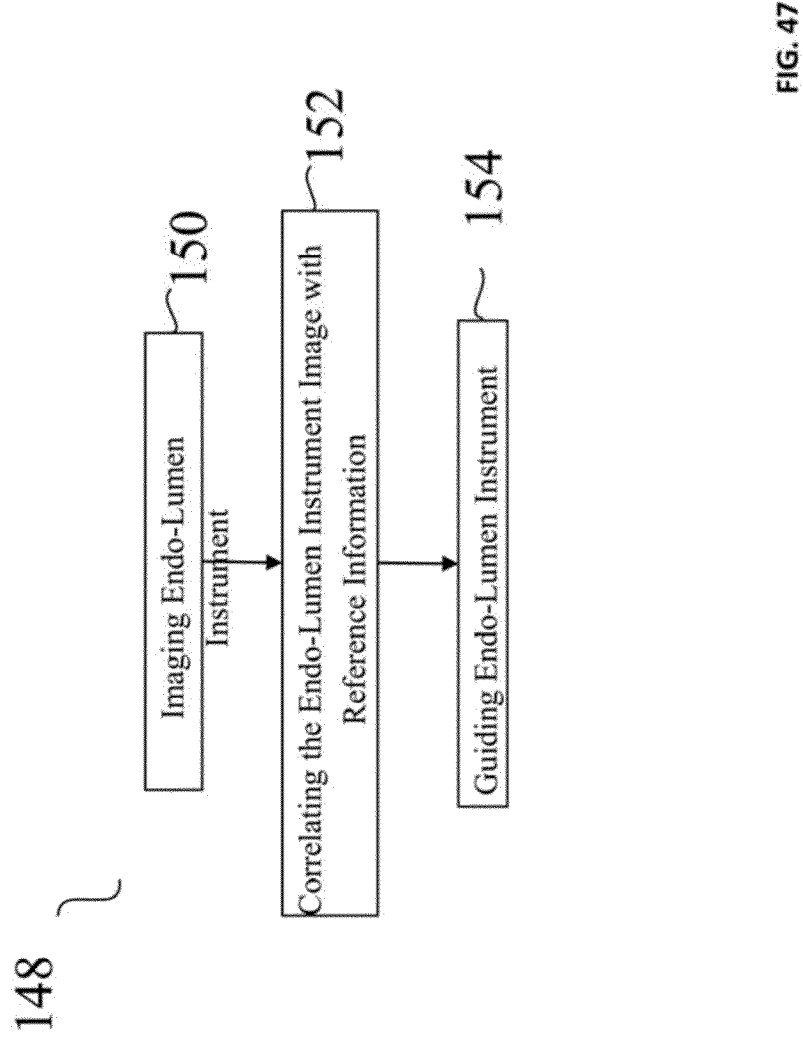
FIG. 47 is a flowchart representation comprising exemplary steps involved in a method of the disclosure.

Another aspect is a method for guiding an endo-lumen instrument in the lumen using the reference information. The exemplary steps for this method are shown in FIG. 47 in the form of flowchart 148. The reference information is obtained as described herein above. The method for guiding the endo-lumen instrument involves imaging the endo-lumen instrument after it has been inserted into the lumen to provide an endo-lumen instrument image, depicted by numeral 150. Techniques for imaging are known, and may include, X-Ray, MRI, etc. The image is made available as a 2D image or may be represented in any convenient form suitable for viewing. The convenient form may depend on a variety of factors, such as computing requirements, case of viewing and comprehensibility, medical personnel's comfort level, and the like, and combinations thereof.

Further, the endo-lumen instrument image may also ECG gated by synchronizing the imaging technique with cardiac gating. The method for guiding the endo-lumen instrument then includes correlating the endo-lumen instrument image with the reference information, shown by numeral 150. As noted herein, the reference information may be in any suitable form, and the endo-lumen instrument image will also be converted into a suitable form such that the endo-lumen instrument image and the reference information may be correlated appropriately. In one embodiment, the reference information is made available as a 2D static image, and the endo-lumen instrument image is also made available as a 2D image overlayed in realtime along the lumen trajectory as the endolumen instrument traverses the path, thus the instantaneous position of the endo-lumen instrument with respect to the reference information of the lumen. One skilled in the art will immediately recognize that a series of such correlations may be performed to obtain almost a real-time sequence of endo-lumen instrument images with respect to the reference information, thus guiding the endoluminal instrument to the desired position of interest within the lumen.

Subsequently, any endo-lumen instrument is guided to the region of interest, as shown in step 154. Guiding may be achieved in a facile manner using methods described herein. Thus, in an exemplary embodiment, the reference information is made available as a 2D reference image, and the endo-lumen instrument image is tracked with respect to the reference image. This is then displayed on a graphical user interface such as a screen having suitable resolution, such as 1024×800 pixels. Medical personnel can then view the endo-lumen instrument as it traverses through the lumen, and then arrive at a region of interest that is displayed in a clear manner on the reference image (along the lumen trajectory originally generated). As noted herein, one or more regions of interest (lesions, bifurcations, vascular anomalies etc.) in the lumen along the trajectory may also be marked and registered with respect to the "same" fixed reference (origin) as of the lumen trajectory to allow for conducting the medical procedure in a facile manner. The medical personnel may also be given the ability to zoom into a region of interest to allow for accurately guiding the endo-lumen instrument to the exact position to conduct any medical procedures. Such medical procedures may include, for example, delivering a stent, delivering a balloon catheter along with the stent, etc.

Methods herein can be advantageously administered using a suitable software program or algorithm. Thus, in yet another aspect, the disclosure provides algorithms for obtaining reference information and the method for guiding an endo-lumen instrument. The algorithm(s) generally require certain minimum computing requirements with processing capabilities that are also connected appropriately to the imaging instrument to process the images that come from the instrument. A suitable graphical user interface, such as a screen having a certain resolution, input/output interfaces such as keyboard and mouse can be used with the algorithm. The algorithm can be on a suitable medium such as a CD, a flash drive, an external hard drive, EPROM, and the like. The algorithm can be provided as a downloadable program in the form of an executable and self-extractable file from a suitable source, such as a website on the internet.

Figure 48:
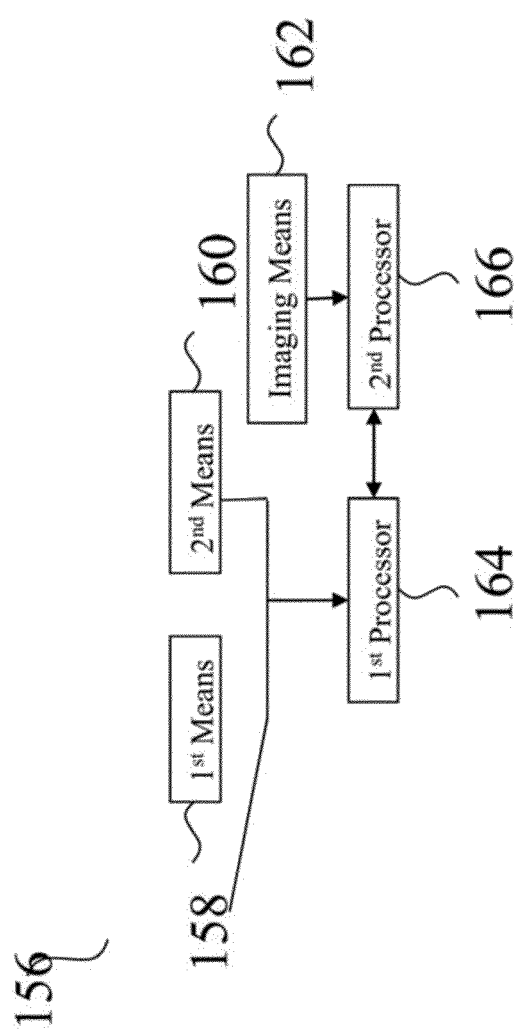
FIG. 48 is a block diagrammatic representation of an exemplary system of the disclosure.

In a further aspect, a system is adapted to guide the endo-lumen instrument to a region of interest in the lumen. FIG. 48 in a block diagrammatic representation of exemplary system 156. System 26 comprises a first means 158 for providing the lumen trajectory information, which may include any of the techniques described herein; a second means 160 for providing a parametric information, an imaging means 162 to image the endo-lumen instrument in the lumen for obtaining an endo-lumen instrument image, a first processor 164 for combining the lumen trajectory information and the parametric information to provide a reference information, and a second processor 166 for correlating the endo-lumen instrument image with the reference information to guide the endo-lumen instrument to the region of interest in the lumen. The system may also comprise a display module to display the reference information, the endo-lumen instrument image, and combined reference information and endo-lumen instrument image. The system also comprises an input/output module, where the input module receives inputs for the first means and second means and the output module provides the results for the first and second processor. The system also comprises a communication module to enable communication between the various modules. The manner of communication may be through wired connections, such as using IEEE 488 cable, RS-232 cable, Ethernet cable, telephone line, VGA adapter cable, and the like, and combinations thereof. Alternately, communications between various module may be achieved wirelessly, such as using Bluetooth, infrared connectivity, wireless LAN, and the like. Further modules that may be incorporated into the system will become obvious to one skilled in the art, and is contemplated to be within the scope of the invention. The individual modules may also be situated remote to each other and connected through appropriate means to each other. Thus, the display module may be made available in a remote location, such as in another part of the building, or in a different location in the city, and so on, where, for example, an expert is located, to obtain the expert's opinion and guidance while conducting the medical procedure.

A hypothetical example is now provided to illustrate an exemplary method that obtains vascular bodily lumen information and uses it to guide a therapy device within the lumen to a region of interest. A 65 year-old subject having hypertension, dyslipidemia, a prior catheterization, and exhibiting mild coronary artery disease, markedly abnormal nuclear stress test, and a large wall defect. Although asymptomatic, the patient is referred for cardiac catheterization, given large perfusion defect. Angiography reveals a 95% stenosis. Using traditional stenting techniques, post-stenting angiography reveals a question as to whether the stent is optimally deployed since the vessel appears to neck down proximal to the stent. Post-stenting IVUS reveals the stent is significantly undersized and underexpanded. A repeat intervention is required, and a second stent is deployed proximal to the first stent.

This repeat intervention could be avoided using the exemplary method. With standard angiography aided by IVUS, the steps of the intervention include performing the angiography; stent selection based on angiographic visual assessment (subjective due to foreshortening and visual artifacts); intervention (stent placement and deployment) followed by angiography that reveals potential for suboptimal deployment (geographic miss). To confirm this, IVUS is used to reveal the stent is undersized and/or underexpanded and/or longitudinally misplaced. The IVUS catheter is replaced by another dilation catheter and the stent is post-dilated to correct for undersizing. The dilation catheter is replaced by a stent catheter and a second stent is placed proximal to the first stent (and/or overlapping). A final angiography is performed to confirm results. Due to time, a second IVUS review of the stents may or may not be performed, leaving some uncertainty in the process as to the success of the procedure. Thus, as outlined several exchanges of devices have to be made to achieve the result. Furthermore, the exact position of the lesion is not known in real time and hence the stent delivery catheter cannot be guided to the right location leaving room for longitudinal geographic misplacement of stent.

In contrast, when a guidewire with electrodes as described above is used for the catheterization procedure, the process is simplified. First an angiography is performed; a guide wire as described above is positioned in the vessel across the lesion; the system obtains lesion length measurements and/or reference vessel diameter and/or cross sectional area as it traverses through the lesion using techniques described herein. Concomitantly, as the guidewire is traversing the lumen, the positional information of the guidewire and other anatomic points of interests such as lesions and bifurcation are co-registered with respect to a fixed reference, which is described above. The cross sectional area information is stitched with the position information to create a guidance system as described above. Based on the cross sectional area of the lesion, the minimum lumen area ("MLA") of the lesion, and the length of the lesion, the physician selects an appropriate stent for deployment. The location of the lesion can be overlayed on a static reference angiographic image that is used by the physician to guide the stent delivery catheter to the correct location. Furthermore, since the stent delivery catheter has radio-opaque markers it can be tracked with respect to the same reference as that of the active guide wire using the image processing algorithms described above. In one of the embodiments of the system interface a rendering of the stent delivery catheter movement can be displayed on the same static angiographic image that has an overlay of lesion location. Thus, this gives the physician precise visual representation of location of the stent with respect to the lesion in real time. Once the stent is deployed in the location of interest the stent delivery catheter can be withdrawn back behind the stented zone. The guide wire can then be retracted back such that the electrodes cross the stented region. As the electrodes cross the stented zone they provide a measurement of cross sectional area of the stented zone, i.e. a complete stent profile. By comparing this to the reference lumen (i.e., not blocked) cross sectional area, it can be determined if the stent is under-deployed. If so, the user can either advance the same stent delivery system to the precise location and expand again, or they can formulate their post-dilation strategy using the measured information. If the physician chooses to post dilate, then the size of the post dilation balloon catheter is precisely determined using the information on the stented cross sectional area profile and the reference lumen cross sectional area, thus, mitigating post dilation injury. The final stent profile and cross sectional area after post dilation can be also measured by retracting the guidewire. Therefore, the guidewire can be used to measure cross sectional area, guide the choice of stent, precisely place and deploy the stent, and guide the post deployment strategy and verification of therapy. All this can be achieved without exchanging various tools, as is required in IVUS guided or angiographically guided procedures. This makes the overall procedure simple, less time consuming, cost effective, and beneficial to the patient.

An additional example now illustrates how the guidance system as described above can be used with existing imaging modalities for stent placement. A physician would have a choice to place the stent using IVUS or OCT guidance, traditional angiography guidance, OR guidance through the use of the described endoluminal guidance system described above.

In an IVUS/OCT guided system the IVUS/OCT device would be introduced in the vasculature across the point of blockage shown by the angiography. Then, using a motorized pull back the IVUS/OCT catheter is pulled back at a known fixed rate while the parameters such as lumen cross sectional area are recorded. Based on the information an appropriate stent size is selected. The IVUS/OCT system is then retracted from the vasculature and then exchanged for the stent delivery catheter. While the IVUS/OCT systems provide information about the lesion they provide no positional information of the measurements. That is, the measurements do not indicate the location of the measurement and therefore offer only information to select appropriate stent size but no further guidance to where the stent should be positioned. This is a significant disadvantage. The stent delivery catheter is then advanced to the point of interest and positioned in place by visually estimating the stenotic region on the previously-obtained still angiographic image. The angiographic images are 2D and suffer from foreshortening effects and are subject to gross errors in case of tortuous vessel. This is a very well-known phenomenon and the physician has to rely only on his or her own experience and skill. This technique can render the stents being geographically misplaced longitudinally (i.e., the expanded stent does not cover the entire blockage). This can only be verified by retracting the stent delivery catheter from the subject and repeating an IVUS/OCT imaging. If found misplaced, a possible remedy is to expand another stent in place, thus adding significant procedural cost, time and patient risk, or alternatively perform other interventions such as using a post-dilation balloon to expand in the non-covered section which is known to cause complications such as stent edge dissections that have serious consequences.

In a non IVUS/OCT guided procedure the physician selects the stent size based on experience (subjective and prone to errors). The stent delivery catheter is then advanced under X-ray view and the position of the stent in relation to the lesion is visually estimated as described previously. This method again suffers from the same drawbacks as the IVUS/OCT guided technique described above and is prone to longitudinal geographical miss and its associated effects (additional cost, time, complexity, and patient risk).

When the aforementioned guidance system is used in conjunction with IVUS/OCT or other diagnostic devices as described above (referred to herein as the "measurement device") the procedure is much simplified and less prone to geographical miss. First, the measurement device is advanced through the lumen across the lesion of interest to measure important lumen parameters such as lumen cross sectional area that help determine the appropriate size of the stent to be used as the devices. Concomitantly, as the measuring device is traversing the lumen, the 3D positional trajectory information of the device is obtained using the imaging modality and techniques described above. Hence, the lesion is co-registered respect to a fixed reference and its 3D position along the lumen trajectory is registered. Additionally, the user has an option to mark anatomic points of interests such as bifurcations or other landmarks along the lumen trajectory and they are co-registered with respect to the same fixed reference. The parametric information (such as cross sectional area) collected by the measurement device is stitched with the position information thus obtained via one of the techniques previously described. One of the advantages is that all of this happens in real-time. The location of the lesion can be overlayed on the static reference angiographic image that is used by the physician to guide stent delivery catheter to the correct location. Note that the user has completed only one step so far of advancing the measurement devices across the lesion. Now the measurement instrument is retracted if it is an IVUS or OCT system, or left in place if it is a guidewire as described above. The stent delivery catheter is then advanced into the vasculature. Since the stent delivery catheter has radio-opaque markers it can be tracked with respect to the same fixed reference using similar image processing algorithms described above. In one of the embodiments of the system interface a rendering of the stent delivery catheter movement can be displayed on the same static angiographic image that has an overlay of lesion location. Thus this gives the physician precise visual representation of location of the stent with respect to the lesion in real time. Thus, this technique provides necessary guidance to position the stent accurately and minimizes room for subjectivity and error while not introducing any additional steps. Potential benefits of the guidance system are immense as it may help in avoiding repeat intervention (additional stent), reduce cost, procedural time, and subject the patient to less risk.

In the embodiments above, the measurement and the excitation apparatus are at a physical distance from the sensors or the load across which these measurements are desired. Conductors, as described above, typically connect the electrical source, measurement apparatus, and the load, forming an electrical network. It may be appreciated by those skilled in the art that electrical de-embedding would be needed to obtain the voltage-current distributions found at the distal end where the electrodes are located based solely on the actual measurements that are performed at the proximal end of the guide-wire or catheter. This may include taking into consideration material properties of the devices, or device components, such as the wires or electrodes. Measurements may be calibrated to take such variations into account to yield accurate and precise measurements. De-embedding may occur for systems with any number of terminals, e.g., 2 port, 4 port, or any other number. Electrical values (e.g., voltage, current) may be transformed between the distal end and the proximal end of the diagnostic element as described herein.

Figure 49:
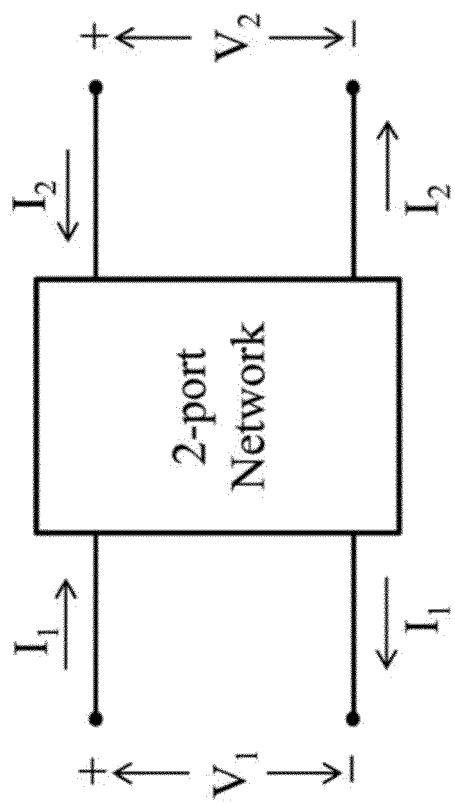
FIG. 49 is a diagrammatic representation of a 2-port network with port voltages and port currents.

There are many types of parameters known in the art for modeling an electrical network. For example, Z parameters, also called the impedance parameters of a network, relate the voltage and currents of a multi-port network. As an example of a 2 port network, with reference to FIG. 49, the 2 voltages and 2 currents are related by Z parameters as follows:

$$\begin{pmatrix} V_1 \\ V_2 \end{pmatrix} = \begin{pmatrix} Z_{11} & Z_{12} \\ Z_{21} & Z_{22} \end{pmatrix} \begin{pmatrix} I_1 \\ I_2 \end{pmatrix} \quad (5)$$

Where $$Z_{11} = \frac{V_1}{I_1}\bigg|_{I_2=0} \quad Z_{12} = \frac{V_1}{I_2}\bigg|_{I_1=0} \quad Z_{21} = \frac{V_2}{I_1}\bigg|_{I_2=0} \quad Z_{22} = \frac{V_2}{I_2}\bigg|_{I_1=0}$$

For the general case of an n-port network, it can be stated that $$Z_{nm} = \frac{V_n}{I_m}\bigg|_{I_n=0}$$

Y parameters, also referred to as Admittance parameters of a network, also relate the voltage and currents of a multi-port electrical network. As an example of a 2 port network, the 2 voltages and 2 currents are related by Y parameters as follows $$\begin{pmatrix} I_1 \\ I_2 \end{pmatrix} = \begin{pmatrix} Y_{11} & Y_{12} \\ Y_{21} & Y_{22} \end{pmatrix} \begin{pmatrix} V_1 \\ V_2 \end{pmatrix} \quad (6)$$

Where $$Y_{11} = \frac{I_1}{V_1}\bigg|_{V_2=0} \quad Y_{12} = \frac{I_1}{V_2}\bigg|_{V_1=0} \quad Y_{21} = \frac{I_2}{V_1}\bigg|_{V_2=0} \quad Y_{22} = \frac{I_2}{V_2}\bigg|_{V_1=0}$$

S parameters, also called the Scattering parameters of a network, relate the incident and reflected power waves. The relationship between the reflected power waves, incident power waves and the S-parameter matrix is given by:

$$\begin{pmatrix} b_1 \\ b_2 \end{pmatrix} = \begin{pmatrix} S_{11} & S_{12} \\ S_{21} & S_{22} \end{pmatrix} \begin{pmatrix} a_1 \\ a_2 \end{pmatrix} \quad (7)$$

where $a_n$ and $b_n$ are the incident and reflected waves, respectively, and are related to the port voltages and currents.

H parameters, also called the Hybrid parameters, relate the port voltages and currents in a different way. For a 2-port network:

$$\begin{bmatrix} V_1 \\ I_2 \end{bmatrix} = \begin{bmatrix} h_{11} & h_{12} \\ h_{21} & h_{22} \end{bmatrix} \begin{bmatrix} I_1 \\ V_2 \end{bmatrix} \text{Where}$$

$$h_{11} \stackrel{def}{=} \frac{V_1}{I_1}\bigg|_{V_2=0} \quad h_{12} \stackrel{def}{=} \frac{V_1}{V_2}\bigg|_{I_1=0}$$

$$h_{21} \stackrel{def}{=} \frac{I_2}{I_1}\bigg|_{V_2=0} \quad h_{22} \stackrel{def}{=}$$

G parameters, also called the inverse Hybrid parameters of a network, relate the voltages and current as follows:

$$\begin{bmatrix} I_1 \\ V_2 \end{bmatrix} = \begin{bmatrix} g_{11} & g_{12} \\ g_{21} & g_{22} \end{bmatrix} \begin{bmatrix} V_1 \\ I_2 \end{bmatrix} \quad (8)$$

Where $$g_{11} \stackrel{def}{=}$$

$$\frac{I_1}{V_1}\bigg|_{I_2=0} \quad g_{12} \stackrel{def}{=} \frac{I_1}{I_2}\bigg|_{V_1=0} \quad g_{21} \stackrel{def}{=} \frac{V_2}{V_1}\bigg|_{V_2=2} \quad g_{22} \stackrel{def}{=} \frac{V_2}{I_2}\bigg|_{V_1=0}$$

All the above formulations are related, and one set of parameters can be derived from another. These formulations are well known and established in the art. The Z and Y parameter matrices are inverses of each other. The H and G parameter matrices are inverses of each other. The Y and S parameters are also related, and can be derived from each other. All of the mentioned types of models are electrically equivalent. The choice of implementation depends on convenience and specific needs of a problem.

In some of these electrical networks, measurements taken for a distant load need to account for the electrical losses and coupling and compensate for any parasitic effects of electrical networks formed at the electrical source, measurement apparatus and the conductors. This problem has been dealt with extensively for a single load, situated remotely and connected across a pair of conductors that connects to an excitation and measurement apparatus disposed at a proximal location. It is a commonly used technique in high precision measurements and is popularly referred to as "Port Extension." Such a network is generally modeled as a two port network and the network parameters are solved by measuring proximal parameters for known distal loads. Nodal analysis, Mesh analysis, Superposition methods have been proposed to solve linear electrical networks. Transfer functions have also been proposed for two port networks.

However, few solutions exist when the load is not a simple single load but a distributed network with multiple ports forming a load network. Such systems have multiple conductor wires and multiple measurement entities. Therefore there exists a need to accurately measure electrical properties across a distant multi-port load network.

De-embedding is a process that may include taking into consideration material properties of the devices, or device components, such as the wires or electrodes. For example, an electrode may be at a distal end of a wire at the region of interest, and electronics to receive and process the signals may be provided at a proximal end of a wire. An electrical measurement taken by the distal electrode(s) is received by the electronics. However, a signal provided at one end of the wire may be altered by the time it reaches the other end of the wire due to material properties of the wire. This variation may be taken into account by using appropriate models based on the material characteristics, length of the wire, and other variables relevant to this situation, or performing measurements with known electrical loads at distal end and calibrating the effect of the in between electrical conductors.

For all ports the output voltages may be defined in terms of the Z-parameter matrix and the input currents by the following matrix equation:

$$V=Z*I$$

where Z is an N×N matrix the elements of which can be indexed using conventional matrix notation. In general the elements of the Z-parameter matrix are complex numbers and functions of frequency. For a one-port network, as will be clear to one skilled in the art, the Z-matrix reduces to a single element, that is the ordinary impedance measured between the two terminals.

An equivalent relationship between port voltages and currents of an N-port network can also be expressed as $$I=Y*V$$

where Y is an N×N matrix. Y is related to Z, and generally speaking, is the matrix inverse of Z. In some special circumstances, either Z or Y becomes non-invertible.

Figure 50:
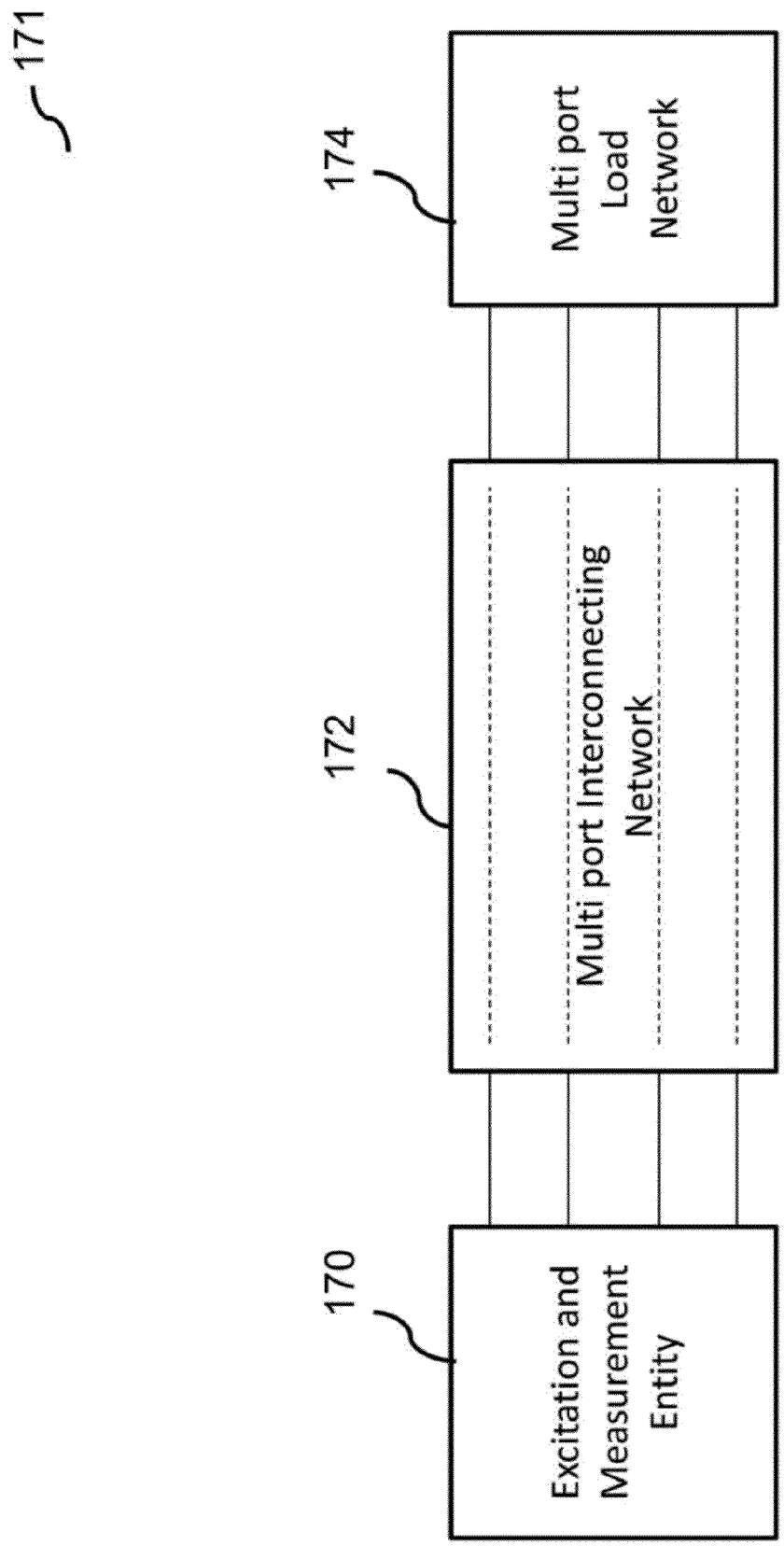
FIG. 50 is a diagrammatic representation of an exemplary embodiment with a multi port network at a distal end and the excitation and measurement entity at a proximal end.

FIG. 50 is a diagrammatic representation of an exemplary embodiment of system 171. The system is adapted to estimate electrical network 174 of a distant zone (herein referred to as a load network) when it is excited by an electrical stimulus near the proximal end. Load network 174 situated on the distal end is connected to a plurality of stimulating and measuring devices 170 on the proximal end through a plurality of conductors 172 whose combined electrical property is fixed but unknown. The stimulus can be either an arbitrary current or voltage from the excitation device located at the proximal end while the measurements are in the form of voltage measurements again at the proximal end. The voltage measurement is in general non-ideal (i.e., the voltage measurement devices draw non-zero finite currents from the network and hence loads the network). As would be appreciated by those skilled in the art, the systems and methods described herein can be extended and applied to any area of operation where the electrical network to be estimated is situated at a remote location where in-situ excitation and measurements are not feasible.

It would be understood by those skilled in the art that for an n-port load network, there would be multiple conductor wires (up to n pairs) extending down to the proximal end connecting to an excitation entity and at least to corresponding "n" measurement entities. An additional reference measurement is also performed across two arbitrary nodes in the circuit, such that it has independent information from the previous n measurements.

Figure 51:
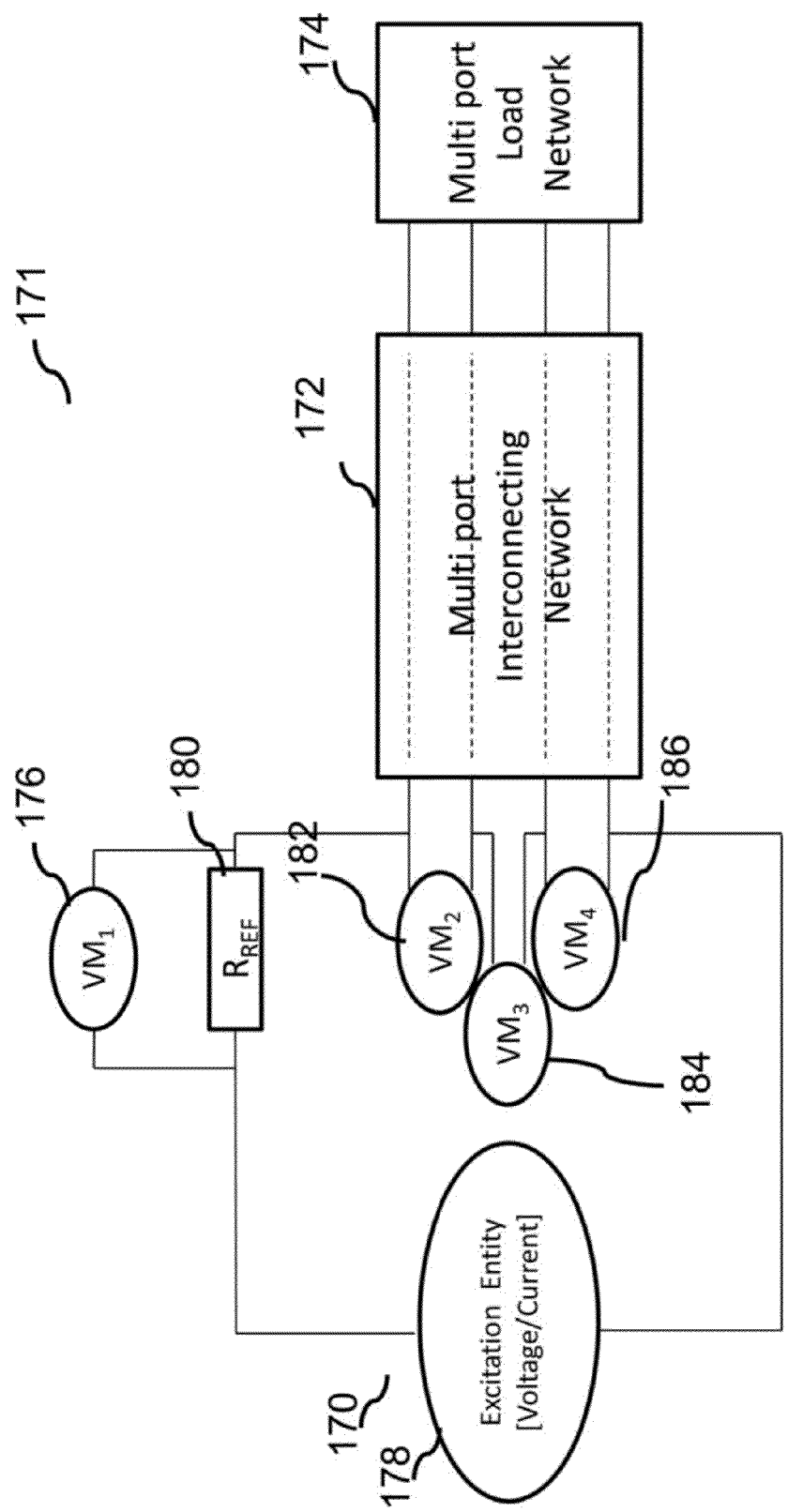
FIG. 51 is a diagrammatic representation of another exemplary embodiment with a multi port network at a distal end and the excitation and measurement entity at a proximal end.
Figure 52:
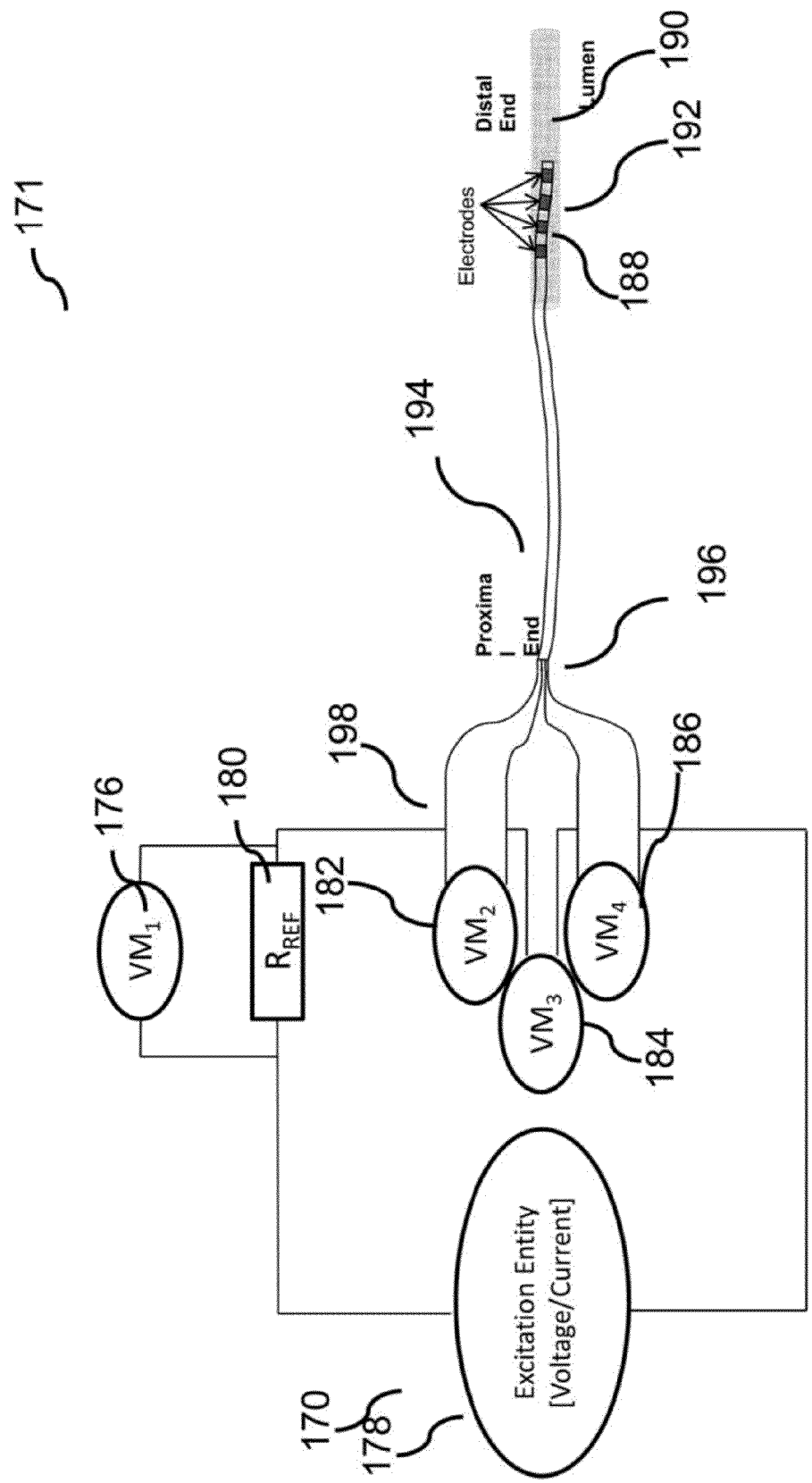
FIG. 52 is a diagrammatic representation of an exemplary embodiment for use in measuring electrical response from a body lumen.

An exemplary method of using system 171 from FIG. 51 is shown in FIG. 52. System 171 measures voltages at the proximal end corresponding to distal voltages across four conductors connected to the distal end electrodes 188 (four shown) placed in vivo in a body lumen 190. These measurements are useful for estimating the lumen dimension, which in turn is useful for several medical procedures. As shown, the four electrodes 188 are disposed longitudinally on distal region 192 of elongate medical device 194, such as a catheter or a guide wire. Elongate medical device 194 has been positioned within lumen 190 of a vascular bodily lumen, such as a blood vessel. The four electrodes are electrically coupled to four conductors 198 extending along the length of the elongate medical device 194, and terminating on a connector on the proximal end 196. Though four electrodes are shown for the exemplary embodiment, three or more electrodes can be used in different configurations needed for measurements and these are included in the scope of the systems and methods described herein. The connector is electrically connected to hardware adapted to provide the stimulus across the two conductors connected to the electrodes and also measures the three voltages across the three pair of conductors. The hardware includes an electrical source and a measurement device 170 having the excitation entity 178 and measurement entities 182, 184, 186. A fourth measurement via the measurement entity 176 is done across a reference resistor 180 which is in series with this network. The entire network in between involving the catheter and the reference resistor is invariant across various load configurations at the distal end 192 but not known to start with and needs to be estimated through carefully chosen load configurations. The calibration methods as described herein estimate this network in order to correctly determine and dc-embed the measurements for any arbitrary load network connected to it at a distal location.

Figure 53:
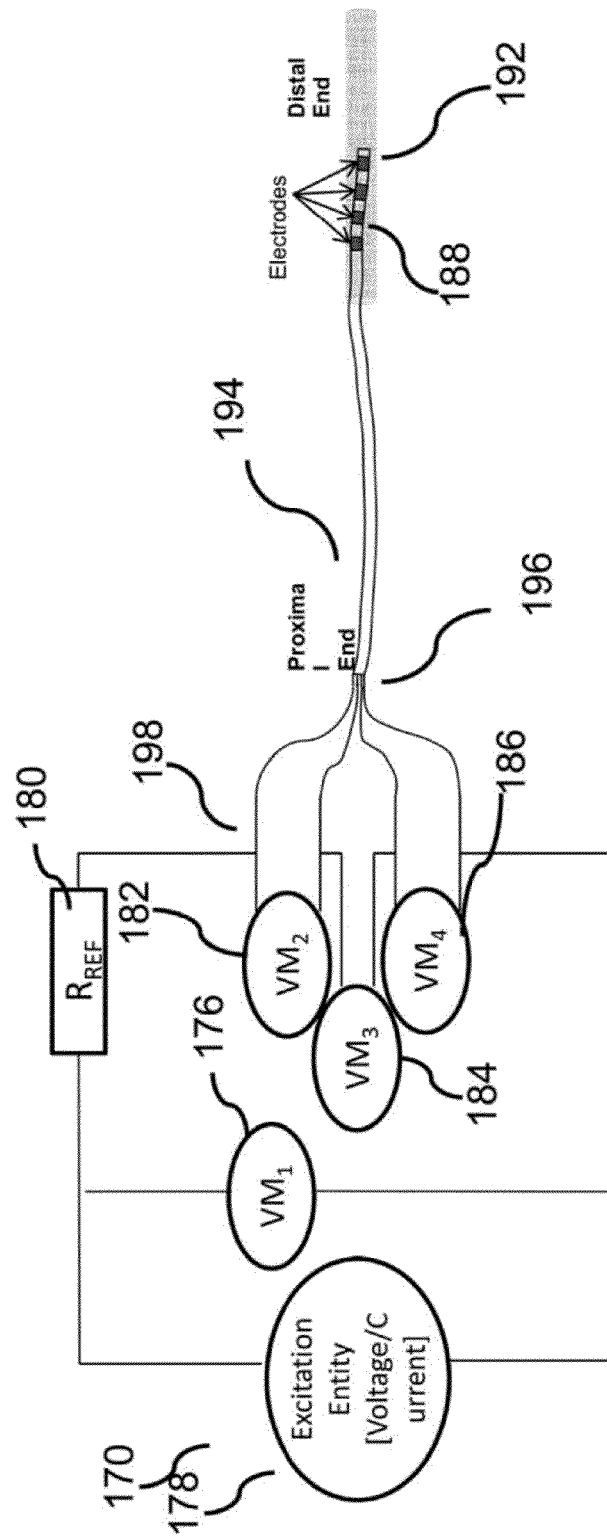
FIG. 53 is a diagrammatic representation for another exemplary embodiment with a different configuration for obtaining the measurements from a body lumen.

FIG. 53 is another exemplary embodiment of system 200 with a different configuration for obtaining the measurements. In this embodiment the fourth measurement entity 176 (VM1) is in parallel with the excitation entity 178 to obtain the reference voltage across the excitation entity, while the other three measurements are obtained as mentioned in reference to FIG. 52. The other components in FIG. 53 are substantially the same as in the embodiment of FIG. 52. It would be appreciated by those skilled in the an that there may be other alternate configurations for obtaining the measurements and the embodiments described in reference to FIG. 51. FIG. 52 and FIG. 53 are non-limiting examples. In general, any four independent measurements would suffice for estimation of a distal load network.

The measurement entities VM1, VM2, VM3 and VM4 shown as 176, 182, 184 and 186 in FIG. 51, FIG. 52 and FIG. 53 respectively are typically, but not limited to, a set of front end buffers and amplifiers for signal conditioning and noise filtering followed by an analog-to-digital converter. The measurement entity may provide frequency dependent gain to the incident signal across it. In an ideal scenario, a voltage measurement unit should not draw any current from the network it is connected to, but in practice it is impossible to implement the same. However, as would be appreciated by those skilled in the art, the voltage measurement entity can be equivalently modeled as a cascade of an equivalent parasitic network that accounts for the loading, filtering, and other non-idealities followed by an ideal buffer and gain unit that does not draw any input current and only amplify the incident voltage by a fixed amount. Further, the parasitic network can be merged as a part of the in between catheter network and estimated jointly, as is described in more detail herein below.

Figure 54:
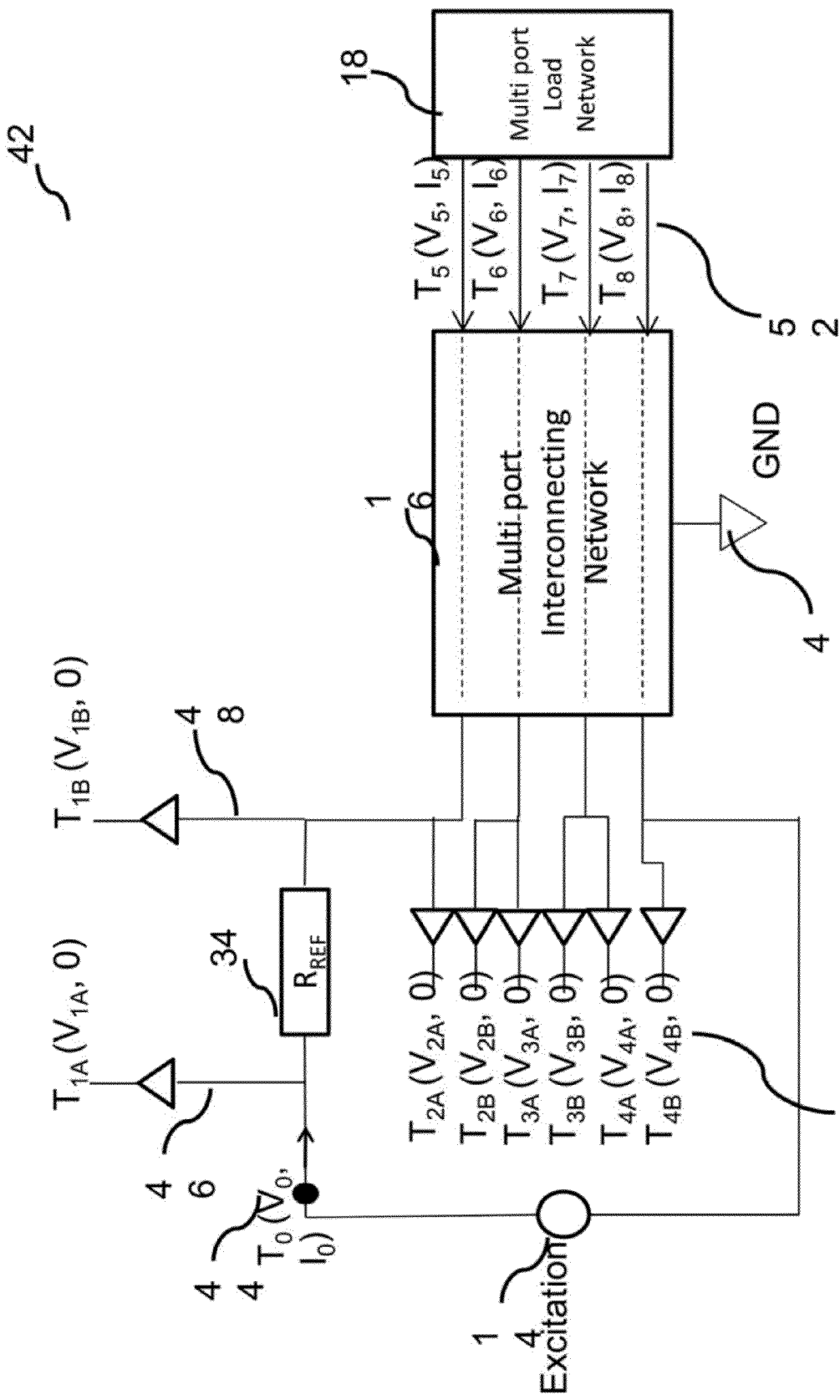
FIG. 54 is a diagrammatic representation of a multi terminal embodiment used for modeling the system of FIG. 51 and FIG. 52.

FIG. 54 is a terminal representation for the embodiment shown in FIG. 52. It will be understood by those skilled in the art that a terminal, generally referred as Tk (Vk, Ik) represents a terminal k whose voltage with respect to an arbitrary ground, represented as GND 43 is Vk while the current entering the network through that terminal is Ik. In the current embodiment, the terminals are defined in the following manner: Terminal-0 (T0), referred also as 44 is the terminal across which a voltage source or a current source 14 is connected.

The voltage measured on Terminal-0 with respect to an arbitrary GND is defined as V0, while the current entering the network through T0 is defined as I0. Terminal-1A (T1A) represented by 46 is one of the differential terminals across which the first measurement is done. This terminal does not source or sink any current to the network as these terminals are modeled as ideal measurement points. Terminal-1B represented by 48 pairs with Terminal-1A and behaves similarly to Terminal-1A. Terminal-2A, Terminal-2B are the set of differential terminals for the second measurement. Terminal-3A, Terminal-3B are the terminals for the third measurements, while Terminal-4A, Terminal-4B are the set of differential terminals for the fourth measurement. Together, the terminals 2A, 2B, 3A, 3B, 4A, 4B are shown by reference numeral 50 and represent the terminals for proximal voltages. Each of these terminals don't source or sink any current. The voltages on these terminals are all measured with reference to the same GND 43.

On the distal side, Terminal-5, Terminal-6, Terminal-7 and Terminal-8, collectively shown as 52, correspond to the four electrodes forming the multi port load network 18 that is connected to the measurement entities and excitation source via the multi port interconnecting network 16 as explained herein above. The voltages on these terminals are referred to as V5, V6, V7 and V8 and are referred to as distal voltages, wherein these measurements are performed with respect to GND 43. The currents entering the network through these terminals are referred to as 15, 16, 17 and 18, respectively.

The network can be described completely using Z parameter representations as given below:

$$V1 = Z1 * I1 \quad (9)$$

where, V1 and I1 are given by the following matrices, $$V1 = [V_0 V_{1A} V_{1B} V_{2A} V_{2B} V_{3A} V_{3B} V_{4A} V_{4B} V_5 V_6 V_7 V_8]^T$$

$$I1 = [I_0 I_5 I_6 I_7 I_8]^T \quad (10)$$

Z1 is the impedance matrix of the network relating the current vector I1 to the voltage vector V1. In another embodiment, the voltages of node 1, node 2, node 3 and node 4 representing the distal end electrodes, are represented differentially as:

$$V_1 = V_{1A} - V_{1B}$$

$$V_2 = V_{2A} - V_{2B}$$

$$V_3 = V_{3A} - V_{3B}$$

$$V_4 = V_{4A} - V_{4B} \quad (11)$$

Equation (9) can be now re-written as:

$$V2 = Z2 * I2 \quad (12)$$

where, V2 and I2 are given by the following matrices, $$V2 = [V_0 V_1 V_2 V_3 V_4 V_5 V_6 V_7 V_8]^T$$

$$I2 = [I_0 I_5 I_7 I_8]^T \quad (13)$$

Z2 is the impedance matrix of the network relating the current vector I2 to the voltage vector V2.

Figure 55:
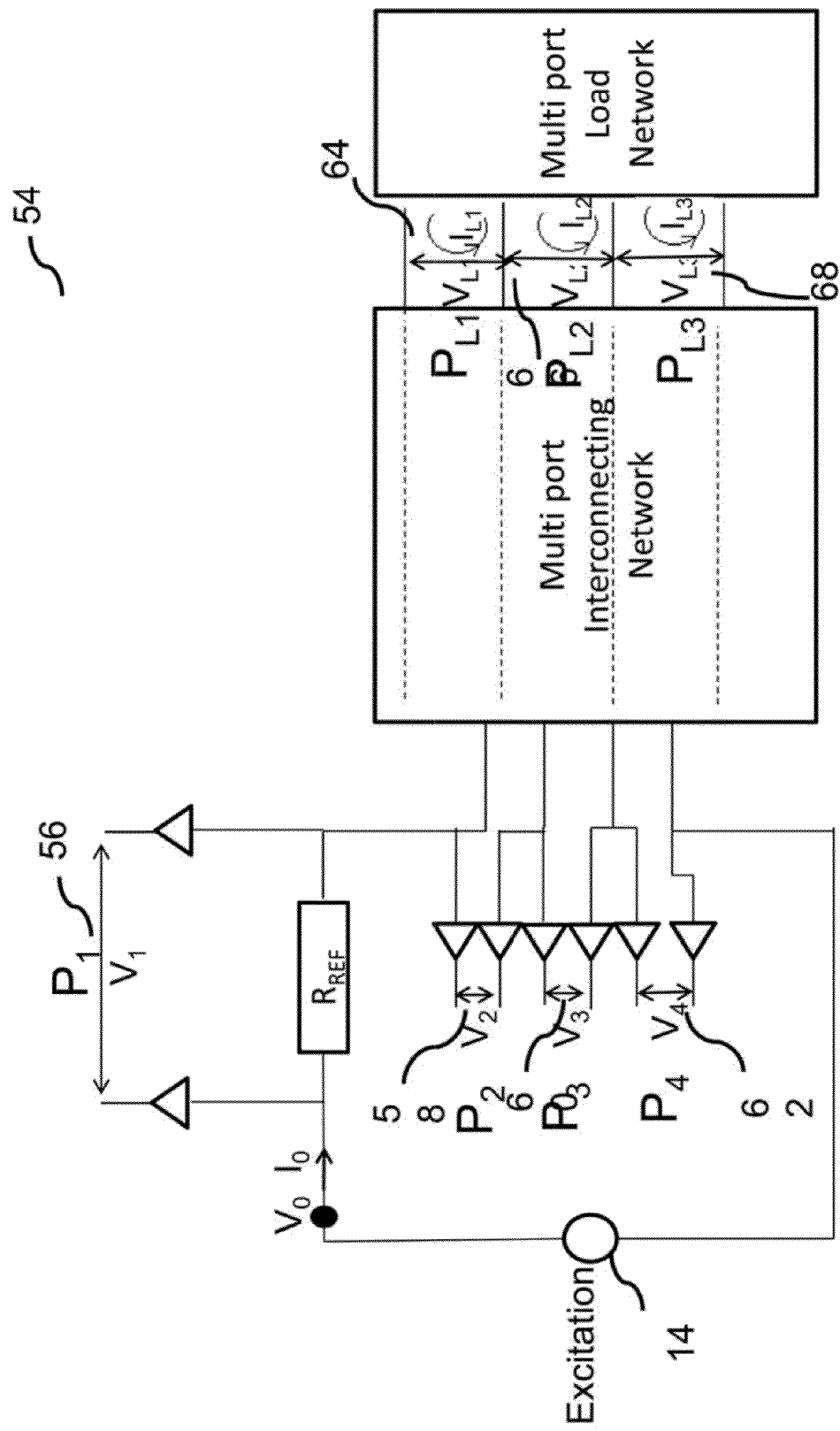
FIG. 55 is a diagrammatic representation of a multi port network that can use the assumptions of the embodiment of FIG. 53.

FIG. 55 illustrates exemplary system 54 with a floating network on the distal side. A floating network is defined as one where the sum total of all currents entering the network through all its ports is equal to zero. No separate electrical path exists between the network and GND. A port representation on the distal end is shown instead of the terminal representation as is shown in FIG. 54. Port voltages P1, P2, P3, P4 and PL1, PL2, PL3 are defined as differences between two neighboring terminal voltages, the voltage difference being depicted by reference numerals 56, 58, 60, 62, 64, 66, and 68 respectively, while the port currents are defined as the current that enters through one arm of the port and exits the network through another arm of the port.

Those skilled in the art would recognize the equivalence of the representation of FIG. 54 and FIG. 55, for a floating network on the distal side. It would require a few manipulations of rows and columns of the system of equations represented by Equation (12) to come to a new set of equations represented by Equation (14).

$$V = Z * I \quad (14)$$

where, V and I are given by, $$V = [V_0 V_1 V_2 V_3 V_4 V_{L1} V_{L2} V_{L3}]^T$$

$$I = [I_0 I_{L1} I_{L2} I_{L3}]^T \quad (15)$$

Z is the impedance matrix of the network relating the current vector I to the voltage vector V.

The floating network system as described by equation 14 is explained in more detail herein below. One skilled in the art would be able to extend the following set of derivations for use cases where the distal network is not floating. In the network depicted by FIG. 54, V0 is the voltage applied to the network. I0 is the current getting into the network. If the excitation is a perfect voltage source 14, V0 is fixed to the value of the voltage source. Similarly, for a perfect current source excitation, I0 is fixed to the value of the current for the current source. However in practice, an ideal voltage source or a current source does not exist. It may be possible to measure the voltage V0 or current I0 precisely without affecting the network appreciably. However, such measurements would involve intricate electronics especially when the frequency of excitation is high, and therefore increase the hardware complexity. Aspects of the present technique advantageously overcome this problem by deriving a method to identify the load network without requiring the knowledge of the voltage V0 or current I0 as explained herein below.

Since the value of voltage V0 is not needed, it is taken off from the first row from the system of equations defined in Equation (14). The new system of equations are written as:

$$V_1 = Z_{10} I_0 + Z_{11} I_{L1} + Z_{12} I_{L2} + Z_{13} I_{L3}$$

$$V_2 = Z_{20} I_0 + Z_{21} I_{L1} + Z_{22} I_{L2} + Z_{13} I_{23}$$

$$V_3 = Z_{30} I_0 + Z_{31} I_{L1} + Z_{32} I_{L2} + Z_{33} I_{L3}$$

$$V_4 = Z_{40} I_0 + Z_{41} I_{L1} + Z_{42} I_{L2} + Z_{43} I_{L3}$$

$$V_{L1} = Z_{50} I_0 + Z_{51} I_{L1} + Z_{52} I_{L2} + Z_{53} I_{L3}$$

$$V_{L2} = Z_{60} I_0 + Z_{61} I_{L1} + Z_{62} I_{L2} + Z_{63} I_{L3}$$

$$V_{L3} = Z_{70} I_0 + Z_{71} I_{L1} + Z_{72} I_{L2} + Z_{73} I_{L3} \quad (16)$$

In the exemplary method, the four measured voltages are grouped in a vector $V_M$ and similarly the load side voltages are grouped in the vector $V_L$. The load side currents are similarly grouped in vector $I_L$, as shown in the equations below:

$$V_M = [V_1 V_2 V_3 V_4]^T$$

$$V_L = [V_{L1} V_{L2} V_{L3}]^T$$

$$I_L = [I_{L1} I_{L2} I_{L3}]^T \quad (17)$$

Now re-writing equation (16) using the nomenclature defined above:

$$V_M = Z_{M0} I_0 + Z_{ML} I_L$$

$$V_L = Z_{L0} I_0 + Z_{LL} I_L \quad (18)$$

where, $Z_{M0}$, $Z_{ML}$, $Z_{L0}$, and $Z_{LL}$ are sub-matrices of the impedance matrix (Z) formed by the grouping of the Z-terms in Eqn (16).

As would be appreciated by those skilled in the art, the distal side (load side) is also terminated by an arbitrary network which can be modeled as a 3×3 admittance matrix Y related to the load side voltage vector $V_L$ and current vector $I_L$. For passive networks, the admittance matrix Y would have 6 independent variables, whereas for a general active network the number of variables would be 9. For some specific scenarios (including that of the one discussed) the load network may have other constraints and the degrees of freedom is lower than 6. In the specific example of FIG. 52, the anatomical constraints while measuring the lumen dimensions may drive the degrees of freedom of the Y parameters to 3 or less.

Since the current vector $I_L$ is shown entering the catheter network, a negative sign is used while representing the following load equation:

$$I_L = -YV_L \qquad (19)$$

Using, Equation (19) in Equation (18) the following is derived:

$$V_L = Z_{L0}I_0 + Z_{LL}I_L \qquad (20)$$
$$V_L = Z_{L0}I_0 - Z_{LL}YV_L$$
$$(I + Z_{LL}Y)V_L = Z_{L0}I_0$$
$$V_L = (I + Z_{LL}Y)^{-1}Z_{L0}I_0$$
$$V_M = Z_{M0}I_0 - Z_{ML}YV_L$$
$$= (Z_{M0} - Z_{ML}Y(I + Z_{LL}Y)^{-1}Z_{L0})I_0$$
$$V_M / I_0 = Z_{M0} - Z_{ML}Y(I + Z_{LL}Y)^{-1}Z_{L0}$$

Since $I_0$ is assumed to be unknown, to resolve a situation where the results would have a scale factor ambiguity, a ratio of two voltages is used instead of the absolute voltage. Without a loss of generality, the voltage across the reference resistor of FIG. 52 is used, as the reference voltage, $V_1$ and all other voltages are measured as a ratio to the reference voltage.

$$V_M / V_1 = \qquad (21)$$
$$(Z_{M0} - Z_{ML}Y[I + Z_{LL}Y]^{-1}Z_{L0}) / (Z_{10} - Z_{1L}Y[I + Z_{LL}Y]^{-1}Z_{L0});$$
where $M = 2, 3, 4 = [(Z_{M0}/Z_{L0}) - Z_{ML}Y[I + Z_{LL}Y]^{-1}(Z_{L0}/Z_{10})]/1 -$
$$Z_{1L}Y[I + Z_{LL}Y]^{-1}(Z_{L0}/Z_{10}); \text{ where } M = 2, 3,$$
$$4 = \frac{\overline{Z_{M0}} - Z_{ML}Y[1 + Z_{LL}Y]^1\overline{Z_{L0}}}{1 - Z_{1L}Y[1 + Z_{LL}Y]^1\overline{Z_{L0}}} \text{ where } M = 2, 3, 4$$

where, $\overline{Z_{M0}}$ and $\overline{Z_{L0}}$ are normalized by $Z_{10}$, and $Z_{10}$ is fixed to unity.

Thus these equations effectively model the effect of an arbitrary load network connected at a distal end to the measurements done at a proximal end.

In the formulation above, voltage ratios VM/V1 are used. This is because the exact value of V0 (in the case of voltage excitation) or I0 (in the case of current excitation) is not known precisely in normal practical situations. However, if these can be determined with enough precision, the calibration method can be formulated with absolute voltages rather than voltage ratios. As such, the disclosure envisages such alternate formulations where the voltages can be used in forms other than ratios such as absolute value, voltage differences, linear or non-linear combinations of the voltages.

The exemplary method as described herein uses the above system model for determining the actual voltage difference measurements for an arbitrary load network connected at the distal end through proximal measurements. The next step for the method is to identify the Z parameters of the connecting network along with measurement parasitics, herein referred to as the calibration step. Thereafter, a step of de-embedding is done wherein, the proximal measurements are mapped to (or, fitted to) the distal load network after due consideration for the Z parameters of the connecting network and measurement parasitics.

In the process of calibration described herein, the three voltage ratios with respect to the first voltage is measured for different combinations of precisely known load networks connected on the distal end. It may be noted that for a passive load network, in Equation (21), the number of unknown Z-parameters to be estimated is 23. The Z parameters are obtained using a suitable fitting utility that runs on the set of measured data. Since every configuration provides three voltages, it is necessary to have at least measurements from 8 independent configurations to obtain all the Z parameters. More configurations provide better noise immunity to the fitted values. The fitter routine starts with an arbitrary starting point and computes the estimated ratios of voltages across different known load configurations for Equation (21). The method then computes an error metric which is the Euclidian distance between the measured ratios and the estimated ratios. The fitter tries to minimize this error by adjusting the Z parameter values. It is possible for the solution to converge to alternate solutions. However, skilled persons in this art would recognize these challenges and come up with suitable techniques to circumvent them. This can be done by employing suitable optimization techniques. It may be noted that the fitted Z parameters are not the true Z parameters of the network but are a mathematical representation that fits the observation under the constraints of one pre-determined Z-parameter (any one of ZL0). Further, a few Z-parameters are normalized to Z10 and Z10 is fixed to unity, as was mentioned earlier.

Once the Z parameters have been estimated through the process of calibration, the connecting network can be used to identify any arbitrary load network at the distal end. In specific applications, such as but not limited to the embodiment of FIG. 52 where a catheter with four distal electrodes (connecting network) is inserted inside a lumen and the load presented on the distal side is due to the finite conductivity of blood inside the lumen or the finite conductivity of wall tissue, the degrees of freedom for the network is 3. The three voltage distributions across the three electrodes completely define the Z-parameters of the equivalent electrical network formed by the electrodes inside the lumen. Similar applications such as measurement of a cross section of a pipe electrically through similar means would also have similar degrees of freedom. Once a measurement of three ratios are taken for an arbitrary load network (with Admittance Y with 3 degrees of freedom), a similar fitter routine can be used to find out the load network. In one example, the fitter routine is initialized by a starting value of Y, which is the best case estimate given by the user. The ratios are accordingly estimated (according to Equation 21) and an error metric is computed as the difference between the measured ratios and the estimated ratios. The error metric is then minimized by adjusting the Y parameters of the load network. The Y parameters representing the lowest error represent the true Y parameter of the load network.

Figure 56:
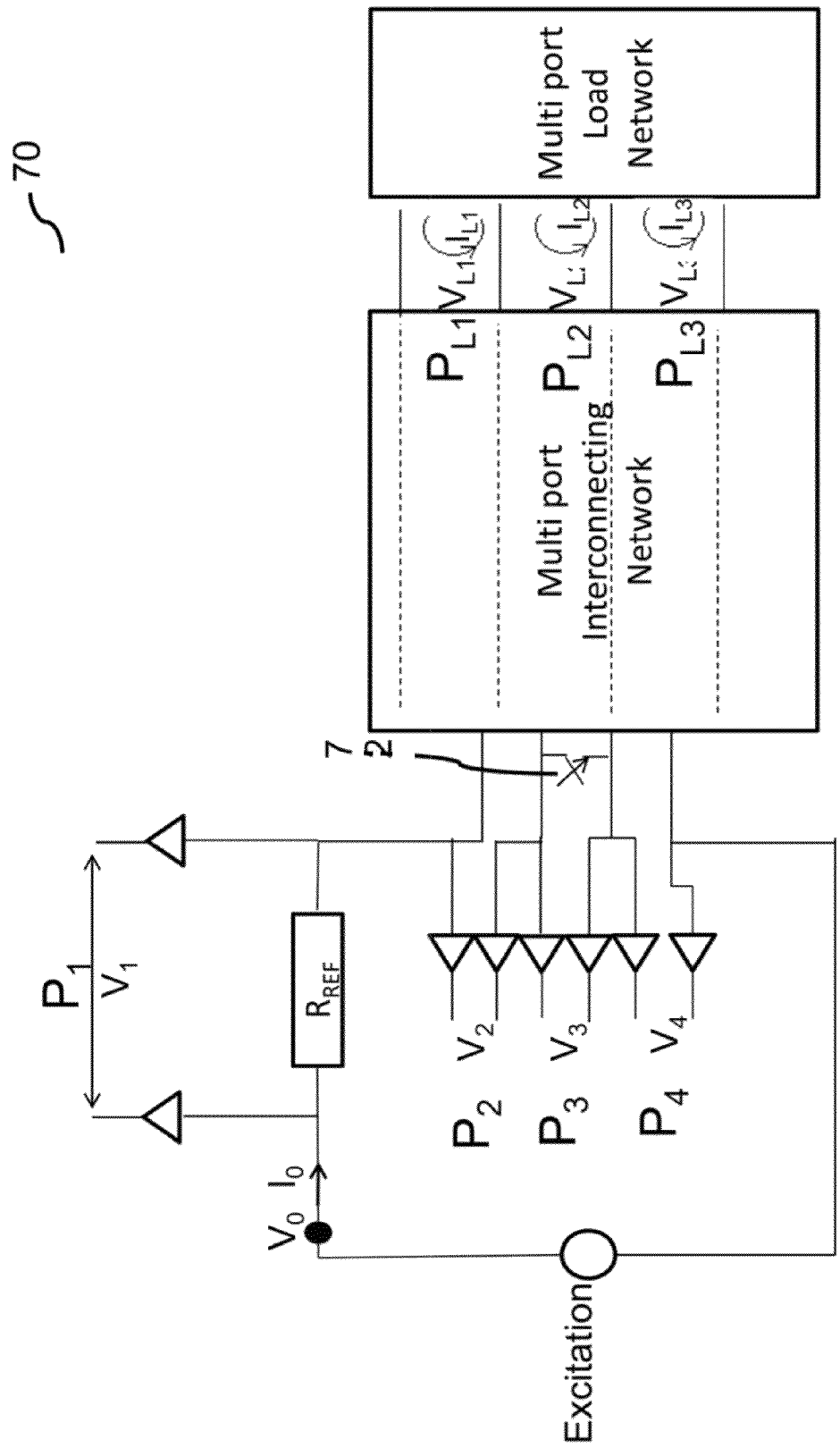
FIG. 56 is a diagrammatic representation of a multi port network that can uses the method of the invention where 6 degrees of freedom are presented.

It may be noted that since only three ratios are measured, this method is applicable to identification of networks which has no more than 3 degrees of freedom. As discussed, for an arbitrary network with three ports, the Y parameter can have 9 degrees of freedom. For passive networks, the degrees of freedom are typically 6. Identification of such networks can also be done using extension of the exemplary method. To identify a passive arbitrary load network (with 6 degrees of freedom), the calibration and de-embedding processes needs to be done for two independent interconnecting networks. In practice, it can also be achieved by taking two measurements, one with the actual interconnecting network and the other with a modified version of the same. During the calibration phase, precisely known loads are attached to the distal side of the connecting network and the three ratios are measured and while maintaining the same load, the connecting network is modified using a reversible mechanism (such as a relay 72 shorting the two center ports 2 and 3 at the proximal end of the embodiment 70 of FIG. 56) and the new ratios are measured.

The same procedure is then repeated for various load configurations. Using similar principles of the calibration phase, the Z parameters are estimated both for the parent connecting network as well as its modified version. Finally, an arbitrary passive load network is connected distal to the same connecting network. The three ratios are measured once with the original connecting network and a second time when the connecting network has been modified as before. A total of six ratios are obtained and with the knowledge of the Z parameters of the connecting network and its modified version from the calibration phase, it would be possible to unravel all the 6 degrees of freedom of the load network. The method can be also be extended to unravel an arbitrary active three port network with 9 degrees of freedom, by performing measurements using three different connecting networks.

Figure 57:
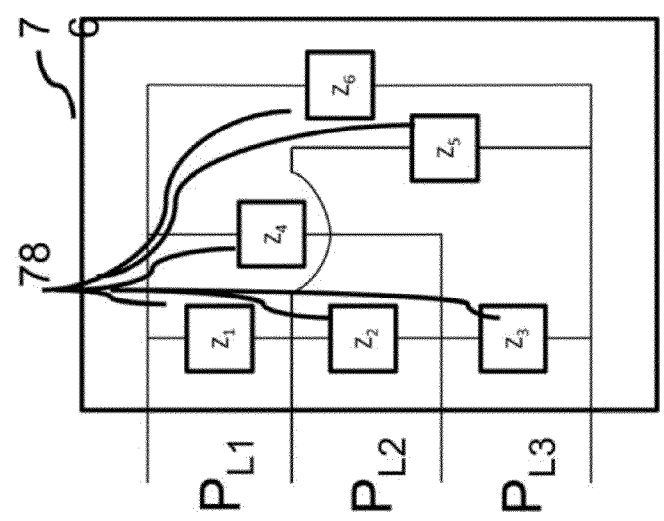
FIG. 57 is a diagrammatic representation of an embodiment with an exemplary 3-port passive network 6 complex impedances.
Figure 58:
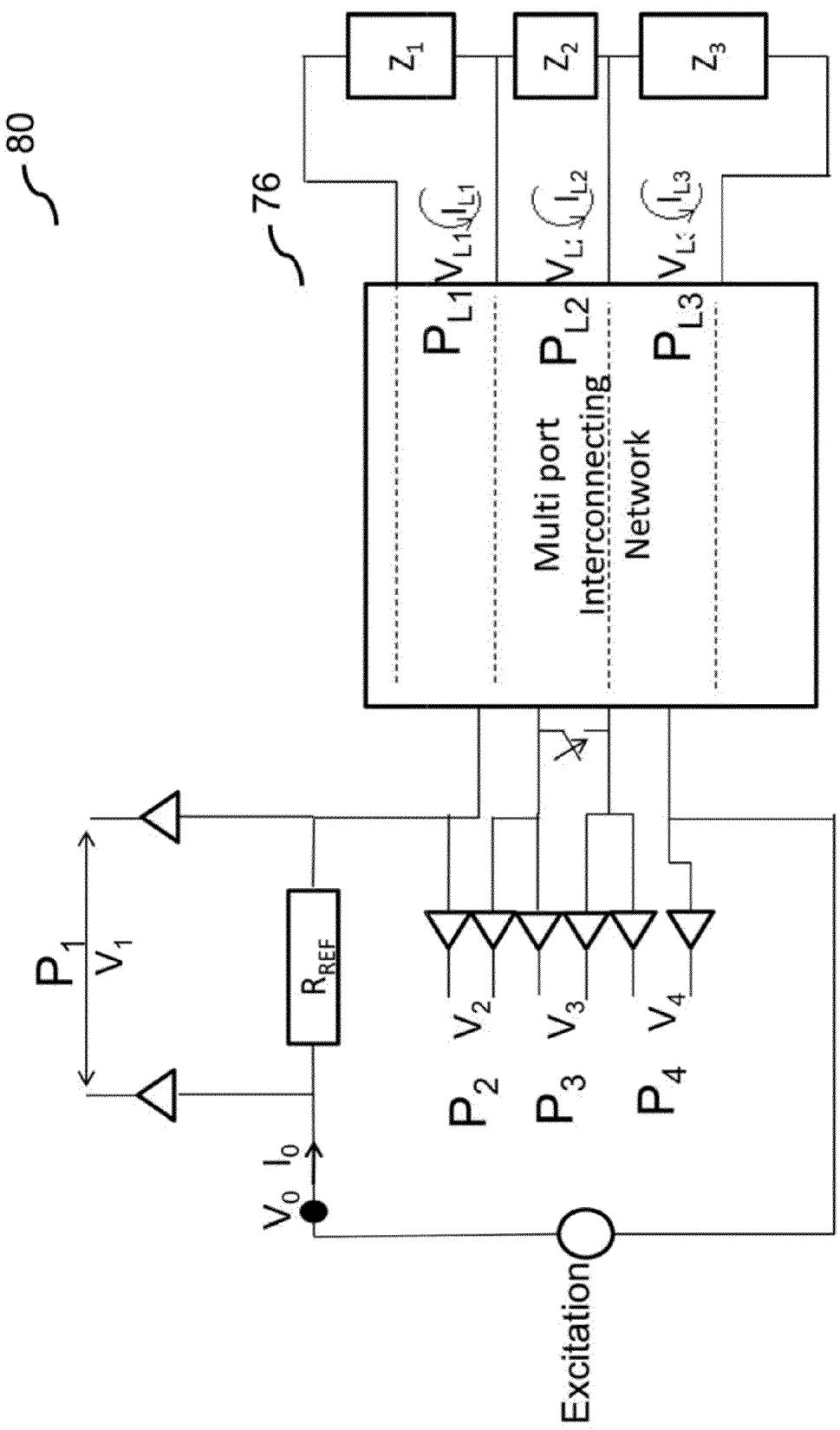
FIG. 58 is a diagrammatic representation of another embodiment with an exemplary 3-port network.

In an alternate embodiment, an n-port load network is represented by L independent (L=n2) complex impedances. As would be appreciated by skilled persons in this art, the complex impedances bear equivalence with the Z-parameters of the same network. For a passive load network, the number of independent complex impedances would be P (=n*(n−1)), since the network would be symmetric. FIG. 57 represents an embodiment 74 with an exemplary 3-port passive network 76 with 6 complex impedances shown generally by reference numeral 78. Any other passive 3-port network topology can be reduced to an equivalent network 76 with the topology shown in the embodiment 80 of FIG. 58 as well. Other components related to the excitation and measurement entity remain substantially the same as described in earlier figures.

According to network theory, as would be well understood by those skilled in the art, for any network consisting of an ordered set of discrete impedances, the voltage across any two points ($\xi 0$, v) in the network can be represented as a product of the excitation voltage or, excitation current ($\xi 0$) and a ratio of sum of polynomials formed by all the impedances present in the network. The denominator polynomial is referred to as the characteristic polynomial of the network consisting of all the impedances in the network. The characteristic polynomial is independent of the points of measurements. Further, if some part of the network consists of distributed elements and other parts consist of discrete impedances, the voltage can still be represented as a product of $\xi 0$ and the ratio of sum of polynomials formed by all the discrete impedances present in the network, wherein the coefficients of the polynomial would capture the effects of the distributed elements.

If some of the discrete impedances are of interest, the polynomials can be regrouped into a polynomial of just the discrete impedances of interest. In this case, the coefficients of the re-grouped polynomial would contain the effects of the other discrete impedances as well as the distributed elements of the network.

Referring to FIG. 50, where the measurement network 170 and the connecting network 172 are fixed while the multi-port load network 174 is allowed to change through variations of L number of load impedances $(Z_1, Z_2, \ldots Z_L)$, the voltage between any two points (u, v) in the network can be written as:

$$V(u,v) = \xi_0 \frac{b_0(u,v) + \Sigma_i b_{1i}(u,v)Z_i + \Sigma_i \Sigma_{j,i \neq j} b_{2ij}(u,v)Z_i Z_j + \ldots + b_L(u,v)Z_i Z_j, \ldots, Z_L}{1 + \Sigma_i \alpha_{1i} Z_i + \Sigma_i \Sigma_{j,i \neq j} a_{2ij} Z_i Z_j + \ldots + a_L Z_i Z_j, \ldots, Z_L} \quad (22)$$

In general, each of the L number of load impedances contributes to the voltage distribution within the network. The contribution of fixed elements within the network is absorbed in the polynomial coefficients. The denominator is equivalent to the characteristic polynomial for the combined network (170, 172 and 174), and its coefficients (a's) are fixed for the given network and depends on network 172 and 174.

In specific instances, where only the port's self-impedances are of significance, the entire n-port load network can be represented by n complex impedances. In this scenario, the Z-parameter for the network would be a diagonal matrix with n diagonal terms. FIG. 57 describes an exemplary embodiment where the number of ports (n) is 3. For such a network, with three impedances ($Z_1$, $Z_2$ and $Z_3$) on the distal side, the voltage measurements in the proximal side (e.g. $V_1, V_2, V_3, V_4$) is given by:

$$V_i = \varepsilon_0 \frac{b_0(i) + b_{11}(i)Z_1 + b_{12}(i)Z_2 + b_{13}(i)Z_3 + b_{212}(i)Z_1 Z_2 + b_{223}(i)Z_2 Z_3 + b_{231}(i)Z_3 Z_1 + b_3(i)Z_1 Z_2 Z_3}{1 + a_{11}Z_1 + a_{12}Z_2 + a_{13}Z_3 + a_{212}Z_1 Z_2 + a_{223}Z_2 Z_3 + a_{231}Z_3 Z_1 + a_3 Z_1 Z_2 Z_3} \quad (23)$$

$$i = 1, 2, 3, 4$$

Instead of the absolute measurements in the proximal end, one can also work on voltage ratios to avoid dependencies on the excitation voltage or, excitation current ($\epsilon_0$). Without loss of generality, the voltage across the reference resistor ($V_1$) is taken as reference and three ratios are constructed with respect to $V_1$.

$$\frac{V_i}{V_1} = \frac{b_0(i) + b_{11}(i)Z_1 + b_{12}(i)Z_2 + b_{13}(i)Z_3 + b_{212}(i)Z_1 Z_2 + b_{223}(i)Z_2 Z_3 + b_{231}(i)Z_3 Z_1 + b_3(i)Z_1 Z_2 Z_3}{b_0(1) + b_{11}(1)Z_1 + b_{12}(1)Z_2 + b_{13}(1)Z_3 + b_{212}(1)Z_1 Z_2 + b_{223}(1)Z_2 Z_3 + b_{231}(1)Z_3 Z_1 + b_3(1)Z_1 Z_2 Z_3} \quad (24)$$

$$i = 2, 3, 4$$

The properties of the measurement and the connecting networks are represented by the polynomial coefficients. For a network with n impedances and (n+1) measurement entities, the number of independent polynomial coefficients would be (n+1)*2n−1. It may be noted that all the polynomial coefficients in Equation (24) can be scaled by the first term in the denominator, thereby reducing one unknown. The act of calibrating these networks would involve making proximal measurements with known impedances connected to the distal ports. The number of such independent measurements required would depend on the number of unknowns that need to be solved and the number of information per measurement. A fitter routine would then run on all of these measurement ratios, for known set of loads and estimate the polynomial coefficients.

Once the process of calibration is completed, and the polynomial coefficients are obtained, any arbitrary load connected across the distal ports in a similar configuration can be estimated. With an arbitrary load connected across the distal ports in a similar configuration, the proximal measurements are made and the ratios are computed with respect to the reference measurement. Next a fitter routine is invoked with the pre-determined polynomial coefficients and the ratios corresponding to the arbitrary load. The fitter routine may be initialized by the user with a starting value of the load impedances based on best guess. The fitter shall converge to a minimal residue on finding the true value for impedances which would match the ratio of measurements. Convergence to alternate solutions are possible, however skilled persons in this art would be adept in avoiding such situations.

To estimate a generalized three port passive load network which can be modeled by six independent impedances, one would need to write the polynomial equations in Equation (22) with all six impedance present. Since the numbers of ratios measured are only three, the method needs to be extended for measurement of six impedances as discussed before. The method of calibration would involve making measurements with various combinations of load networks (comprised of all six impedances) for two independent interconnecting networks. The polynomial coefficients for both these networks would then be estimated using the individual sets of measurement ratios and the knowledge of load impedances. Next, measurements would be made with arbitrary six impedance load networks, again with the same two independent interconnecting networks. A total of six ratios along with the polynomial coefficients for both the networks would jointly be fitted by a fitter routine for estimating the six impedances. The method can similarly be extended to active networks where a nine impedance model needs to be estimated.

The above method, exemplified by a three port network with four proximal measurement entities can be easily extended to a general n-port network with n+1 proximal measurement entities on basis of Equation (22). The computation complexity grows exponentially with increasing number of load impedances in the network.

Thus the methods described herein can be extended to de-embed and evaluate a generalized n-port load network where there are n+1 measurements performed concurrently.

Any electrical measurement is corrupted due to noise and other inaccuracies of the measurement system. Due to inaccuracies of measurements, the process of calibration and de-embedding would result in inaccurate estimates of system parameters such as lumen dimension. For a given choice of measurement nodes, the measurement inaccuracies may show a flared up or, subdued effect on the estimated values depending on the transformation caused by the intervening network. Hence the choice of measurement nodes needs to be made such that the accuracy of estimated parameters is maximized for the given intervening network. This can be done analytically, through simulations or, through physical experimentations.

Figure 59:
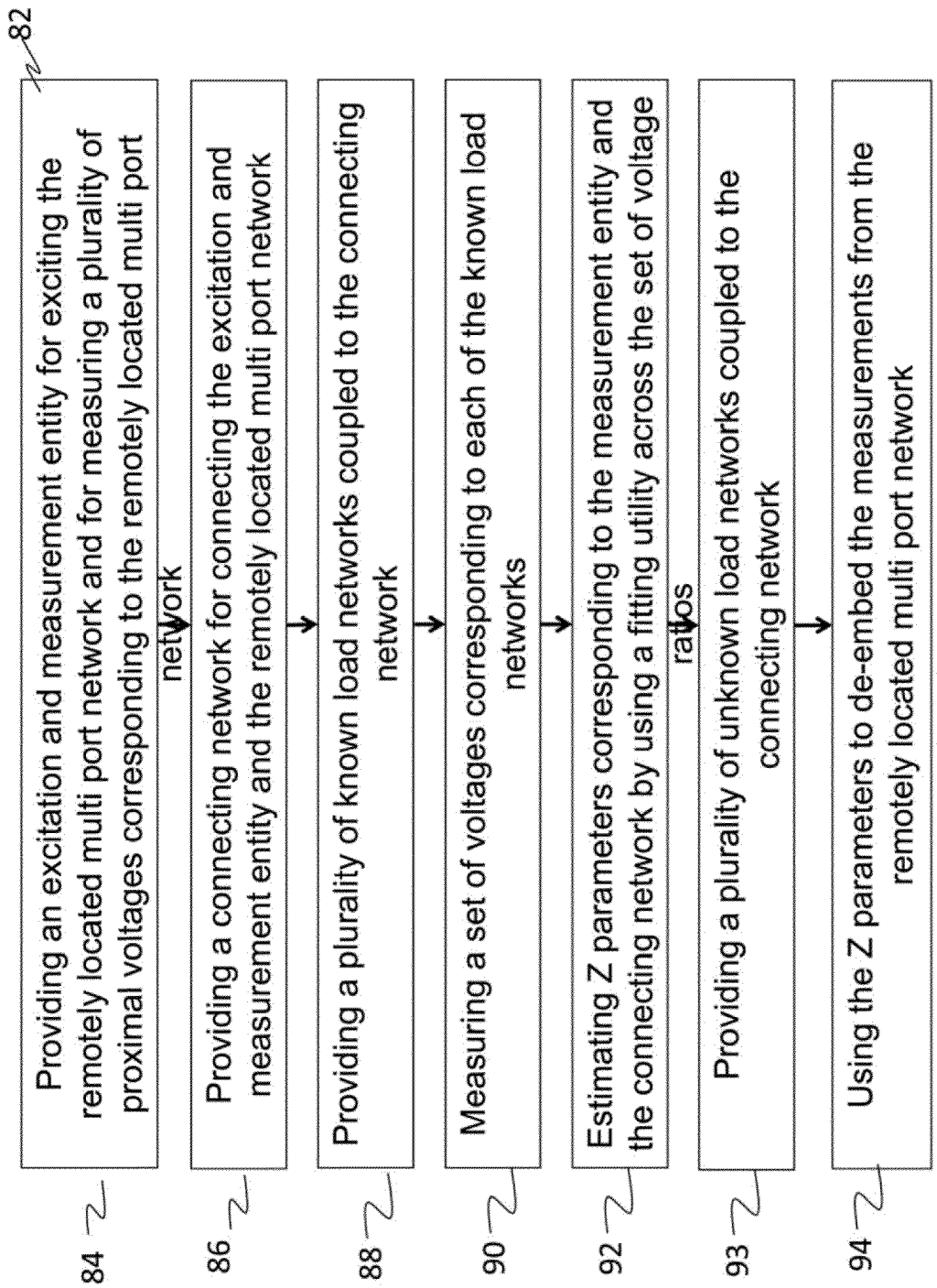
FIG. 59 is a flowchart for the exemplary method steps of the invention.

The methods as described herein above are also depicted in the form of flowchart 82 of FIG. 59. The calibration technique for use in measurements from a remotely located multi port network, is shown by steps 84 to 92 of the flowchart, and includes a step 84 of providing an excitation and measurement entity for exciting the remotely located multi port network and for measuring a plurality of proximal voltages corresponding to the remotely located multi port network; a step 86 of providing a connecting network for connecting the excitation and measurement entity and the remotely located multi port network; a step 88 providing a plurality of known load networks coupled to the connecting network. The calibration technique further includes a step 90 for measuring a set of voltage ratios corresponding to each load of the known load networks; and a step 92 for estimating electrical parameters corresponding to the measurement entity and the connecting network by using a fitting utility across the set of voltage ratios, where the electrical parameters are used for calibration. The method further includes a step 94 for using the electrical parameters to de-embed the measurements from the remotely located multi port network.

The embodiments described herein have been illustrated through use of Z parameters as electrical parameters for modeling the electrical network. As would be appreciated by those skilled in the art, using the same principles, a similar formulation can also be made using Y parameters, S parameters. H parameters and G parameters since all models are equivalent ways of representing the electrical network. As such, it is to be understood that the embodiments described herein covers all such formulations.

The technique described herein can be effectively used for determining actual voltages or voltage differences between the measuring electrodes or terminals of a remotely located multi-port network.

The method as described herein above maybe incorporated as a tool that is used to determine the voltages or any other electrical response from a remotely located multi-port network.

In a specific example, a system for de-embedding measured proximal voltages across conductors connected to at least three electrodes placed in vivo in a body lumen is also disclosed. The system may include the embodiments of FIGS. 50-53 having an excitation and measurement entity for exciting the at least three electrodes and for measuring a plurality of proximal voltages corresponding to the at least three electrodes. The system also includes a connecting network in the form of two or more conductors for connecting the excitation and measurement entity and the at least three electrodes, where the at least three electrodes are at a distal end of the two or more conductors. A processor is added in the embodiments of FIGS. 50-53 coupled to the excitation and measurement entities and the connecting network for estimating a plurality of electrical parameters as calibration parameters corresponding to the excitation and measurement entity and the connecting network, and for estimating actual voltages across the at least two pair of the at least three electrodes using the electrical parameters to de-embed the measured proximal voltages.

It would be appreciated by those skilled in the art that the embodiments described herein for example the embodiments of FIGS. 50-53, pertain to compensating for the effects to both, the excitation and measurement entity 14 and the multi-port interconnection network 16. However, in some practical situations, it may be necessary to calibrate the effects of each of the entities separately, and during the process of dc-embedding, the effects of both the entities will be combined. Further, the multi-port interconnection network 16 may include multiple parts or components. In this case, and each part would be calibrated separately and the parameters can be combined together at the time of de-embedding. It is to be understood that this divided approach for calibration and dc-embedding is also within the scope of the invention as described herein.

As used herein, the singular forms "a," "an," and "the" include the plural reference unless the context clearly indicates otherwise.

As used herein, lumen includes the volume defined by any generally elongate, sometimes tubular, structured component of a subject such as a human being, such as an artery or intestine. For example, the interior of a vessel, such as the inner space in an artery or vein through which blood flows is considered a lumen. Lumen also includes a particular portion of the generally tubular structured component of a subject, such as a section of aorta near the heart, for example. The particular section of the lumen may be of interest to a doctor, for example, as it may comprise some features associated with it, such as a blockage or a stenosis. Thus, in some instances, lumen as used herein, may also be referred herein as volume of interest, a region of interest, or a lumen of interest.

An electrical network as referred herein is an interconnection of electrical elements such as resistors, inductors, capacitors, generalized frequency dependent impedances, conductor wires, voltage sources, current sources and switches.

A terminal is the point at which a conductor from an electrical component, device or network comes to an end and provides a point of connection to external circuits. A terminal may simply be the end of a wire or it may be fitted with a connector or fastener. In network analysis, terminal means a point at which connections can be made to a network in theory and does not necessarily refer to any real physical object.

An electrical connector is an electro-mechanical device for joining electrical circuits as an interface using a mechanical assembly. The connection may be temporary, as for portable equipment, or may require a tool for assembly and removal, or may be a permanent electrical joint between two wires or devices.

As used herein electrical measurements include measurable independent, semi-independent, and dependent electrical quantities including for example voltage by the means of voltmeter (or using oscilloscope, including pulse forms), electric current by the means of ammeter, electrical resistance, conductance, susceptance and electrical conductance by the means of ohmmeter, magnetic flux and magnetic field by means of a Halls sensor, electrical charge by the means of electrometer, electrical power by the means of electricity meter, electrical power spectrum by the means of spectrum analyzer.

Electrical impedance as referred herein is defined as vector sum of electrical resistance and electrical reactance. Inductance is defined as frequency proportionality coefficient for reactance, and capacitance defined as reciprocal frequency proportional coefficient for reactance.

Electrical impedance as referred to herein is defined as a vector sum of electrical resistance and electrical reactance. Inductance is defined as frequency proportionality coefficient for reactance, and capacitance defined as reciprocal frequency proportional coefficient for reactance.

Voltage between any two points as generally referred herein is the electrical potential difference between the two points and is also referred herein as voltage difference or voltage drop.

The process of estimating the effects of electrical properties of an intervening multiport network is referred to as calibration. The process of using the estimated properties of the network to compensate for the network and obtain the compensated measurement is referred to de-embedding.

Z-parameters (the elements of an impedance matrix or Z-matrix) referred to herein are the impedance parameters for an electrical network. The Z-parameters are also known as the open circuit parameters. For determining the kth column of the Z matrix, all but the kth port are opened, current is injected on the kth port, and the voltages are analyzed on all ports. The procedure is performed for all N ports (k=1 to N) to obtain the entire Z matrix. Though the exemplary embodiments have been described using Z parameters, the methods and systems described herein are equally applicable to other parameters such as Y, S, H, and G parameters.

A generic multi-port network referred to herein includes ports 1 to N, where N is an integer depicting the total number of ports. For port n, where n is ranging from 1 to N, the associated input current through that port to the network is defined as In and the voltage across that port is defined as Vn.

As used herein, the phrase "peak-to-rms-ratio" ("PAR") means the value obtained for a waveform by the division of peak amplitude of the waveform by the root mean square value for the waveform. It is a dimensionless number generally expressed as a ratio of a positive rational number to one. It is also known in the art as "crest factor," peak-to-average ratio, or by other similar terms, known to those of ordinary skill in the art. PAR values for a variety of standard waveforms are generally known. PAR values may be obtained from theoretical calculations, or they may be measured using some PAR meters for specific situations.

As used herein, the phrase "Signal to noise ratio" (often abbreviated "SNR" or "S/N") means the ratio of signal power to the noise power associated with the signal. The noise power is considered to corrupt the signal power. Hence, SNR is a measure to quantify how much a signal has been corrupted by noise. Ideally, a good SNR should have a ratio much higher than 1:1.

While preferable embodiments have been shown and described herein, it will be obvious to those skilled in the art that such embodiments are provided by way of example only. Numerous variations, changes, and substitutions will now occur to those skilled in the art without departing from aspects of the disclosure. It should be understood that various alternatives to the embodiments of the disclosure described herein may be employed in practicing the disclosure.

We claim:

1. A method of determining information about a vascular bodily lumen, comprising:
   delivering a multiple frequency electrical signal at a plurality of frequencies to a plurality of excitation elements in the vicinity of the vascular bodily lumen;
   measuring an electrical signal from a plurality of sensing elements at least two of the plurality of frequencies in response to the delivered signal; and
   determining a lumen dimension using the measured electrical signal at the at least two frequencies by comparing the measured electrical signal with a modeled electrical signal to determine lumen dimensions.

2. The method of claim 1 wherein measuring comprises measuring voltages across the plurality of sensing elements at the at least two of the plurality of frequencies.

3. The method of claim 2 wherein determining a lumen dimension comprises converting the voltages to one or more lumen dimensions.

4. The method of claim 1 wherein the method omits injecting a fluid into the vascular bodily lumen.

5. The method of claim 1 wherein determining a lumen dimension comprises comparing a measured voltage with a modeled voltage.

6. The method of claim 5 wherein the modeled voltage is based on a modeled lumen dimension.

7. The method of claim 6 wherein the modeled lumen dimension is a lumen cross sectional area.

8. The method of claim 1 wherein comparing the measured electrical signal comprises comparing the measured electrical signal with an electrical signal from a look-up table.

9. The method of claim 8 wherein the electrical signal from the look-up table is a voltage.

10. The method of claim 1 further comprising generating the multiple frequency electrical signal at the plurality of frequencies prior to delivering a multiple frequency electrical signal.

11. The method of claim 10 wherein generating the multiple frequency electrical signal comprises generating a multiple-frequency sequence pulse having a predetermined peak to root-to-mean-square (rms) ratio.

12. A medical device adapted to determine information about a vascular bodily lumen, comprising:

an elongate device;

a plurality of excitation elements and a plurality of sensing elements disposed on the elongate device;

a controller in communication with the plurality of excitation elements, wherein the controller is configured to generate a multiple frequency electrical signal at a plurality of frequencies for delivery from the plurality of excitation elements, wherein the controller is further configured to measure an electrical signal from the plurality of sensing elements at least two of the plurality of frequencies in response to the delivered signal, and wherein the controller is further configured to compare the measured electrical signal with a modeled electrical signal to determine a lumen dimension.

13. The device of claim 12 wherein a first of the plurality of sensing elements is not equally spaced from second and third sensing elements.

14. The device of claim 12 wherein the first sensing element is disposed axially between the second and third sensing elements on the elongate device.

15. The device of claim 12 wherein the second and third sensing elements are also first and second excitation elements.

16. The device of claim 12 wherein the elongate device is a guidewire and wherein the excitation elements and sensing elements are electrodes.

17. The device of claim 12 wherein the elongate device is an angioplasty balloon catheter and wherein the excitation elements and the sensing elements are electrodes.

18. The device of claim 12 wherein the elongate device is a stent delivery catheter and wherein the excitation elements and the sensing elements are electrodes.

\* \* \* \* \*